US011807608B2

(12) United States Patent
Arbatan et al.

(10) Patent No.: US 11,807,608 B2
(45) Date of Patent: Nov. 7, 2023

(54) POLYMERIZABLE COMPOUNDS WITH ONE OR MORE SURFACTANT-LIKE PROPERTIES

(71) Applicant: University of Manitoba, Winnipeg (CA)

(72) Inventors: Tina Akbarzadeh Arbatan, Winnipeg (CA); Ahmed Abdel Rahman, Winnipeg (CA); Gurmeet Singh Bindra, Winnipeg (CA); Marcelo Dubiel, Winnipeg (CA); Zachary Wolff, Winnipeg (CA); Chenxi Ning, Winnipeg (CA)

(73) Assignee: UNIVERSITY OF MANITOBA, Winnipeg (CA)

( * ) Notice: Subject to any disclaimer, the term of this patent is extended or adjusted under 35 U.S.C. 154(b) by 579 days.

(21) Appl. No.: 16/635,523

(22) PCT Filed: Jul. 31, 2018

(86) PCT No.: PCT/CA2018/050934
§ 371 (c)(1),
(2) Date: Jan. 30, 2020

(87) PCT Pub. No.: WO2019/023798
PCT Pub. Date: Feb. 7, 2019

(65) Prior Publication Data
US 2020/0339512 A1    Oct. 29, 2020

Related U.S. Application Data

(60) Provisional application No. 62/539,041, filed on Jul. 31, 2017.

(51) Int. Cl.
| | | |
|---|---|---|
| *C07D 211/58* | (2006.01) | |
| *C07F 9/59* | (2006.01) | |
| *C09D 7/65* | (2018.01) | |
| *C09D 7/63* | (2018.01) | |
| *C08L 33/14* | (2006.01) | |
| *C08L 33/26* | (2006.01) | |
| *C08L 43/02* | (2006.01) | |
| *C09D 5/02* | (2006.01) | |
| *C09D 5/14* | (2006.01) | |
| *C09D 133/14* | (2006.01) | |
| *C09D 133/26* | (2006.01) | |
| *C09D 139/04* | (2006.01) | |

(52) U.S. Cl.
CPC .............. *C07D 211/58* (2013.01); *C07F 9/59* (2013.01); *C08L 33/14* (2013.01); *C08L 33/26* (2013.01); *C08L 43/02* (2013.01); *C09D 5/02* (2013.01); *C09D 5/14* (2013.01); *C09D 7/63* (2018.01); *C09D 7/65* (2018.01); *C09D 133/14* (2013.01); *C09D 133/26* (2013.01); *C09D 139/04* (2013.01)

(58) Field of Classification Search
CPC .................................. C07D 211/58; C07F 9/59
See application file for complete search history.

(56) References Cited

U.S. PATENT DOCUMENTS 3,560,494 A    2/1971    Copp

FOREIGN PATENT DOCUMENTS

| CN | 109311810 A | 2/2019 | |
|---|---|---|---|
| WO | 2010054009 A1 | 5/2010 | |
| WO | 2017/063091 A1 | 4/2017 | |
| WO | 2017/079825 A1 | 5/2017 | |
| WO | WO-2017079841 A1 * | 5/2017 | ........... C08K 5/3415 |
| WO | 2017197518 A1 | 11/2017 | |
| WO | 2018/006175 A1 | 1/2018 | |
| WO | WO-2018005794 A2 * | 1/2018 | ................ A61P 3/10 |
| WO | 2018/049508 A1 | 3/2018 | |

OTHER PUBLICATIONS

Chemical Abstracts Registry No. 2172368-53-3, indexed in the Registry file on STN CAS Online Jan. 31, 2018. (Year: 2018).*
Chemical Abstracts Registry No. 2156612-76-7, indexed in the Registry file on STN CAS Online Dec. 12, 2017. (Year: 2017).*
Chemical Abstracts Registry No. 2093158-13-3, indexed in the Registry file on STN CAS Online Apr. 25, 2017. (Year: 2017).*
Chemical Abstracts Registry No. 2093158-29-1, indexed in the Registry file on STN CAS Online Apr. 25, 2017. (Year: 2017).*
Lingdong Li et al., "Synthesis of quaternary phosphonium N-chloramine biocides for antimicrobial applications", Royal Society of Chemistry; RSC Adv., 2017, 7, 13244-13249; DOI: 10.1039/c6ra24954j; Accepted Feb. 21, 2017.
International Search Report issued in corresponding Application No. PCT/CA2018/050934, dated Nov. 7, 2018.
Written Opinion issued in corresponding Application No. PCT/CA2018/050934, dated Nov. 7, 2018.
Office Action issued in corresponding Chinese Patent Application No. 201880061022.5 dated Nov. 3, 2022.

* cited by examiner

*Primary Examiner* — Laura L Stockton
(74) *Attorney, Agent, or Firm* — Chamberlain, Hrdlicka, White, Williams & Aughtry

(57) ABSTRACT

Some embodiments of the present disclosure relate to polymerizable compounds that comprise biocidal activity and/or the potential for increased biocidal activity and that comprise at least one hydrophobic portion and at least one hydrophilic portion. Together the hydrophobic portion and the hydrophilic portion of the compounds may provide the polymerizable compounds with one or more surfactant-like properties. The polymerizable compounds can be incorporated into polymer coating formulations. The polymer coating formulations can be used to coat one or more surfaces of a substrate. The coating formulation can provide biocidal activity and/or the potential for increased biocidal activity to the coated substrate-surface.

7 Claims, 43 Drawing Sheets

POLYMERIZABLE COMPOUNDS WITH ONE OR MORE SURFACTANT-LIKE PROPERTIES

TECHNICAL FIELD

The present disclosure relates to the field of biocidal compounds and precursors thereof. In particular, the present disclosure relates to biocidal compounds, and precursors thereof, that have surfactant-like properties.

BACKGROUND

Microbial resistance to biocidal compounds poses a large and growing threat to human health. Various circumstances and applications call for the use of biocidal compounds. Currently, there are different broad-spectrum biocidal compounds that are employed extensively during disinfection applications, including: silver, hydrogen peroxide, nitrogen oxide, sodium hypochlorite, quaternary ammonium compounds (QAC) and N-halamine compounds.

It is known to incorporate biocidal compounds into polymer coatings for hard and soft surfaces in an effort to provide a polymer coating with biocidal activity. Surfactants are also known to be used in the process for making polymer coatings, such as coatings that include latex-polymer particles. However, utilizing a surfactant compound in an emulsion polymerization process can have detrimental effects. These detrimental effects can be caused by weak hydrophobic interactions between the surfactant compound and latex-polymer particles within the emulsion, which can allow the physically-adsorbed surfactant compound to desorb from the surface of the latex-polymer particle. This desorption can destabilize the latex, which can be exacerbated under one or more of: exposure to high shear, freezing, high and low temperatures and exposure to high ionic-strength conditions. Furthermore, when the polymer latex is applied as a polymer-coating film, the physically-adsorbed surfactant compound can migrate toward the air-film or the substrate-film interface. During film formation, surfactant compounds that are strongly adsorbed may also be trapped at particle/particle boundaries, which can create hydrophilic pathways within the polymer-coating film. In some cases, the surfactant compound may be pushed away from the particle/particle boundaries, which can create small pockets or aggregates throughout the polymer-coating film. Such a heterogeneous distribution of the surfactant compound within the polymer-coating film may adversely affect the coating film's performance. For example, it is known that adhesion strength, shear strength, water resistance, gloss and film appearance can be adversely affected by any migration of the surfactant compounds within a polymer-coating film.

SUMMARY

Embodiments of the present disclosure relate to compounds that are selected from a group of compounds that comprise: one or more cationic centers; at least one N-halamine group and/or a precursor thereof; and at least one coating-incorporation group (CIG).

Some embodiments of the present disclosure comprise compounds that are selected from a group of polymerizable compounds that comprise: at least one cationic centers; at least one N-halamine group and/or a precursor thereof; and at least one CIG.

Some embodiments of the present disclosure comprise compounds that are selected from a group of polymerizable compounds that have surfactant-like properties and that comprise: one or more cationic centers; at least one N-halamine group and/or a precursor thereof; one or more lipophilic moieties; and at least one CIG.

Some embodiments of the present disclosure relate to polymerizable compounds that have surfactant-like properties, a cationic charge and biocidal activity, or the potential for increased biocidal activity. Some embodiments of the present disclosure relate to compounds with the following general-formula (Formula 1):

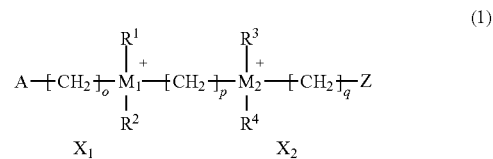

wherein,
A is an N-halamine precursor that may be selected from a group comprising imidazolidine-2,4-dione (hydantoin); 5,5-dimethylhydantoin; 4,4-dimethyl-2-oxazalidione; tetramethyl-2-imidazolidione; 2,2,5,5-tetramethylimidazo-lidin-4-one; a uracil derivative; and piperidine, including 2,2,6,6-tetramethyl-piperidine;
$M_1$ and $M_2$ are each independently selected from nitrogen, phosphorous or nil, but both are not nil;
$R_1$, $R_2$, $R_3$ and $R_4$ are each independently selected from a group consisting of: a linear alkyl group ($C_nH_{(2n+1)}$) where n is an integer between 0 and 18; a branched alkyl group ($C_mH_{(2m+1)}$) where m is an integer between 0 and 18; a phenyl group; a cyclohexyl group; a linear alkyloyl group: ($C_aH_{2a}OH$) where a is an integer between 0 and 18; and a branched alkyloyl group ($C_bH_{2b}OH$) where b is an integer between 0 and 18, wherein in $R_1$ and $R_2$ n, m, a and b are 0 when $M_1$ is nil, and wherein $R_3$ and $R_4$ n, m, a and b are 0 when $M_2$ is nil;
$X_1$ and $X_2$ are ions each independently selected from one of $Cl^-$, $Br^-$, $I^-$ and $PO_4^{3-}$; o, p and q are each an integer independently selected between 0 and 12; and Z is selected from a group comprising at least one of vinyl, vinyl derivative, methyl methacrylate, acrylate, styrene, vinyl benzyl, acrylamide, epoxy, —COOH, —CHO, —CN, —NCO, —NH2, —CNO, —SCN, —NCS and —OH.

Some of embodiments of the present disclosure relate to polymerizable compounds with the following general formula (Formula 2):

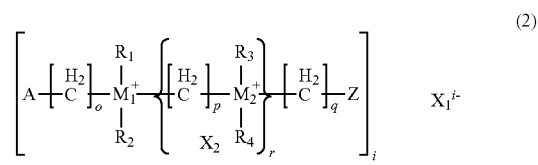

wherein,
A is an N-halamine precursor that may be selected from a group comprising imidazolidine-2,4-dione (hydantoin); 5,5-dimethylhydantoin; 4,4-dimethyl-2-oxazalidione; tetramethyl-2-imidazolidione; 2,2,5,5-tetramethylimidazo-lidin-4-one; a uracil derivative; piperidine and 2,2,6,6-tetramethyl-piperidine;
$M_1$ and $M_2$ are each independently selected from nitrogen, phosphorous or nil, but both are not nil;

$R_1$, $R_2$, $R_3$ and $R_4$ are each independently selected from a group consisting of: a linear alkyl group ($C_nH_{(2n+1)}$) where n is an integer between 0 and 18; a branched alkyl group ($C_mH_{(2m+1)}$) where m is an integer between 0 and 18; a phenyl group; a cyclohexyl group; a linear alkyloyl group: ($C_aH_{2a}OH$) where a is an integer between 0 and 18; or a branched alkyloyl group ($C_bH_{2b}OH$) where b is an integer between 0 and 18, wherein in $R_1$ and $R_2$ n, m, a and b are 0 when $M_1$ is nil, and wherein $R_3$ and $R_4$ n, m, a and b are 0 when $M_2$ is nil;

$X_1$ and $X_2$ are ions each independently selected from one of $Cl^-$, $Br^-$, $I^-$ and $PO_4^{3-}$;

o, p, q and r are each an integer independently selected between 0 and 12; and Z is selected from a group comprising at least one of vinyl, vinyl derivative, methyl methacrylate, acrylate, styrene, vinyl benzyl, acrylamide, epoxy, —COOH, —CHO, —CN, —NCO, —NH2, —CNO, —SCN, —NCS and —OH; and i is an integer between 1 and 5.

Some of embodiments of the present disclosure relate to polymerizable compounds with the following general-formula (Formula 3):

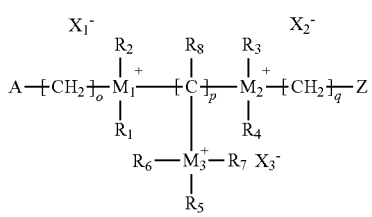

(3)

wherein,

A is an N-halamine precursor that may be selected from a group comprising imidazolidine-2,4-dione (hydantoin); 5,5-dimethylhydantoin; 4,4-dimethyl-2-oxazalidione; tetramethyl-2-imidazolidione; 2,2,5,5-tetramethylimidazo-lidin-4-one; a uracil derivative; and piperidine, including 2,2,6,6-tetramethyl-piperidine $M_1$, $M_2$ and $M_3$ are each independently selected from nitrogen or phosphorous; $R_1$, $R_2$, $R_3$, $R_4$, $R_5$, $R^6$, $R^7$ and $R^8$ are each independently selected from: a linear alkyl group ($C_nH_{2n+1}$) where n is an integer between 0 and 18; a phenyl group; a cyclohexane group; or an alkyloyl group ($C_mH_{2m}OH$) where m is an integer between 0 and 18;

$X_1^-$, $X_2^-$ and $X_3^-$ are ions each independently selected from but not limited to $Cl^-$, $Br^-$, $I^-$ or $PO_4^{3-}$;

o, p and q are each an integer independently selected between 0 and 12; and Z is selected from a group comprising at least one of vinyl, vinyl derivative, methyl methacrylate, acrylate, styrene, vinyl benzyl, acrylamide, epoxy, —COOH, —CHO, —CN, —NCO, —NH2, —CNO, —SCN, —NCS and —OH.

Some of embodiments of the present disclosure relate to polymerizable compounds with the following general-formula (Formula 4):

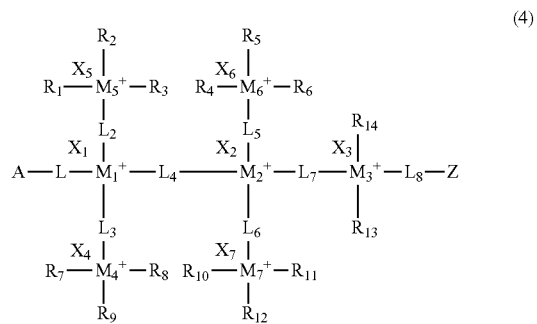

(4)

wherein,

A is an N-halamine precursor that may be selected from a group comprising imidazolidine-2,4-dione (hydantoin); 5,5-dimethylhydantoin; 4,4-dimethyl-2-oxazalidione; tetramethyl-2-imidazolidione; 22,5,5-tetramethylimidazo-lidin-4-one; a uracil derivative; piperidine and 2,26,6-tetramethyl-piperidine;

$M_1$, $M_2$, $M_3$, $M_4$, $M_5$, $M_6$ and $M_7$ are each independently selected from nitrogen, phosphorous or nil, wherein not all are nil;

$R_1$, $R_2$, $R_3$, $R_4$, $R_5$, $R_6$, $R_7$, $R_8$, $R_9$, $R_{10}$, $R_{11}$, $R_{12}$, Ru and $R_{14}$ are each independently selected from a linear alkyl group ($C_nH_{2n+1}$) where n is an integer between and 18; a branched alkyl group ($C_mH_{(2m+1)}$) where m is an integer between 0 and 18; a phenyl group; a cyclohexyl group; a linear alkyloyl group ($C_aH_{2a}OH$) where a is an integer between 0 and 18; and a branched alkyloyl group ($C_bH_{2b}OH$) where b is an integer between 0 and 18, wherein in $R_1$, $R_2$ and $R_3$ n, m, a and b are 0 when $M_5$ is nil, wherein in $R_4$, $R_5$ and $R_6$ n, m, a and b are 0 when $M_6$ is nil; wherein in $R_7$, $R_8$ and $R_9$n, in, a and b are 0 when $M_4$ is nil, wherein in $R_{10}$, $R_{11}$ and $R_{12}$ n, m, a and b are 0 when $M_7$ is nil, and wherein in $R_{13}$ and $R_{14}$ n, m, a and b are 0 when $M_3$ is nil;

$X_1$, $X_2$, $X_3$, $X_4$, $X_5$, $X_6$ and $X_7$ are ions each independently selected from one of $Cl^-$, $Br^-$, $I^-$ and $PO_4^{3-}$;

$L_1$, $L_2$, $L_3$, $L_5$, $L_6$ and $L_8$ are each selected from nil, linear alkylene ($C_dH_{(2d+1)}$) where d is an integer between 0 and 18; a branched alkylene ($C_eH_{(e+1)}$) where e is an integer between 0 and 18; a linear alkylol ($C_fH_{2f}OH$) where f is an integer between 0 and 18; or a branched alkylol ($C_gH_{2g-2}OH$) where g is an integer between 0 and 18;

$L_4$ and $L_7$ are each selected from a linear alkylene ($C_dH_{(2d+1)}$) where d is an integer between 0 and 18; a branched alkylene ($C_eH_{(e+1)}$) where e is an integer between 0 and 18; a linear alkylol ($C_fH_{2f}OH$) where f is an integer between 0 and 18; or a branched alkylol ($C_gH_{2g-2}OH$) where g is an integer between 0 and 18;

Z is selected from at least one of vinyl, vinyl derivative, methyl methacrylate, acrylate, styrene, vinyl benzyl, acrylamide, epoxy, —COOH, —CHO, —CN, —NCO, —NH2, —CNO, —SCN, —NCS or —OH.

Some of embodiments of the present disclosure relate to polymerizable compounds with the following general-formula (Formula 4A):

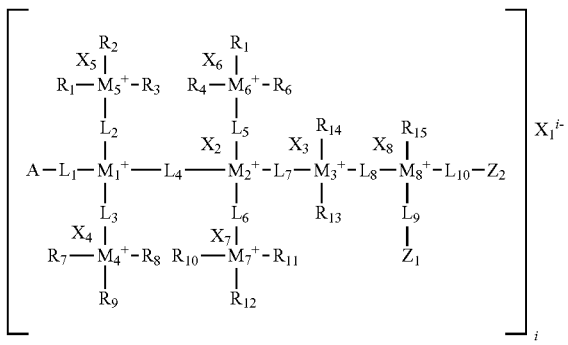

(4A)

wherein,
A is an N-halamine precursor that may be selected from a group comprising imidazolidine-2,4-dione (hydantoin); 5,5-dimethylhydantoin; 4,4-dimethyl-2-oxazalidione; tetramethyl-2-imidazolidione; 2,2,5,5-tetramethylimidazo-lidin-4-one; a uracil derivative; and piperidine, including 2,2,6,6-tetramethyl-piperidine $M_1$, $M_2$, $M_3$, $M_4$, $M_5$, $M_6$, $M_7$, and $M_8$ are each independently selected from nitrogen, phosphorous or nil; $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{15}$ are each independently selected from a linear alkyl group $(C_nH_{(2n+1)})$; a branched alkyl group $(C_mH_{(2m+1)})$ where m is an integer between 0 and 18; a phenyl group; a cyclohexane group; a linear alkyloyl group $(C_aH_{2a}OH)$ where a is an integer between 0 and 18; and a branched alkyloyl group $(C_bH_{2b}OH)$ where b is an integer between 0 and 18;

$X_1$, $X_2$, $X_3$, $X_4$, $X_5$, $X_6$, $X_7$ and $X_8$ are each independently selected from but not limited to Cl⁻, Br⁻, I⁻ or $PO_4^{3-}$;

L1, L2, L3, L5, L6, L8, L9 and L10 are each independently selected from nil, a linear alkyl (CdH(2d+1)) where b is an integer between 0 and 18; a branched alkyl (CeH(2e-1)) where e is an integer between 0 and 18; a linear alkylol (CfH2fOH) where f is an integer between 0 and 18; or a branched alkylol (CgH2gOH) where g is an integer between 0 and 18; i is an integer selected between 1 and 5; and Z1 and Z2 are each independently selected from at least one of vinyl, vinyl derivative, methyl methacrylate, acrylate, styrene, vinyl benzyl, acrylamide, epoxy, —COOH, —CHO, —CN, —NCO, —NH2, —CNO, —SCN, —NCS, —OH or nil.

Some embodiments of the present disclosure relate to incorporating one or more of the compounds of Formula 1, Formula 2, Formula 4 or Formula 4A into polymers. Some further embodiments of the present disclosure relate to using said polymers as a component of a coating that has biocidal activity and/or the potential for increased biocidal activity. Some further embodiments of the present disclosure relate to using said coating to coat one or more surfaces of a substrate so that the coated substrate has biocidal activity and/or the potential for increased biocidal activity. The potential for increased biocidal activity may be realized by exposing the compounds of Formula 1, Formula 2, Formula 3 or Formula 4, the polymer, the coating or the coated substrate to one or more further agents, such as one or more halogen-containing agents.

Some embodiments of the present disclosure relate to resins that comprise one or more of the compounds of Formula 1, Formula 2, Formula 4 or Formula 4A.

Some embodiments of the present disclosure relate to polymerizable compounds with biocidal activity and/or the potential for increased biocidal activity and such polymerizable compounds include at least one hydrophobic portion and at least one hydrophilic portion. Together the hydrophobic portion and the hydrophilic portion of the compounds may provide the compounds with one or more surfactant-like properties.

Some embodiments of the present disclosure relate to compounds with surfactant-like properties, biocidal activity and/or the potential for increased biocidal activity and these compounds are monomers that can be incorporated into a polymer. Without being bound by any particular theory, some of the compounds of the present disclosure can be positioned at an interface between a hydrophobic phase and a hydrophilic phase during a latex-synthesis process that includes an emulsification step or an emulsification step and a polymer formation step.

Some embodiments of the present disclosure may facilitate one or more steps of a latex-synthesis process such as: an emulsification step of droplets that comprise one or more compounds/monomers and/or of seed particles; a nucleation step; a particle growth step; or a stabilization step of the polymer-particles during and after the polymerization. Some embodiments of the present disclosure relate to latex emulsions that may also enhance the shelf life of polymers, any coatings made therewith and any substrates that are coated with such coatings. The latex emulsions of the present disclosure may be stored as a fluid emulsion, used as a component of a coating formulation or dried—or otherwise cured—to form a latex-emulsion based film.

Some embodiments of the present disclosure relate to surfactant compounds that are polymerizable. Polymerizable surfactants are also referred to as surfmers. A polymerizable surfactant is a compound that can be chemically incorporated into polymer particles—by being covalently bonded with chemical components of the polymer—during a latex-synthesis process or otherwise. Without being bound by any particular theory, desorption of the surfactant compounds from the polymer particles and migration within the resulting polymer film are each or both impeded or limited. Some embodiments of the present disclosure relate to polymerizable surfactant-compounds that have biocidal activity and/or the potential for increased biocidal activity. Furthermore, when the polymerizable surfactant-compounds of the present disclosure are chemically incorporated into a polymer particle, that polymer particle may have biocidal activity and/or the potential for increased biocidal activity. When the polymer particles are components of a coating formulation, that coating formulation may have biocidal activity and/or the potential for increased biocidal activity. When the polymer particles are within a latex emulsion, that latex emulsion may have biocidal activity and/or the potential for increased biocidal activity.

Some embodiments of the present disclosure relate to the use of a polymerizable compound with surfactant-like properties for making a coating, wherein the polymerizable compound comprises at least one cationic center and at least one coating incorporation group.

Some embodiments of the present disclosure relate to polymeric coatings and substrates coated therewith that have biocidal activity and/or the potential for increased biocidal activity and that may: reduce or avoid any release of compounds with biocidal activity and/or the potential for biocidal activity into the surrounding environment; reduce or avoid microbes developing resistance to the compounds with biocidal activity and/or the potential for biocidal activity within the polymeric coatings; allow for safe handling; and provide chemical components with lower or no volatility and that do not easily permeate through contact with skin. The polymeric coatings may have one or more biocidal functionalities that are part of a surfactant compound, which may increase positioning of the biocidal functionalities at or near the surface of the coating rather than the biocidal functionalities being physically buried within a bulk phase of the coating and away from the surface where microbes interact with the coating.

BRIEF DESCRIPTION OF THE DRAWINGS

These and other features of the present disclosure will become more apparent in the following detailed description in which reference is made to the appended drawings, wherein:

FIG. 25 shows photographs of a polyurethane-based coating during humidity resistance testing, wherein FIG. 25A shows the coating at day 7; FIG. 25B shows the coating at day 29; and, FIG. 25C shows the coating at day 50;

FIG. 26 shows photographs of a polyurethane-based coating according to embodiments of the present disclosure during humidity resistance testing, wherein FIG. 26A shows the coating at day 7; FIG. 26B shows the coating at day 14; and, FIG. 26C shows the coating at day 26;

FIG. 27 shows photographs of a polyurethane-based coating according to embodiments of the present disclosure during humidity resistance testing, wherein FIG. 27A shows the coating at day 7; FIG. 27B shows the coating at day 14; and, FIG. 27C shows the coating at day 26;

FIG. 28 shows photographs of a polyurethane-based coating according to embodiments of the present disclosure during humidity resistance testing, wherein FIG. 28A shows the coating at day 3; and, FIG. 28B shows the coating at day 13;

FIG. 26 shows photographs of a polyurethane-based coating according to embodiments of the present disclosure during humidity resistance testing, wherein FIG. 26A shows the coating at day 7; FIG. 26B shows the coating at day 14; and, FIG. 26C shows the coating at day 26;

FIG. 29 shows photographs of a polyurethane-based coating according to embodiments of the present disclosure during humidity resistance testing, wherein FIG. 29A shows the coating at day 3; and, FIG. 29B shows the coating at day 13;

FIG. 31 shows photographs of a polyurethane-based coating according to embodiments of the present disclosure during humidity resistance testing, wherein FIG. 31A shows the coating at day 3; and, FIG. 31B shows the coating at day 13;

FIG. 32 shows photographs of a polyurethane-based coating according to embodiments of the present disclosure during humidity resistance testing, wherein FIG. 32A shows the coating at day 3; and, FIG. 32B shows the coating at day 13;

FIG. 33 shows photographs of a polyurethane-based coating according to embodiments of the present disclosure during humidity resistance testing, wherein FIG. 33A shows the coating at day 3; and, FIG. 33B shows the coating at day 13;

FIG. 34 shows photographs of the coating of FIG. 25 during ultraviolet resistance testing, wherein FIG. 34A shows the coating at day 7; and, FIG. 34B shows the coating at day 29;

FIG. 35 shows photographs of the coating of FIG. 26 during ultraviolet resistance testing, wherein FIG. 35A shows the coating at day 7; FIG. 35B shows the coating at day 14; and, FIG. 35C shows the coating at day 26;

FIG. 36 shows photographs of the coating of FIG. 27 during ultraviolet resistance testing, wherein FIG. 36A shows the coating at day 7; FIG. 35B shows the coating at day 14; and, FIG. 35C shows the coating at day 26;

FIG. 37 shows photographs of the coating of FIG. 28 during ultraviolet resistance testing, wherein FIG. 36A shows the coating at day 3; and, FIG. 37B shows the coating at day 13;

FIG. 38 shows photographs of the coating of FIG. 29 during ultraviolet resistance testing, wherein FIG. 36A shows the coating at day 3; and, FIG. 37B shows the coating at day 13;

FIG. 40 shows photographs of the coating of FIG. 31 during ultraviolet resistance testing, wherein FIG. 40A shows the coating at day 3; and, FIG. 40B shows the coating at day 13;

FIG. 41 shows photographs of the coating of FIG. 32 during ultraviolet resistance testing, wherein FIG. 41A shows the coating at day 3; and, FIG. 41B shows the coating at day 13;

FIG. 42 shows photographs of the coating of FIG. 33 during ultraviolet resistance testing, wherein FIG. 42A shows the coating at day 3; and, FIG. 42B shows the coating at day 13.

DETAILED DESCRIPTION

Figure 1:
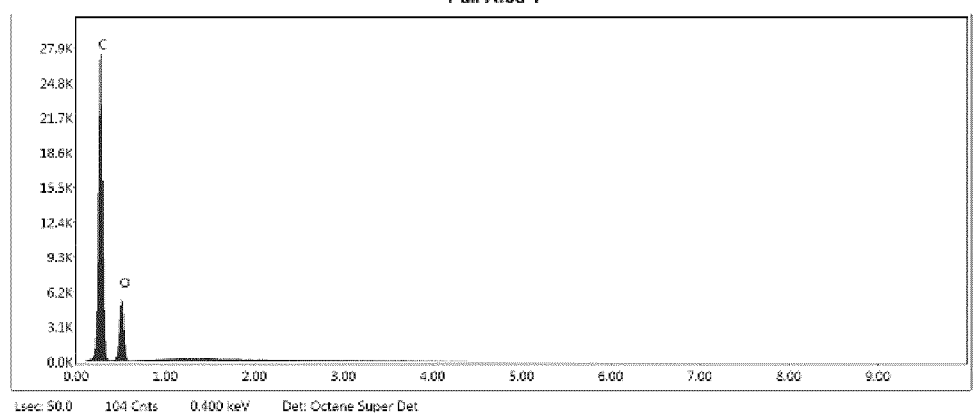
FIG. 1 is an example of experimental data obtained from an energy dispersive X-ray spectroscopy (EDX) system that analyzed an F3 control latex-formulation that was not exposed to one or more further agents.
Figure 2:
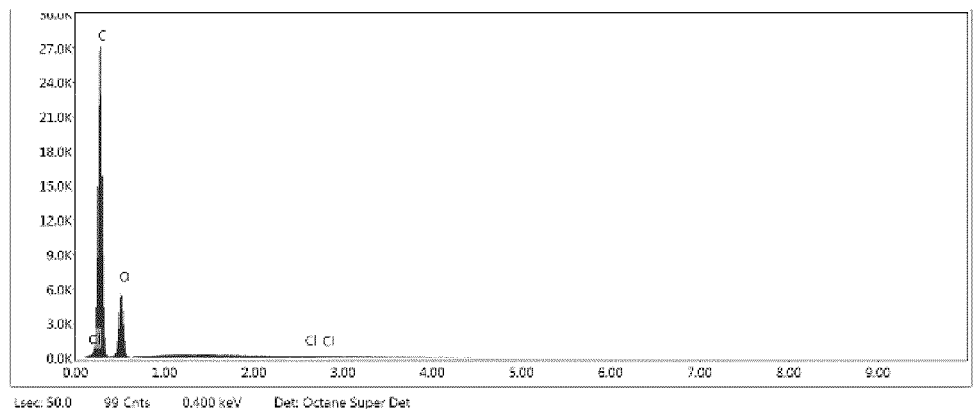
FIG. 2 is an example of experimental data obtained from an EDX system that analyzed an F3 control latex-formulation that was exposed to one or more further agents.
Figure 3:
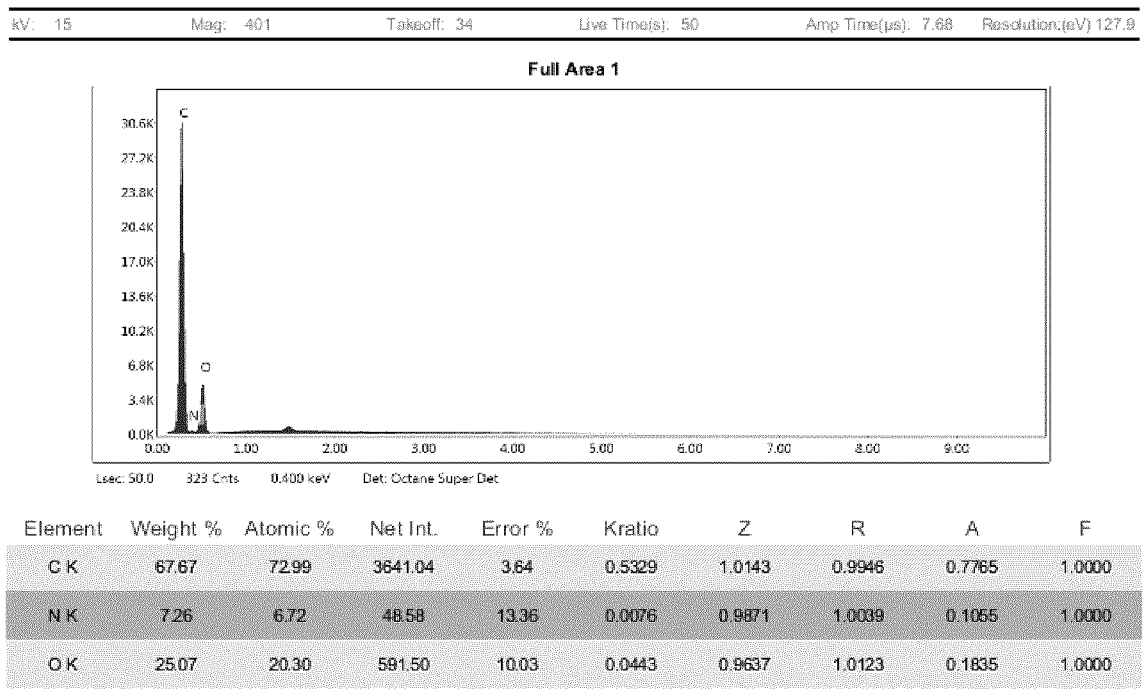
FIG. 3 is an example of experimental data obtained from an EDX system that analyzed an F3-C3-MMAcryl-4.6% latex-coating variant that was not chlorinated.
Figure 4:
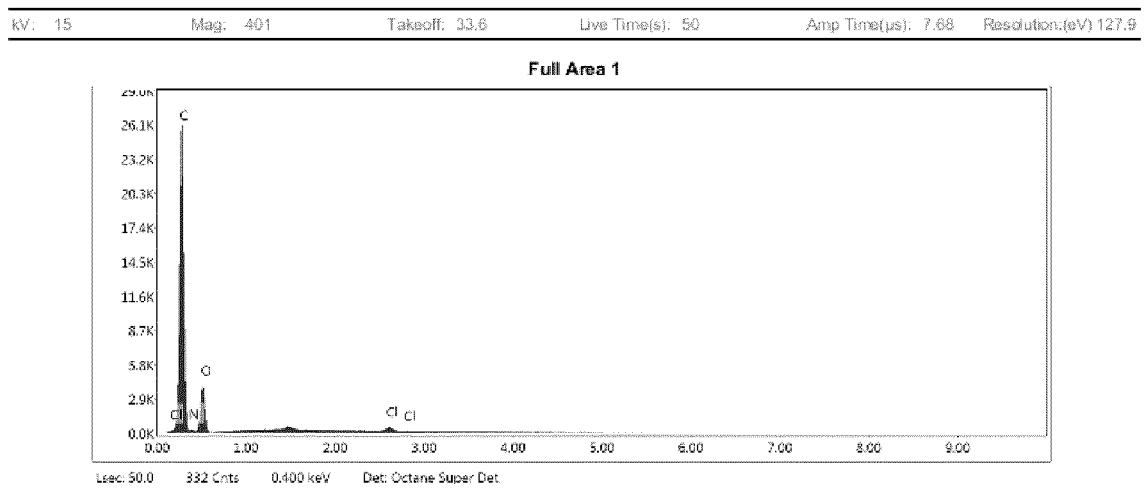
FIG. 4 is an example of experimental data obtained from an EDX system that analyzed an F3-C3-MMAcryl-4.6% latex-coating variant that was chlorinated.
Figure 5:
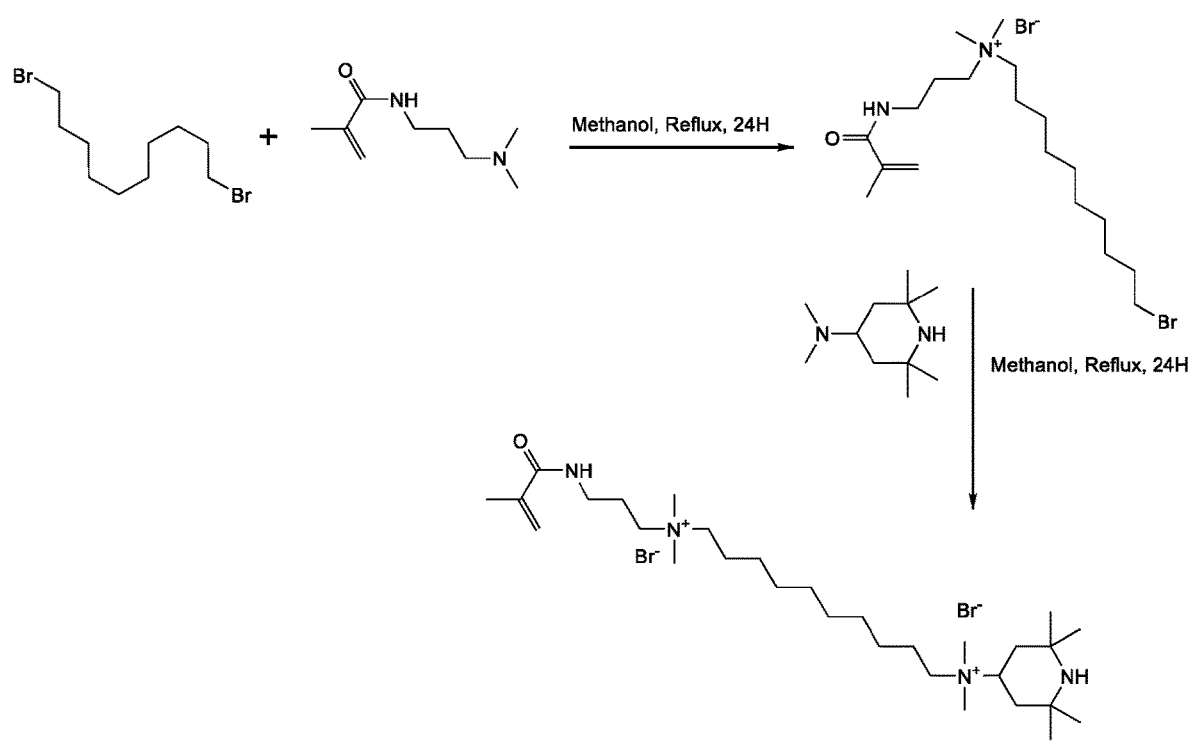
FIG. 5 is an example of a synthesis pathway for making a compound according to embodiments of the present disclosure.
Figure 6:
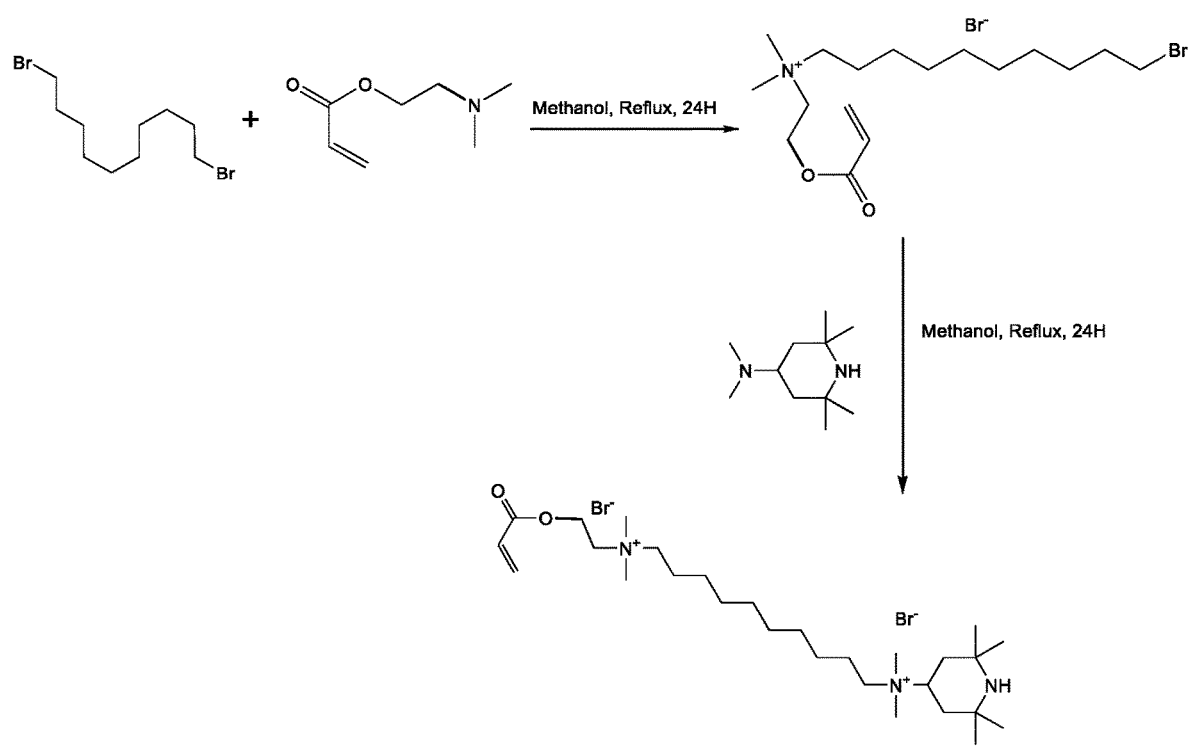
FIG. 6 is an example of a synthesis pathway for making a compound according to embodiments of the present disclosure.
Figure 7:
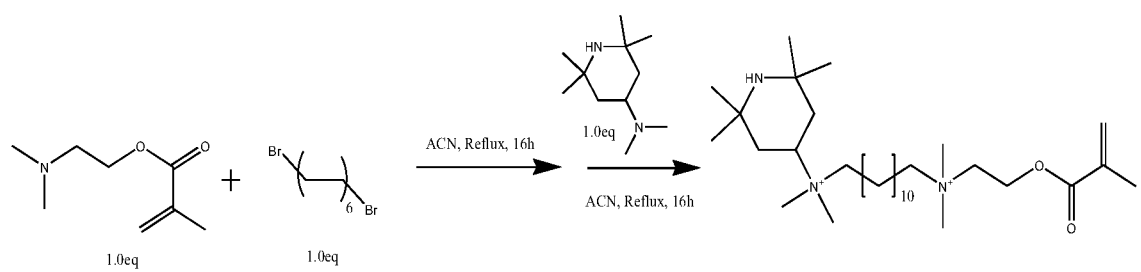
FIG. 7 is an example of a synthesis pathway for making a compound according to embodiments of the present disclosure.
Figure 8:
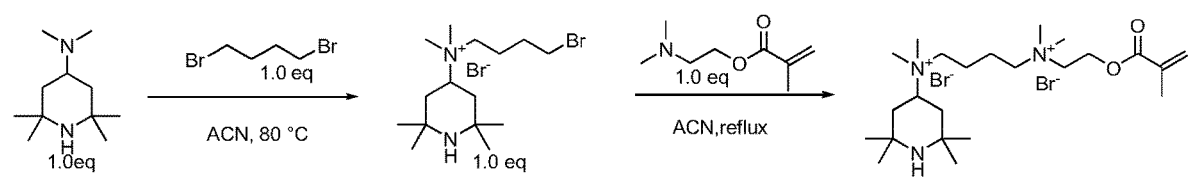
FIG. 8 is an example of a synthesis pathway for making a compound according to embodiments of the present disclosure.
Figure 9:
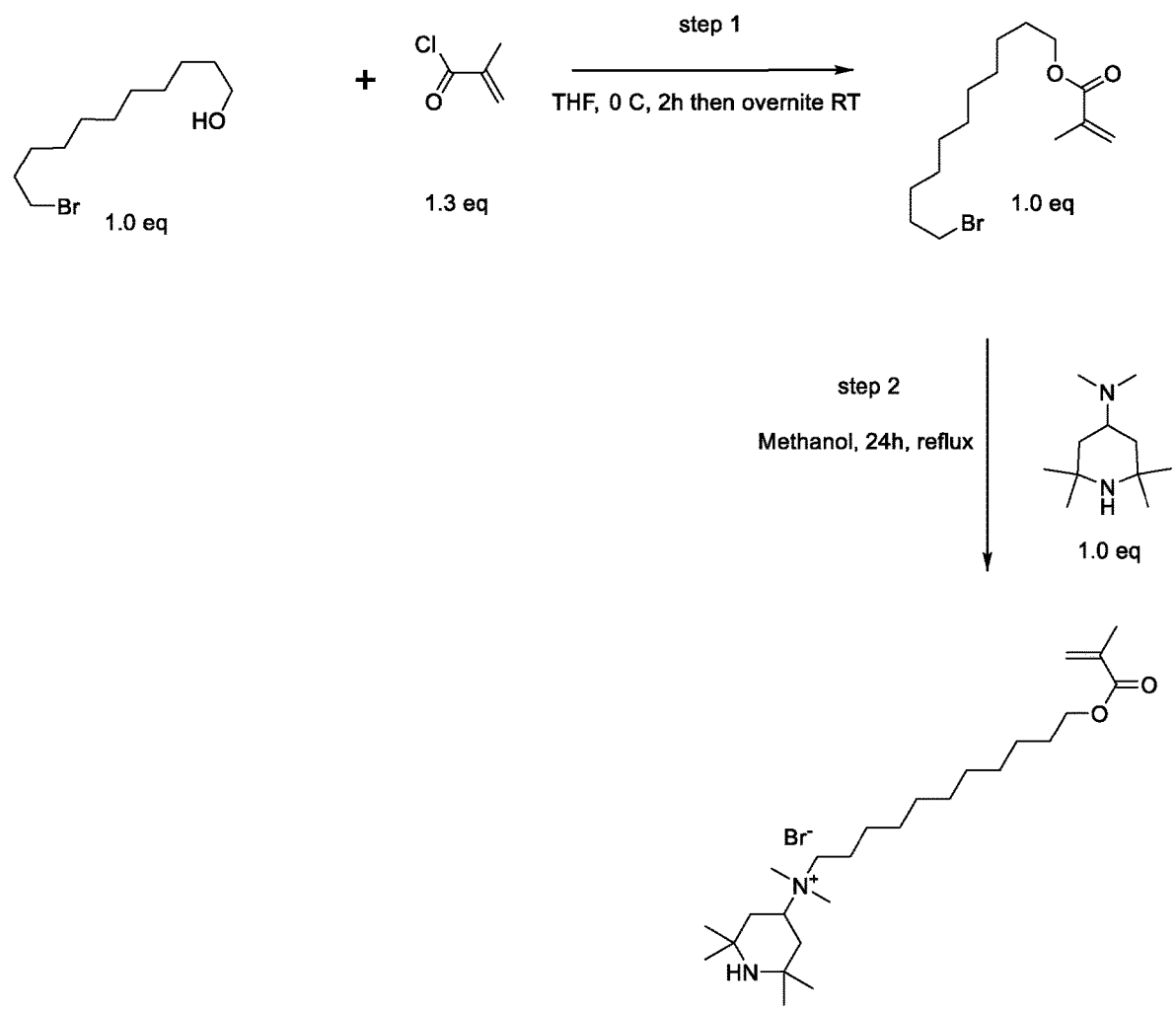
FIG. 9 is an example of a synthesis pathway for making a compound according to embodiments of the present disclosure.
Figure 10:
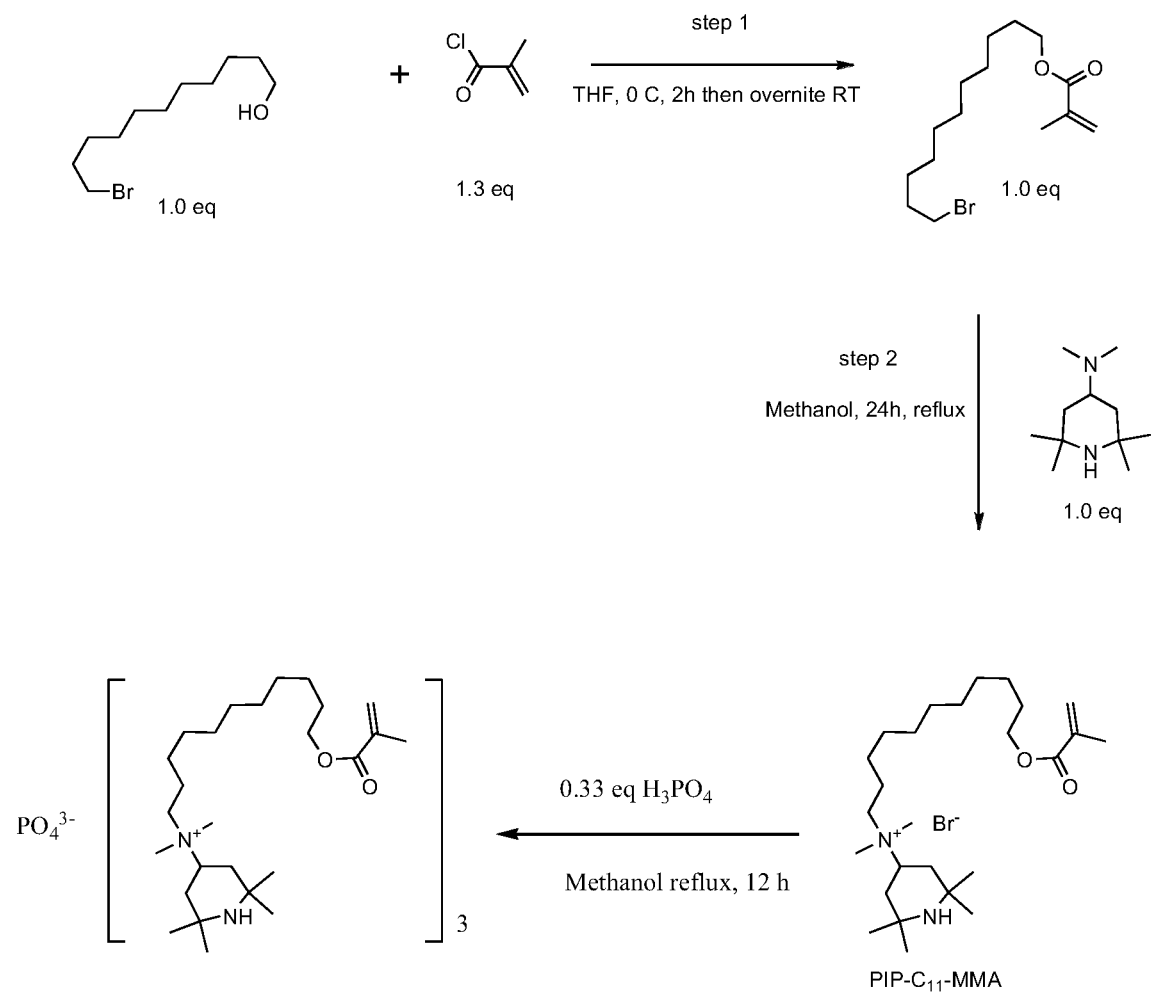
FIG. 10 is an example of a synthesis pathway for making a compound according to embodiments of the present disclosure.
Figure 11:
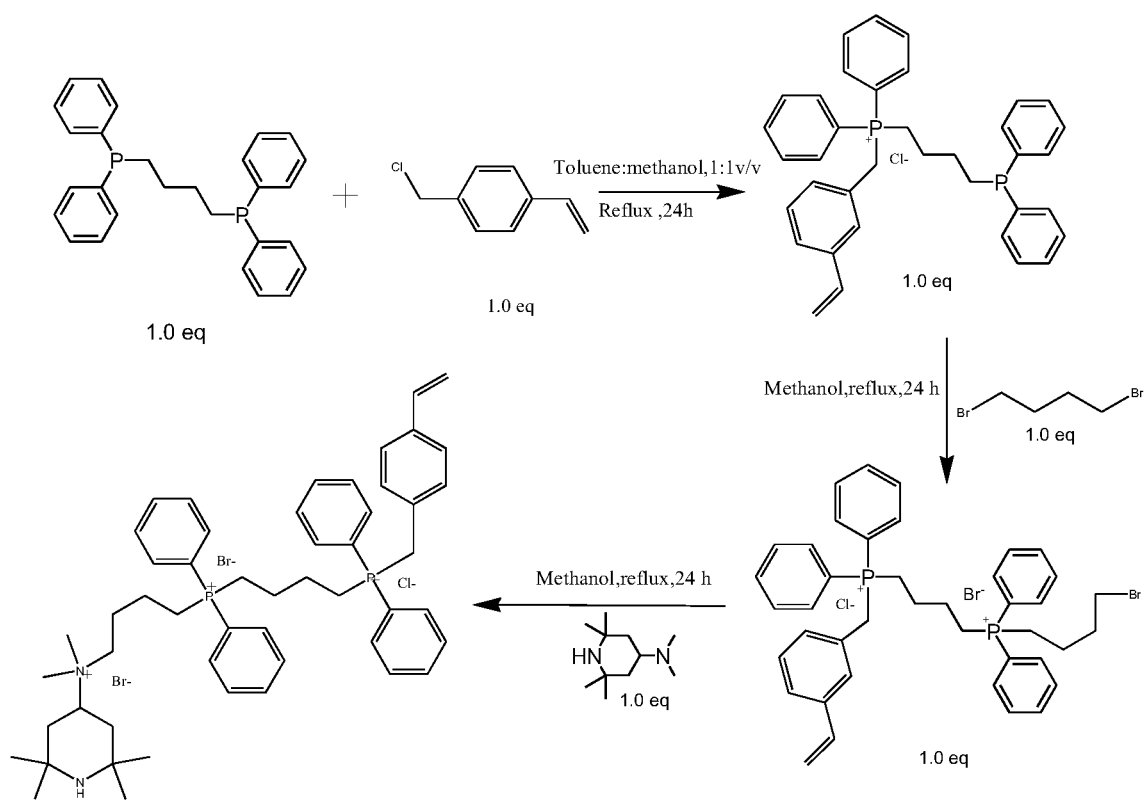
FIG. 11 is an example of a synthesis pathway for making a compound according to embodiments of the present disclosure.
Figure 12:
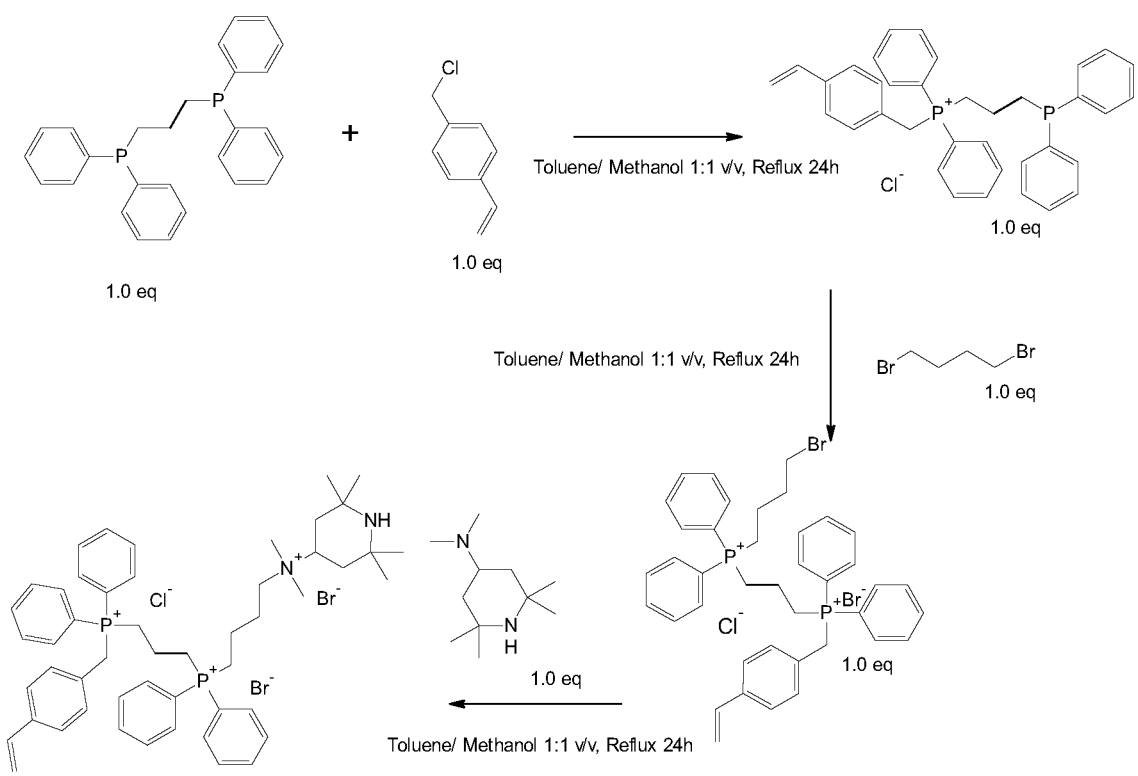
FIG. 12 is an example of a synthesis pathway for making a compound according to embodiments of the present disclosure.
Figure 13:
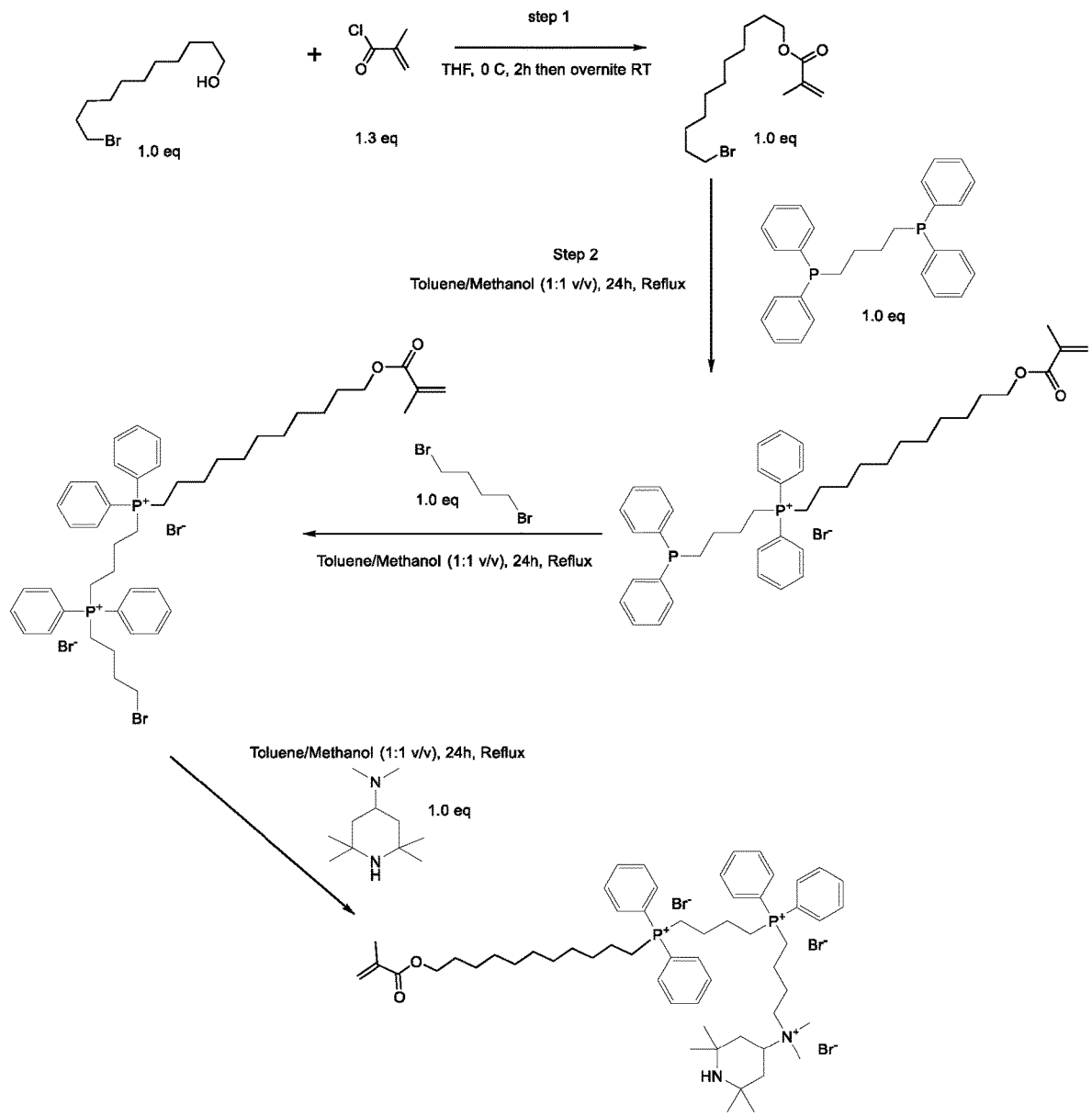
FIG. 13 is an example of a synthesis pathway for making a compound according to embodiments of the present disclosure.
Figure 14:
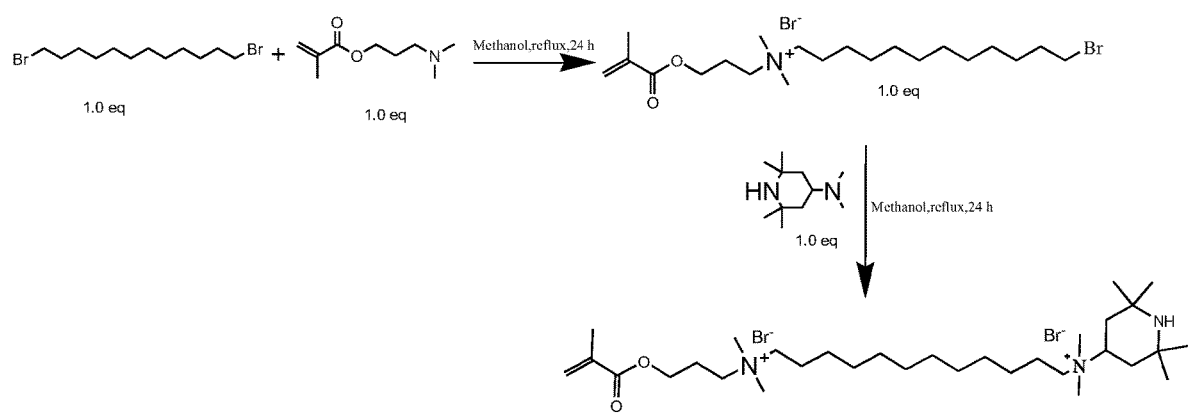
FIG. 14 is an example of a synthesis pathway for making a compound according to embodiments of the present disclosure.
Figure 15:
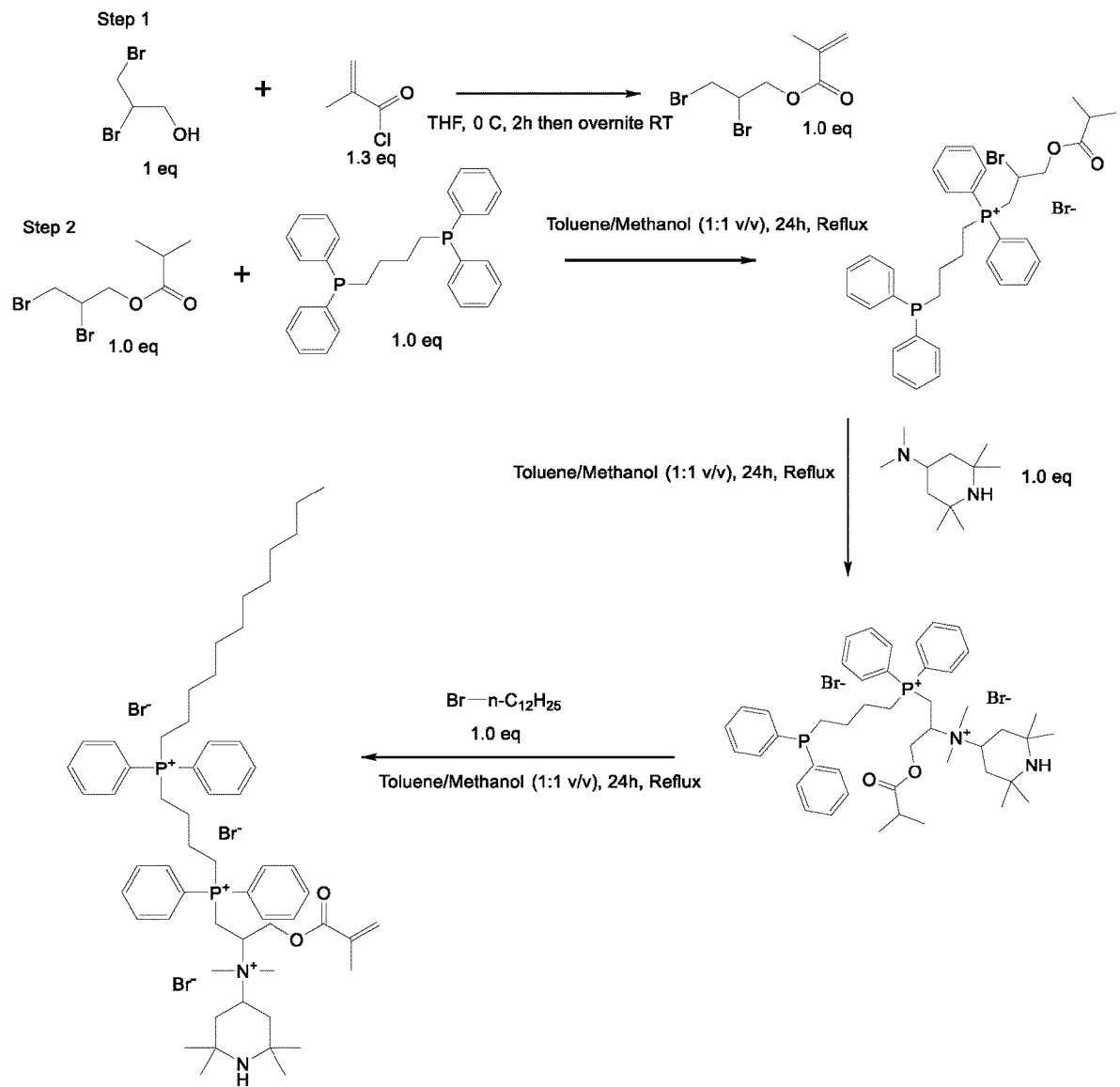
FIG. 15 is an example of a synthesis pathway for making a compound according to embodiments of the present disclosure.
Figure 16:
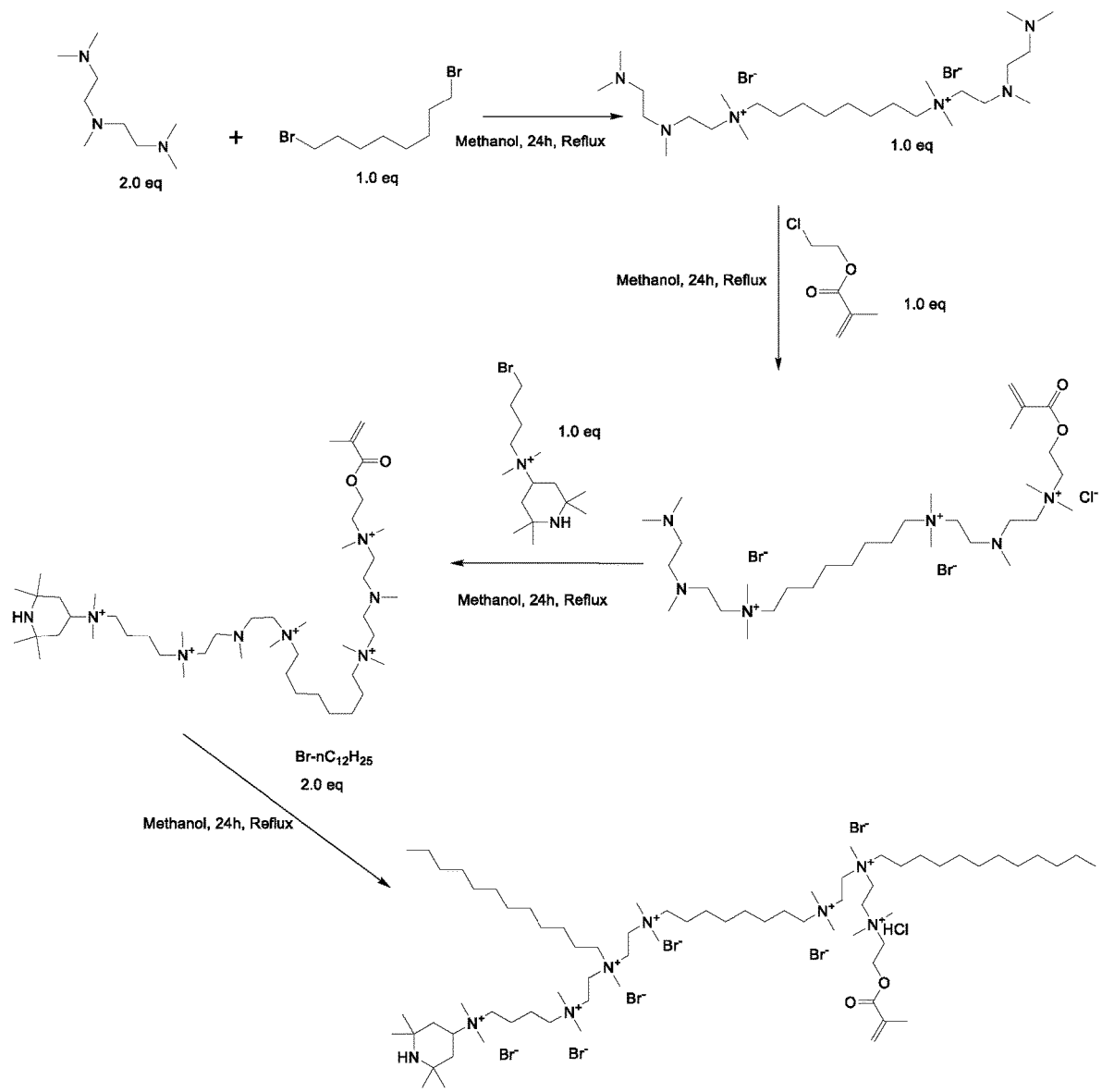
FIG. 16 is an example of a synthesis pathway for making a compound according to embodiments of the present disclosure.
Figure 17:
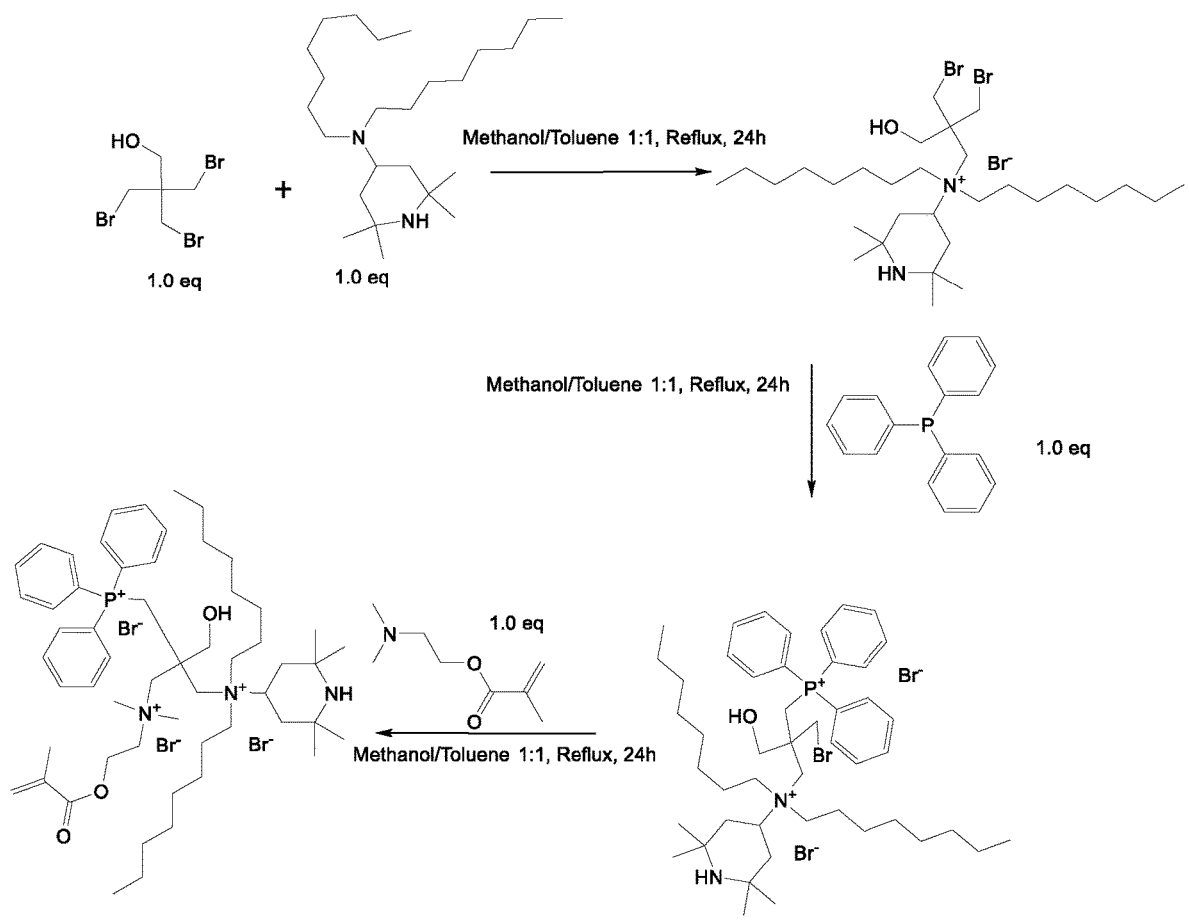
FIG. 17 is an example of a synthesis pathway for making a compound according to embodiments of the present disclosure.
Figure 18:
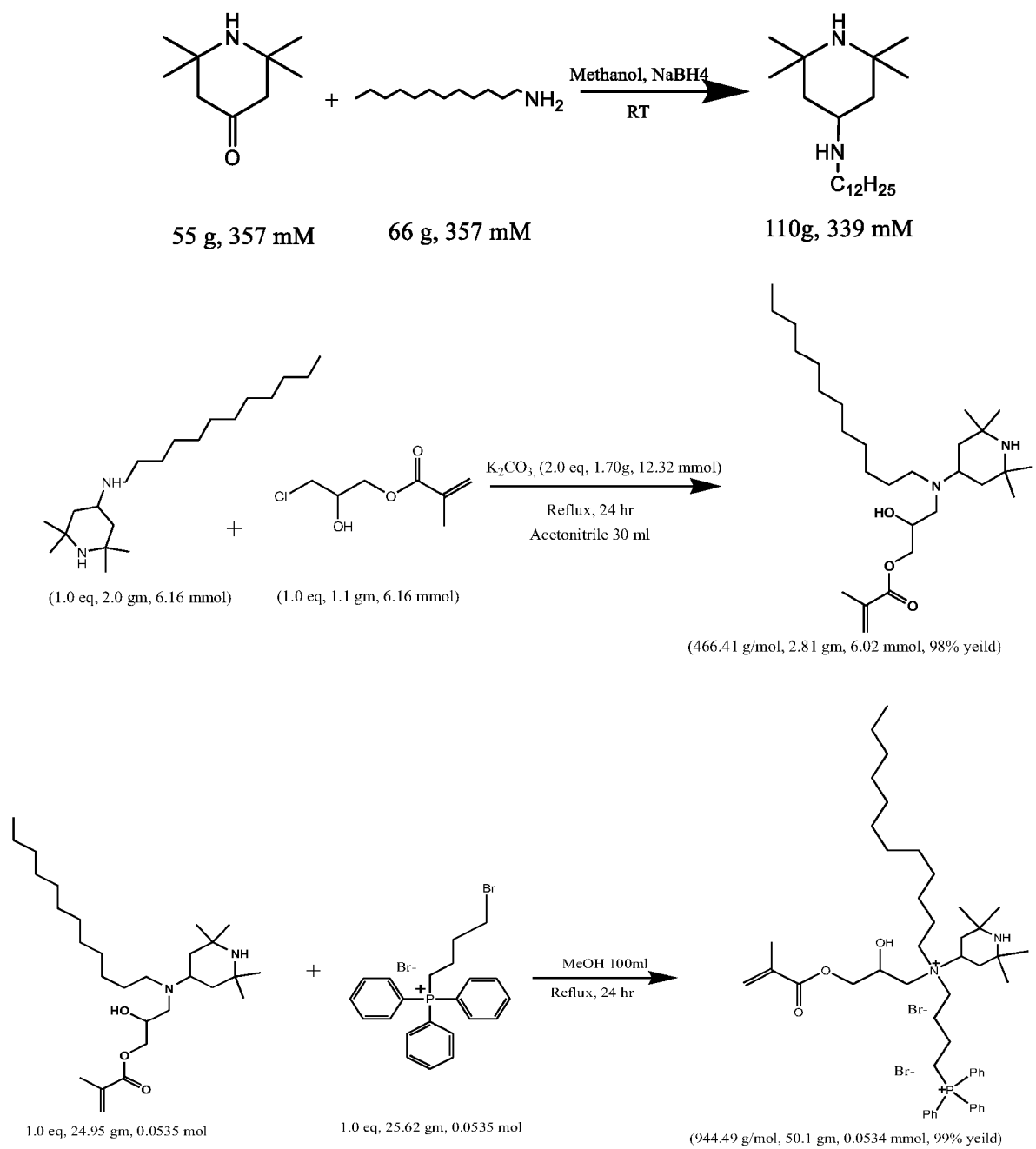
FIG. 18 is an example of a synthesis pathway for making a compound according to embodiments of the present disclosure.
Figure 19:
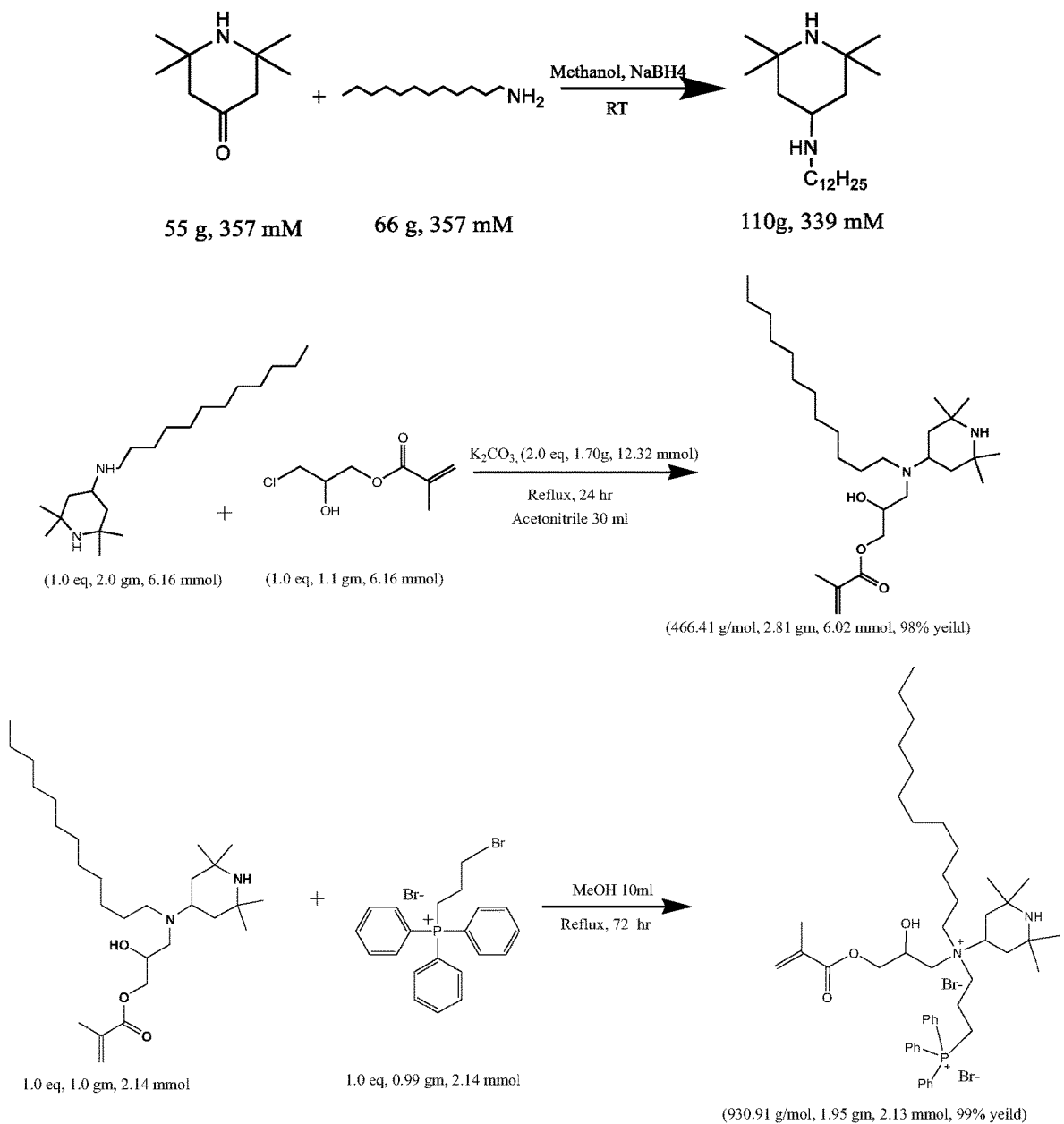
FIG. 19 is an example of a synthesis pathway for making a compound according to embodiments of the present disclosure.
Figure 20:
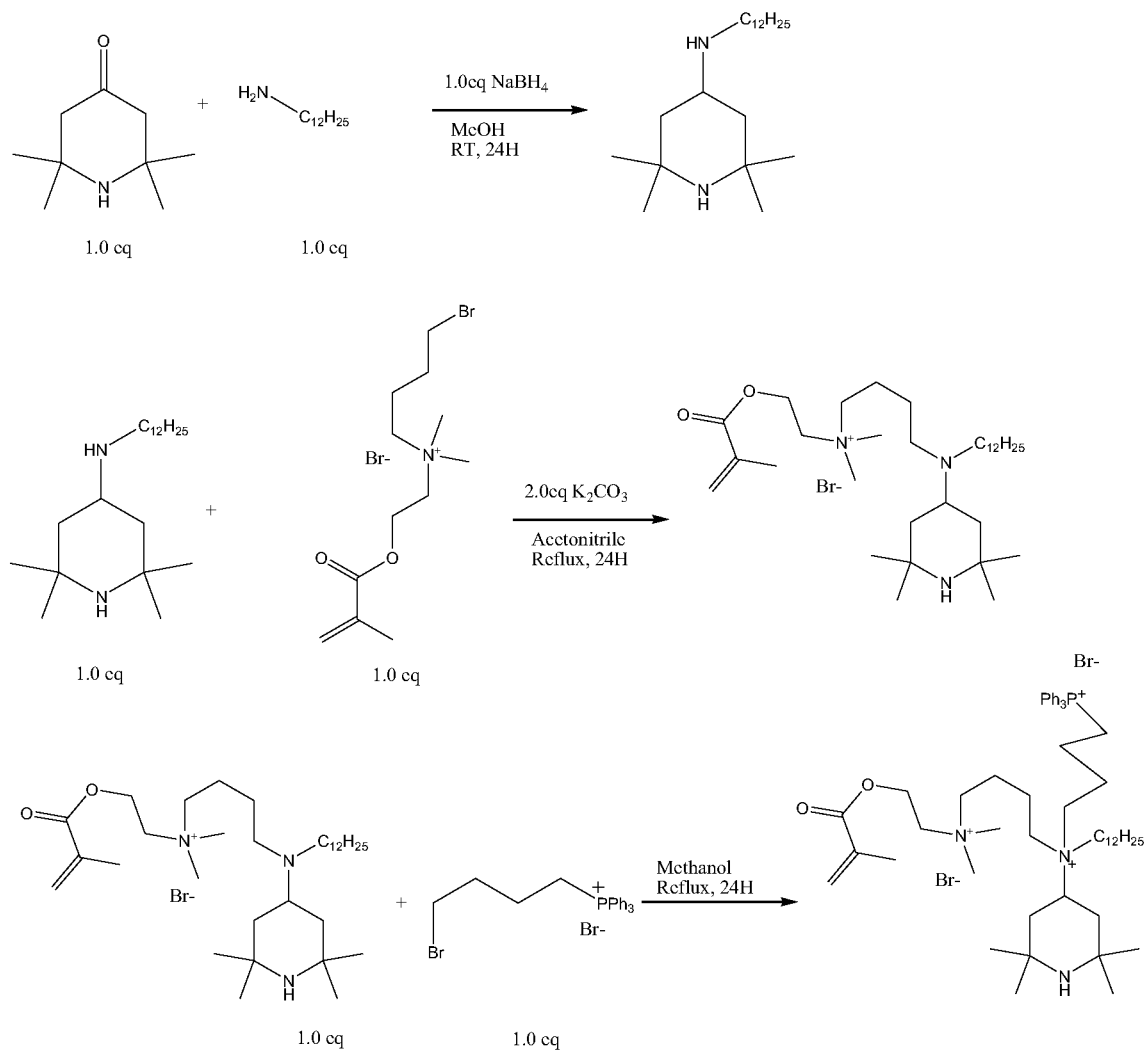
FIG. 20 is an example of a synthesis pathway for making a compound according to embodiments of the present disclosure.
Figure 21:
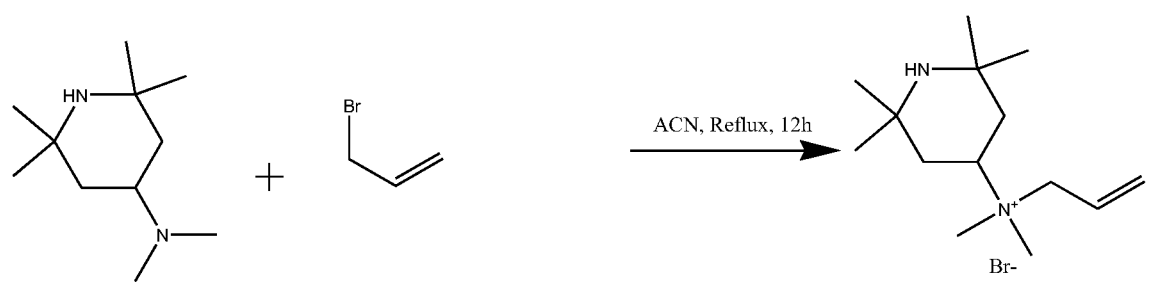
FIG. 21 is an example of a synthesis pathway for making a compound according to embodiments of the present disclosure.
Figure 22:
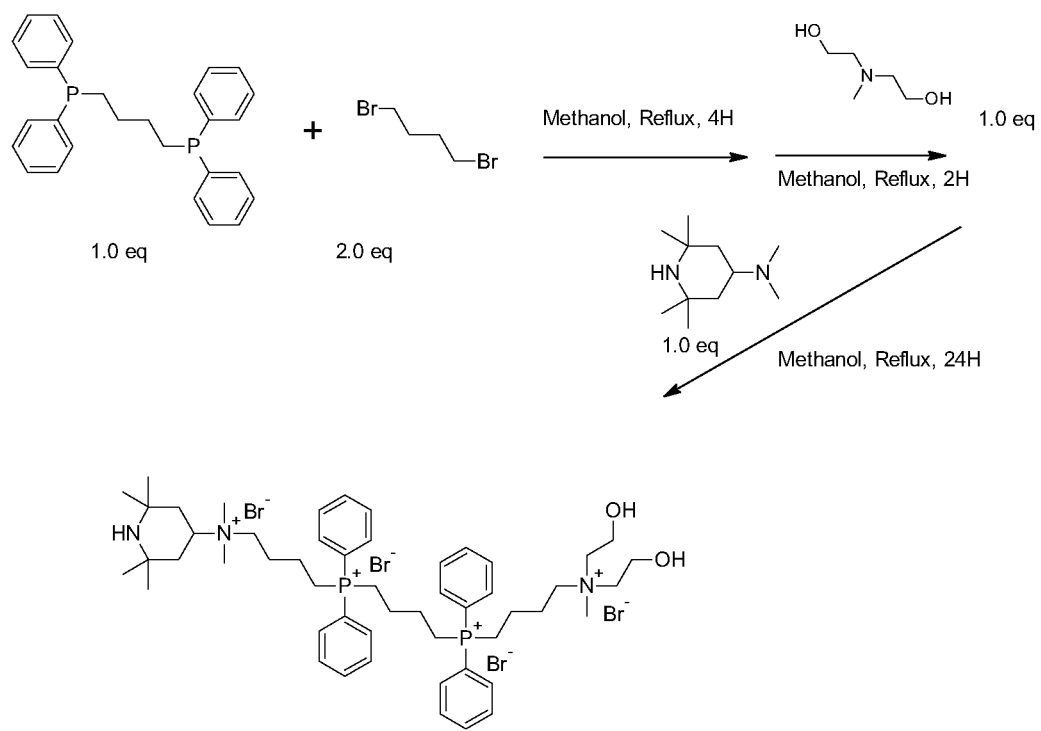
FIG. 22 is an example of a synthesis pathway for making a compound according to embodiments of the present disclosure.
Figure 23:
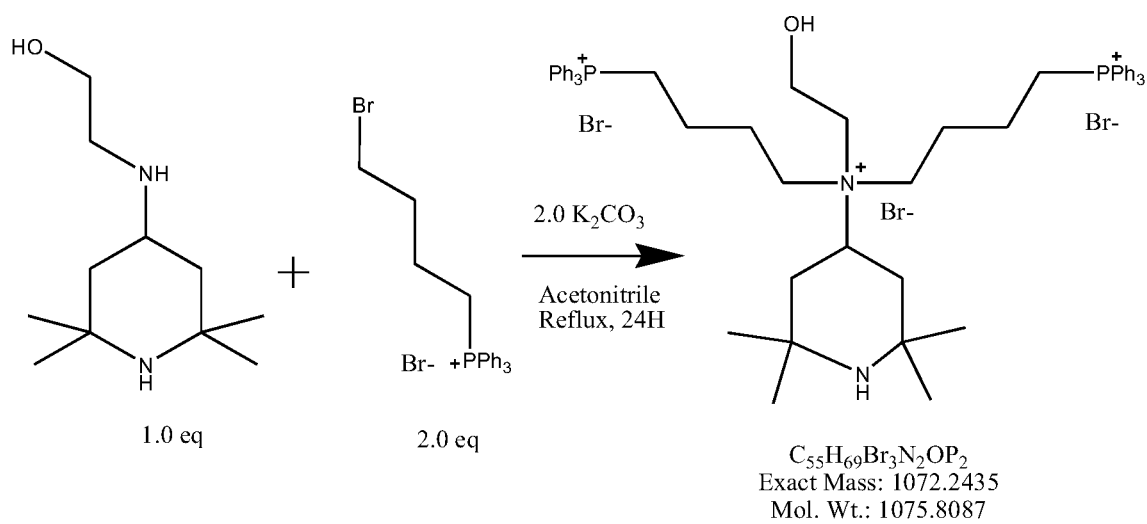
FIG. 23 is an example of a synthesis pathway for making a compound according to embodiments of the present disclosure.
Figure 24:
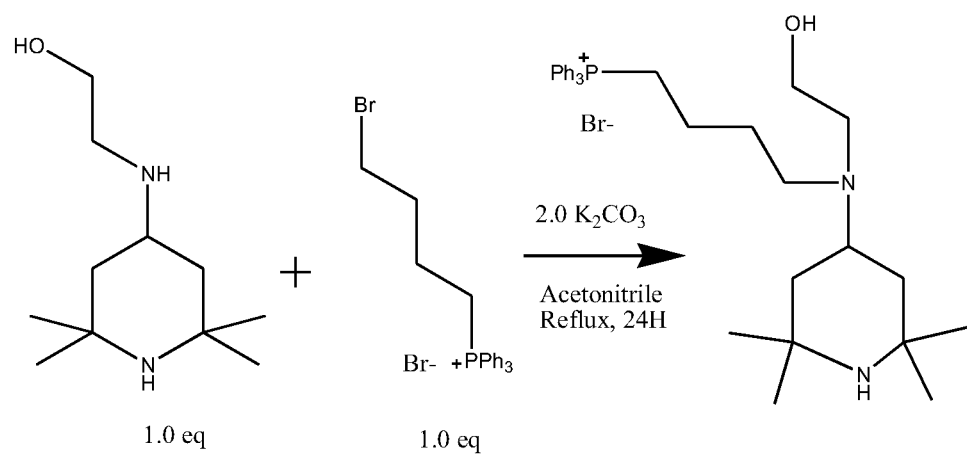
FIG. 24 is an example of a synthesis pathway for making a compound according to embodiments of the present disclosure.

Embodiments of the present disclosure relate to compounds that have two or more functional groups, where the functional groups may be selected from a group consisting of at least one N-halamine precursor, at least one cationic center, at least one coating incorporation group (CIG), at least one lipophilic moiety or combinations thereof. The compounds may have biocidal activity and the compounds may subsequently be chemically modified to enhance or provide biocidal activity. The chemical modification may be performed in situ and repeated once or multiple times to extend the time-frame over which the compounds have the desired biocidal activity. The functional groups may be physically separated from one another by other atoms within the compound and this physical separation may provide a desired compound-stability and influence the compound's biocidal activity.

Some embodiments of the present disclosure relate to polymerizable compounds that comprise at least one N-halamine precursor, at least one cationic center, at least one CIG and at least one lipophilic moiety. The polymerizable compounds may generally comprise at least one hydrophobic portion and at least one hydrophilic portion. The hydrophobic portion can also be referred to as a non-polar portion or a lipophilic portion. The hydrophilic portion can also be referred to as a polar portion or a lipophobic portion. Together the hydrophobic portion and the hydrophilic portion of the compounds may provide the compounds with one or more surfactant-like properties.

The at least one CIG may incorporate the compound into a coating or the at least one CIG may incorporate the coating onto a surface of a substrate, or the CIG may perform both functions. For example, the CIG may link or cure or tether or polymerize the polymerizable compound. The CIG may allow the polymerizable compound to be incorporated into a polymer, including incorporation into a polymer backbone, within various different polymers by different synthesis methods. The different polymers may be synthesized through various synthesis methods, including but not limited to: condensation polymerization; addition polymerization; step-growth polymerization; radical polymerization; chain-growth polymerization; latex emulsion polymer synthesis or any combination of these or other polymerization methods through concurrent or subsequent polymer processing or polymerization processes.

Definitions

Unless defined otherwise, all technical and scientific terms used herein have the same meaning as commonly understood by one of ordinary skill in the art to which this disclosure belongs.

As used herein, the term "about" refers to an approximately +/− 10% variation from a given value. It is to be understood that such a variation is always included in any given value provided herein, whether or not it is specifically referred to.

As used herein, the term "activity" refers to biocidal activity that kills, inhibits the growth of or otherwise renders a microbe harmless.

The terms "biocide" as used herein means a chemical compound, a chemical composition or a chemical formulation, such as a disinfectant, that has biocidal activity and can kill or render harmless one or more microbes.

The term "formulation" refers to the chemical components of a recipe that is used to make a polymer and/or a coating that comprises one or more polymers, such as a latex coating.

The terms "halo" or "halogen" by themselves or as part of another substituent, as used herein, have the same meaning as commonly understood by one of ordinary skill in the art, and refer to chlorine, bromine or iodine.

The term "latex" as used herein means an emulsion of a first liquid in which polymer particles are dispersed. The polymer particles may also be referred to as polymer colloid and/or polymer sol. The term "latex" may also be referred to herein as a polymer dispersion.

The term "liquid" as used herein means an incompressible fluid that may be in the form of a bulk phase, a surface phase, a spray, a droplet, a micro droplet or a nano droplet.

As used herein, the terms "microbe" and "microbes" refer to one or more single celled, or multi-cellular, microorganisms exemplified by at least one of bacterium, archaea, yeast or fungi.

The term "N-halamine" as used herein refers to a compound containing one or more nitrogen-halogen covalent bonds that is normally formed by the halogenation of imide, amide or amine groups of a compound. The presence of the halogen on an N-halamine moiety may render the compound biocidal or enhance the compound's biocidal activity. N-halamines, as referred to in the present disclosure, include both cyclic, acyclic N-halamine compounds and may also be a reference to precursors of N-halamine compounds.

The term "polymerizable" as used herein refers to a property of a compound to be incorporated into a polymer through one or more chemical bonds between the compound and another chemical component of the polymer or another chemical component of a pre-polymer compound, such as a monomer. The polymer may be a homopolymer, a co-polymer or a heteropolymer. In some examples of the present disclosure the polymerizable compounds can act as monomers in a polymerization process wherein the monomers are linked, cured, tethered or polymerized into the chemical structure of a polymer. In some examples of the present disclosure the polymerizable property may arise due to the compound comprising one or more CIGs.

The terms "quaternary ammonium cation", "quaternary ammonium compound", "quaternary ammonium salt", "QAC", and "quat" may be used interchangeably throughout the present disclosure to refer to ammonium compounds in which four organic groups are linked to a nitrogen atom that produces a positively charged ion (cation) of the structure $NR_4^+$.

Embodiments of the present disclosure will now be described by reference to the figures, FIG. 1 to FIG. 42

Some embodiments of the present disclosure relate to polymerizable compounds that have surfactant-like properties, a cationic charge and biocidal activity, or the potential for increased biocidal activity. Some embodiments of the present disclosure relate to compounds with the following general-formula (Formula 1):

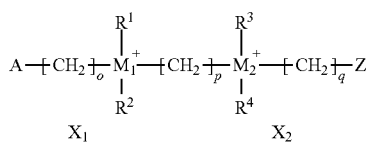

(1)

wherein,
A is an N-halamine precursor that may be selected from a group comprising imidazolidine-2,4-dione (hydantoin); 5,5-dimethylhydantoin; 4,4-dimethyl-2-oxazalidione; tetramethyl-2-imidazolidione; 2,2,5,5-tetramethylimidazo-lidin-4-one; a uracil derivative; and piperidine, including 2,2,6,6-tetramethyl-piperidine;
$M_1$ and $M_2$ are each independently selected from nitrogen, phosphorous or nil, but both$_{are}$ not nil;
$R_1$, $R_2$, $R_3$ and $R_4$ are each independently selected from a group consisting of: a linear alkyl group ($C_nH_{(2n+1)}$) where n is an integer between 0 and 18; a branched alkyl group ($C_mH_{(2m+1)}$) where m is an integer between 0 and 18; a phenyl group; a cyclohexyl group; a linear alkyloyl group: ($C_aH_{2a}OH$) where a is an integer between 0 and 18; and a branched alkyloyl group ($C_bH_2bOH$) where b is an integer between 0 and 18, wherein in $R_1$ and $R_2$ n, m, a and b are 0 when $M_1$ is nil, and wherein $R_3$ and $R_4$ n, m, a and b are 0 when $M_2$ is nil;
$X_1$ and $X_2$ are ions each independently selected from one of $Cl^-$, $Br^-$, $I^-$ and $PO_4^{3-}$; o, p and q are each an integer independently selected between 0 and 12; and Z is selected from a group comprising at least one of vinyl, vinyl derivative, methyl methacrylate, acrylate, styrene, vinyl benzyl, acrylamide, epoxy, —COOH, —CHO, —CN, —NCO, —NH2, —CNO, —SCN, —NCS and —OH.

Some of embodiments of the present disclosure relate to polymerizable compounds with the following general formula (Formula 2):

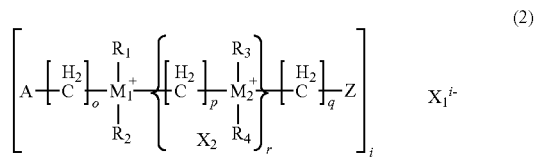

(2)

wherein,
A is an N-halamine precursor that may be selected from a group comprising imidazolidine-2,4-dione (hydantoin); 5,5-dimethylhydantoin; 4,4-dimethyl-2-oxazalidione; tetramethyl-2-imidazolidione; 2,2,5,5-tetramethylimidazo-lidin-4-one; a uracil derivative; piperidine and 2,2,6,6-tetramethyl-piperidine;
$M_1$ and $M_2$ are each independently selected from nitrogen, phosphorous or nil, but both are not nil;
$R_1$, $R_2$, $R_3$ and $R_4$ are each independently selected from a group consisting of: a linear alkyl group ($C_nH_{(2n+1)}$) where n is an integer between 0 and 18; a branched alkyl group ($C_mH_{(2m+1)}$) where m is an integer between 0 and 18; a phenyl group; a cyclohexyl group; a linear alkyloyl group: ($C_aH_{2a}OH$) where a is an integer between 0 and 18; or a branched alkyloyl group (CbH2bOH) where b is an integer between 0 and 18, wherein in $R_1$ and $R_2$ n, m, a and b are 0 when $M_1$ is nil, and wherein $R_3$ and $R_4$ n, m, a and b are 0 when $M_2$ is nil;
$X_1$ and $X_2$ are ions each independently selected from one of $Cl^-$, $Br^-$, $I^-$ and $PO_4^{3-}$;
o, p, q and r are each an integer independently selected between 0 and 12; and Z is selected from a group comprising at least one of vinyl, vinyl derivative, methyl methacrylate, acrylate, styrene, vinyl benzyl, acrylamide, epoxy, —COOH, —CHO, —CN, —NCO, —NH2, —CNO, —SCN, —NCS and —OH; and
i is an integer between 1 and 5.

Some of embodiments of the present disclosure relate to polymerizable compounds with the following general-formula (Formula 3):

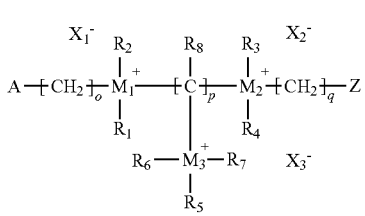

(3)

wherein,
A is an N-halamine precursor that may be selected from a group comprising imidazolidine-2,4-dione (hydantoin); 5,5-dimethylhydantoin; 4,4-dimethyl-2-oxazalidione; tetramethyl-2-imidazolidione; 2,2,5,5-tetramethylimidazo-lidin-4-one; a uracil derivative; and piperidine, including 2,2,6,6-tetramethyl-piperidine
$M_1$, $M_2$ and $M_3$ are each independently selected from nitrogen or phosphorous; $R_1$, $R_2$, $R_3$, $R_4$, $R_5$, $R^6$, $R^7$ and $R^8$ are each independently selected from: a linear alkyl group ($C_nH_{2n+1}$) where n is an integer between 0 and 18; a phenyl group; a cyclohexane group; or an alkyloyl group $(C_mH_{2m}OH)$ where m is an integer between 0 and 18;

$X_1^-$, $X_2^-$ and $X_3^-$ are ions each independently selected from but not limited to $Cl^-$, $Br^-$, $I^-$ or $PO_4^{3-}$;

o, p and q are each an integer independently selected between 0 and 12; and Z is selected from a group comprising at least one of vinyl, vinyl derivative, methyl methacrylate, acrylate, styrene, vinyl benzyl, acrylamide, epoxy, —COOH, —CHO, —CN, —NCO, —NH2, —CNO, —SCN, —NCS and —OH.

Some of embodiments of the present disclosure relate to polymerizable compounds with the following general-formula (Formula 4):

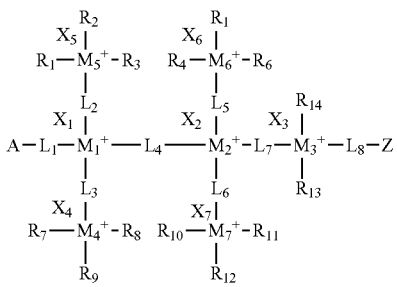

(4)

wherein,

A is an N-halamine precursor that may be selected from a group comprising imidazolidine-2,4-dione (hydantoin); 5,5-dimethylhydantoin; 4,4-dimethyl-2-oxazalidione; tetramethyl-2-imidazolidione; 2,2,5,5-tetramethylimidazo-lidin-4-one; a uracil derivative; piperidine and 2,2,6,6-tetramethyl-piperidine;

$M_1$, $M_2$, $M_3$, $M_4$, $M_5$, $M_6$ and $M_7$ are each independently selected from nitrogen, phosphorous or nil, wherein not all are nil;

$R_1$, $R_2$, $R_3$, $R_4$, $R_5$, $R_6$, $R_7$, $R_8$, $R_9$, $R_{10}$, $R_{11}$, $R_{12}$, Ria and Ria are each independently selected from a linear alkyl group $(C_nH_{2n+1})$ where n is an integer between 0 and 18; a branched alkyl group $(C_mH_{(2m+1)})$ where m is an integer between 0 and 18; a phenyl group; a cyclohexyl group; a linear alkyloyl group $(C_aH_{2a}OH)$ where a is an integer between 0 and 18; and a branched alkyloyl group $(C_bH_{2b}OH)$ where b is an integer between 0 and 18, wherein in $R_1$, $R_2$ and $R_3$ n, m, a and b are 0 when $M_5$ is nil, wherein in $R_4$, $R_5$ and $R_6$ n, m, a and b are 0 when $M_6$ is nil; wherein in $R_7$, $R_8$ and $R_9$ n, m, a and b are 0 when Ma is nil, wherein in $R_{10}$, $R_{11}$ and $R_{12}$ n, m, a and b are 0 when $M_7$ is nil, and wherein in $R_{13}$ and $R_{14}$ n, m, a and b are 0 when $M_3$ is nil;

$X_1$, $X_2$, $X_3$, $X_4$, $X_5$, $X_6$ and $X_7$ are ions each independently selected from one of $Cl^-$, $Br^-$, $I^-$ and $PO_4^{3-}$;

$L_1$, $L_2$, $L_3$, $L_5$, $L_6$ and La are each selected from nil, linear alkylene $(C_dH_{(2d+1)})$ where d is an integer between 0 and 18; a branched alkylene $(C_eH_{(e+1)})$ where e is an integer between 0 and 18; a linear alkylol $(C_fH_{2f}OH)$ where f is an integer between 0 and 18; or a branched alkylol $(C_gH_{2g-2}OH)$ where g is an integer between 0 and 18;

$L_4$ and $L_7$ are each selected from a linear alkylene $(C_dH_{(2d+1)})$ where d is an integer between 0 and 18; a branched alkylene $(C_eH_{(e+1)})$ where e is an integer between 0 and 18; a linear alkylol $(C_fH_{2f}OH)$ where f is an integer between 0 and 18; or a branched alkylol $(C_gH_{2g-2}OH)$ where g is an integer between 0 and 18;

Z is selected from at least one of vinyl, vinyl derivative, methyl methacrylate, acrylate, styrene, vinyl benzyl, acryl- amide, epoxy, —COOH, —CHO, —CN, —NCO, —NH2, —CNO, —SCN, —NCS or —OH.

Some of embodiments of the present disclosure relate to polymerizable compounds with the following general-formula (Formula 4A):

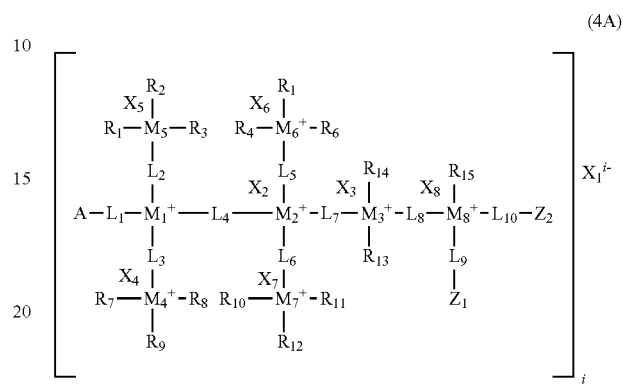

(4A)

wherein,

A is an N-halamine precursor that may be selected from a group comprising imidazolidine-2,4-dione (hydantoin); 5,5-dimethylhydantoin; 4,4-dimethyl-2-oxazalidione; tetramethyl-2-imidazolidione; 2,2,5,5-tetramethylimidazo-lidin-4-one; a uracil derivative; and piperidine, including 2,2,6,6-tetramethyl-piperidine $M_1$, $M_2$, $M_3$, $M_4$, $M_5$, $M_6$, $M_7$, and $M_8$ are each independently selected from nitrogen, phosphorous or nil;

$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{15}$ are each independently selected from a linear alkyl group $(C_nH_{(2n+1)})$; a branched alkyl group $(C_mH_{(2m+1)})$ where m is an integer between 0 and 18; a phenyl group; a cyclohexane group; a linear alkyloyl group $(C_aH_{2a}OH)$ where a is an integer between 0 and 18; and a branched alkyloyl group $(C_bH_{2b}OH)$ where b is an integer between 0 and 18;

$X_1$, $X_2$, $X_3$, $X_4$, $X_5$, $X_6$, $X_7$ and $X_8$ are each independently selected from but not limited to $Cl^-$, $Br^-$, $I^-$ or $PO_4^{3-}$;

L1, L2, L3, L5, L6, L8, L9 and L10 are each independently selected from nil, a linear alkyl $(CdH(2d+1))$ where b is an integer between 0 and 18; a branched alkyl $(CeH(2e-1))$ where e is an integer between 0 and 18; a linear alkylol $(CfH2fOH)$ where f is an integer between 0 and 18; or a branched alkylol $(CgH2gOH)$ where g is an integer between 0 and 18; i is an integer selected between 1 and 5; and Z1 and Z2 are each independently selected from at least one of vinyl, vinyl derivative, methyl methacrylate, acrylate, styrene, vinyl benzyl, acrylamide, epoxy, —COOH, —CHO, —CN, —NCO, —NH2, —CNO, —SCN, —NCS, —OH or nil.

One embodiment of the present disclosure relates to a polymerizable compound that may be referred to herein as PIP-C10-C3-methyl, methyl, acrylamide, or PIP-C10-C3-MMAcryl and that has the following formula (Formula 5):

(5)

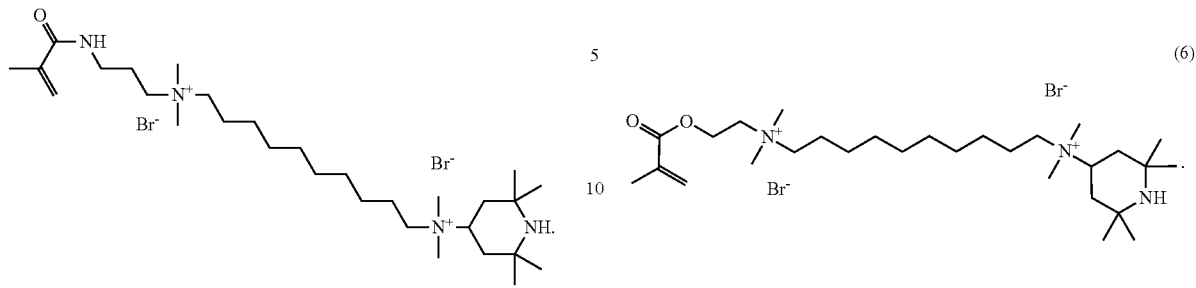

Another embodiment of the present disclosure relates to a polymerizable compound that may be referred to herein as PIP-C10-C2-methyl, methyl, acrylamide, or PIP-C10-C2-MMA and that has the following formula (Formula 6):

(6)

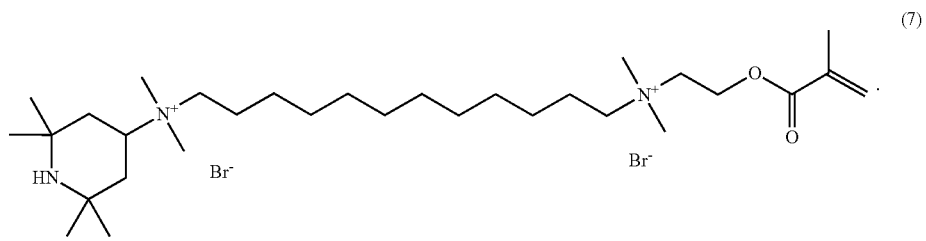 [SMILES: C=C(C)C(=O)OCC[N+](C)(C)CCCCCCCCCCCC[N+](C)(C)C1CC(C)(C)NC(C)(C)C1 ; [Br-] ; [Br-]]

Another embodiment of the present disclosure relates to a polymerizable compound that may be referred to herein as PIP-C12-C2-methyl, methyl, acrylamide, or PIP-C10-C2-MMA and that has the following formula (Formula 7):

(7)

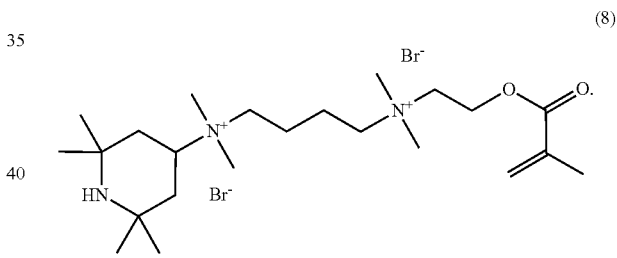

Another embodiment of the present disclosure relates to a polymerizable compound that may be referred to herein as PIP-C4-methyl, methyl, acrylamide, or PIP-C4-MMA and that has the following formula (Formula 8):

(8)

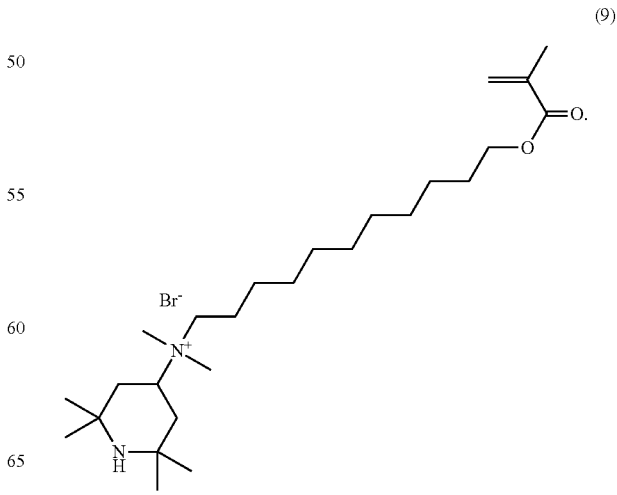

Another embodiment of the present disclosure relates to a polymerizable compound that may be referred to herein as PIP-C11-methyl, methyl, acrylamide, or PIP-C11-MMA and that has the following formula (Formula 9):

(9)

Another embodiment of the present disclosure relates to a polymerizable compound that may be referred to herein as PIP-C11-methyl, methyl, acrylamide-phosphate, or PIP-C11-MMA-phosphate and that has the following formula (Formula 10):

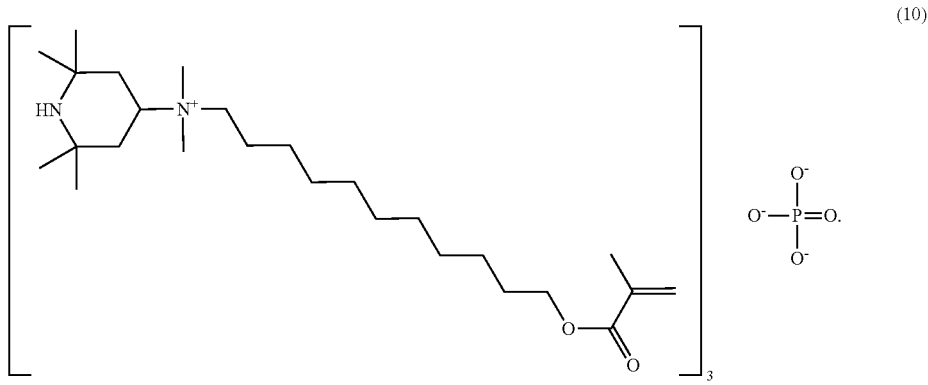

Another embodiment of the present disclosure relates to a polymerizable compound that may be referred to herein as PIP-C4-PPh-C4-PPh-benzyl vinyl and that has the following formula (Formula 11):

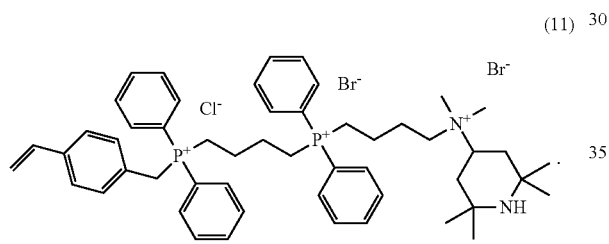

Another embodiment of the present disclosure relates to a polymerizable compound that may be referred to herein as PIP-C4-P-C3-P-benzyl vinyl and that has the following formula (Formula 12):

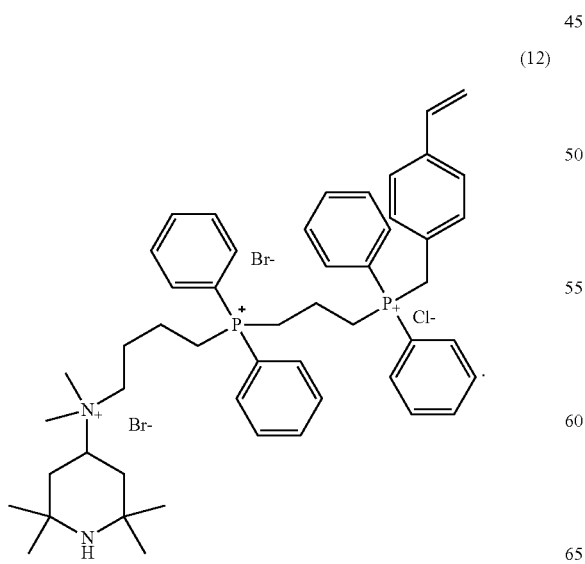

Another embodiment of the present disclosure relates to a polymerizable compound that may be referred to herein as PIP-C4-P-C4-P-C11-MMA and that has the following formula (Formula 13):
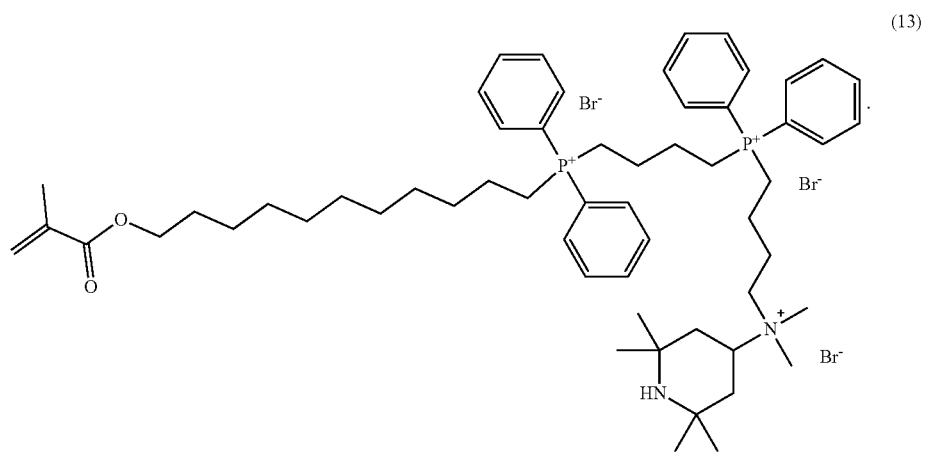 [SMILES: C=C(C)C(=O)OCCCCCCCCCCC[P+](CCCC[P+](CCCC[N+](C)(C)C1CC(C)(C)NC(C)(C)C1)(c1ccccc1)c1ccccc1)(c1ccccc1)c1ccccc1 ; [Br-] ; [Br-] ; [Br-]]
Another embodiment of the present disclosure relates to a polymerizable compound that may be referred to herein as PIP-C12-C3-MMA and that has the following formula (Formula 14):
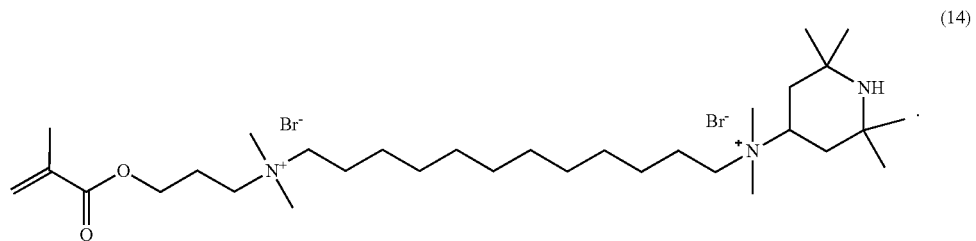 [SMILES: C=C(C)C(=O)OCCC[N+](C)(C)CCCCCCCCCCCC[N+](C)(C)C1CC(C)(C)NC(C)(C)C1 ; [Br-] ; [Br-]]

Another embodiment of the present disclosure relates to a polymerizable compound that may be referred to herein as PIP-P-C4-P-C12-C3-MMA and that has the following formula (Formula 15):
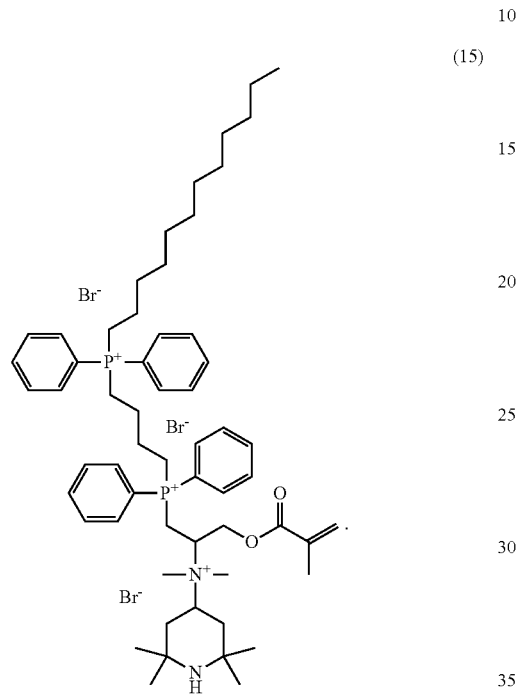
(15)
Another embodiment of the present disclosure relates to a polymerizable compound that may be referred to herein as PIP-C4-C2-12-C2-8-2-MMA-C2-12 and that has the following formula (Formula 16):
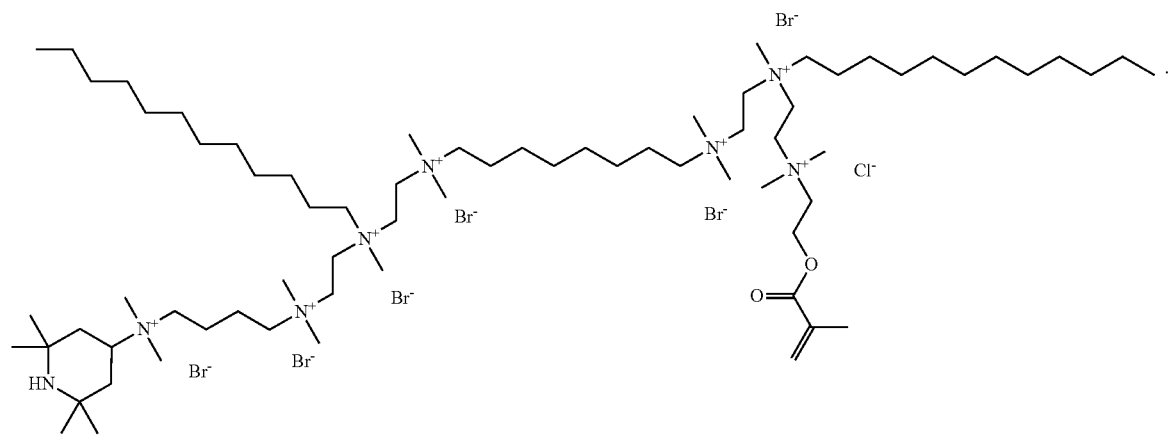
(16)

Another embodiment of the present disclosure relates to a polymerizable compound that may be referred to herein as PIP-C3-OH-P-C2-MMA and that has the following formula (Formula 17):

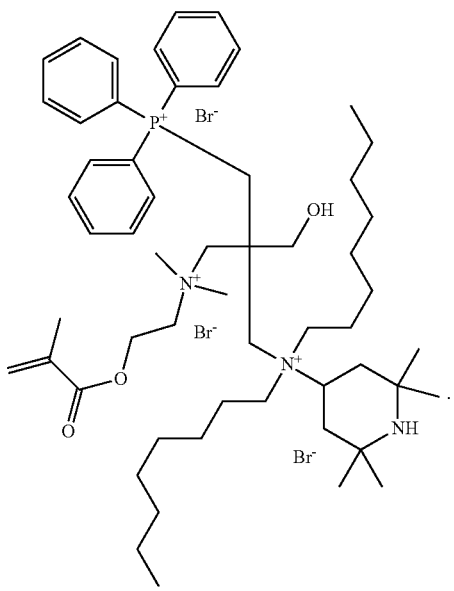

(17)

Another embodiment of the present disclosure relates to a polymerizable compound that may be referred to herein as PIP-C12-C4-triphenyl phosphate or PIP-C12-C4-TPP and that has the following formula (Formula 18):

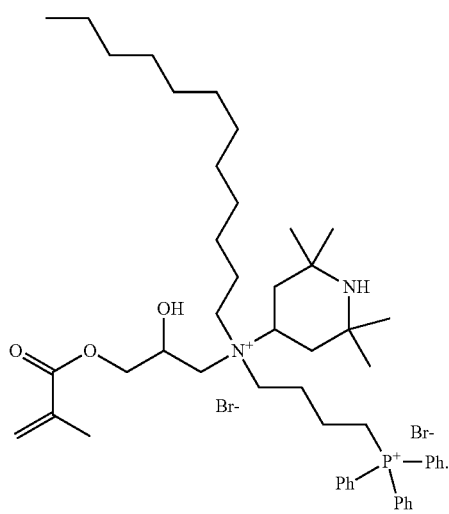

(18)

Another embodiment of the present disclosure relates to a polymerizable compound that

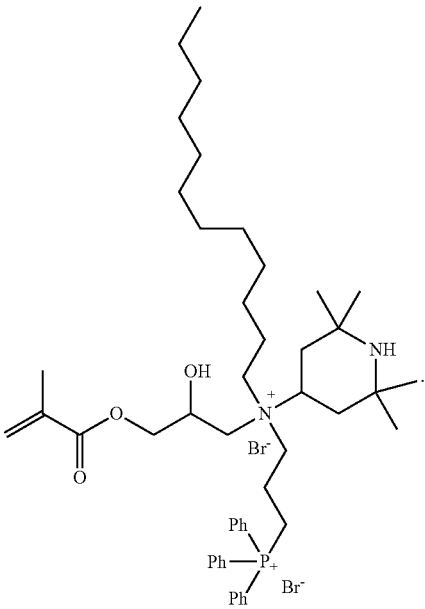

(19)

may be referred to herein as PIP-C12-C3-TPP and that has the following formula (Formula 19):

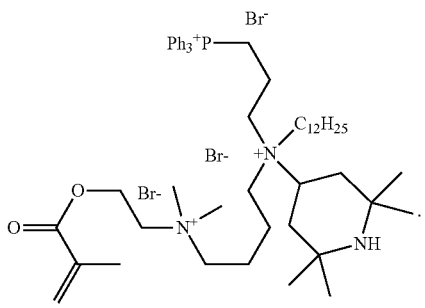

(20)

Another embodiment of the present disclosure relates to a polymerizable compound that may be referred to herein as PIP-C1-vinyl and that has the following formula (Formula 21):

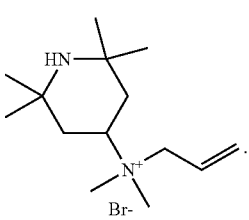

(21)

Another embodiment of the present disclosure relates to a polymerizable compound that may be referred to herein as PIP-C1-vinyl and that has the following formula (Formula 22):

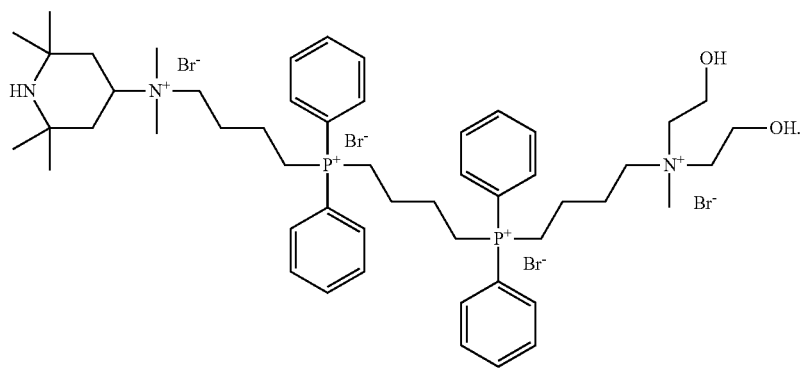

(22)

Another embodiment of the present disclosure relates to a polymerizable compound that may be referred to herein as Di-phos hydroxyl and that has the following formula (Formula 23):

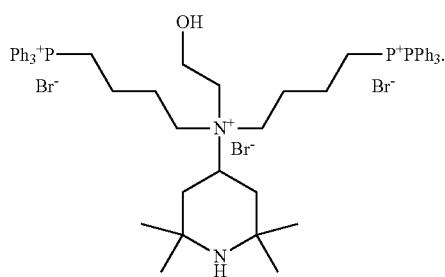

(23)

Another embodiment of the present disclosure relates to a polymerizable compound that may be referred to herein as PIP-C2-OH-C4-TPP and that has the following formula (Formula 24):

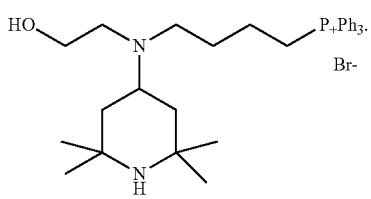

(24)

Some embodiments of the present disclosure relate to polymer coatings that incorporate one or more of the polymerizable compounds of Formula 1 through Formula 24 above. The polymer coatings can be used to coat substrates that have hard surfaces and/or soft surfaces. Some examples of suitable hard surfaces include, but are not limited to: glass, ceramic, metal, wood and polymers. Some examples of suitable soft surfaces include, but are not limited to: natural textiles, synthetic textiles and combinations thereof.

FIG. 5 through FIG. 24 show examples of synthetic pathways for making one or more polymerizable compounds according to the present disclosure.

EXAMPLES

Example 1—Experimental Data

Compounds of Formula 5, Formula 6, Formula 7 and Formula 8 were subjected to various experiments to demonstrate the compounds have surfactant-like properties and biocidal activity and/or the potential for increased biocidal activity.

Table 1 provides a summary of the compounds that were tested by the various experiments, described herein further below.

TABLE 1

Summary of the compounds tested

| Formula | Compound | Abbreviation | Molecular Weight (g/mol) |
|---|---|---|---|
| Acrylic latex synthesis | | | |
| 5 | PIP-C10-C3-MMA | M1 | 654.52 |
| 6 | PIP-C10-C2-MMA | M3 | 641.60 |
| 7 | PIP-C12-C2-MMA | M6 | 503.59 |
| 8 | PIP-C4-MMA | M5 | 979.33 |
| 9 | PIP-C11-MMA | M2 | 503.59 |
| 10 | PIP-C11-MMA-Phosphate | MP | |
| 11 | PIP-C4-PPh-C4-PPh-Benzyl Vinyl | PB | 979.33 |
| 12 | PIP-C4-P-C3-P-Benzyl Vinyl | PV | 965.3 |
| 13 | PIP-C4-P-C4-P-C11-MMA | PM | 1145.98 |
| 18 | PIP-C12-C4-TTP | ETI-CEM-1 | 944.54 |
| 19 | PIP-C12-C3-TTP | ETI-CEM-2 | 930.91 |
| 20 | PIP-C12-C4-TTP-NO hydroxyl group | ETI-CEM-3 | 1095 |

TABLE 1-continued

Summary of the compounds tested

| Formula | Compound | Abbreviation | Molecular Weight (g/mol) |
|---|---|---|---|
| Polyol Synthesis | | | |
| 21 | PIP-C1-Vinyl | none | 305.3 |
| Polyurethane Formulation | | | |
| 22 | Diol QAS-QPS | D2 | 1161.78 |
| 23 | Di-phos hydroxyl | D3 | 1075.81 |
| 24 | | D4 | 597.61 |

Surface Tension Measurements

Compounds of Formula 5, Formula 6 and Formula 9 were subjected to surface tension experiments to assess any surfactant-like properties.

A KRUSS K100 Tensiometer was used to determine the surface tension of a sample of the compounds in liquid water at different concentrations. The concentrations tested were 0.5%, 1.0%, 3.0%, 5.0% and 10%. A platinum plate with dimensions of about 19.9 mm×about 0.2 mm×about 10 mm (width, thickness and height respectfully) was attached to a sensitive mass balance. The sample was raised to the fixed platinum plate at a rate of 10 mm/min with a detection sensitivity of 0.005 g until the liquid sample reached the bottom of the plate. The plate was then immersed in the liquid sample at a depth of 2 mm for 60-150 seconds and any change in mass was recorded by the equipment as a function of time. Force was determined using the equation f=ma.

The surface tension ($\gamma$) of each liquid sample was calculated from the force measurement (f) using the equation outlined in Method C: Surface Tension by Wilhelmy plate, ASTM D1331-14.

$$\gamma = \frac{f}{2(l+t)} \cdot \cos\theta$$

where (l) is the length and (t) is the thickness of the plate. The contact angle was assumed to be 0. The test results describe a trend and general indication of the surfactant properties of each compound tested.

Table 2 below summarizes the experimental CMC data obtained using the compound of Formula 5 following a 60 second measurement.

TABLE 2

A summary of Formula 5 experimental surface tension data.

| Concentration | | 0.5% | 1.0% | 3.0% | 5.0% | 10.0% |
|---|---|---|---|---|---|---|
| Surface Tension (mN/m) | Mean | 36.93 | 32.55 | 31.23 | 30.28 | 29.57 |
| | Standard Deviation | 0.271 | 0.802 | 0.697 | 0.201 | 0.856 |

Table 3 below summarizes the experimental surface tension data obtained using the compound of Formula 6 following a 150 second measurement.

TABLE 3

A summary of Formula 6 experimental surface tension data.

| Concentration | | 0.5% | 1.0% | 3.0% | 5.0% | 10.0% |
|---|---|---|---|---|---|---|
| Surface Tension (mN/m) | Mean | 47.18 | 39.51 | 36.93 | 35.50 | 36.39 |
| | Standard Deviation | 1.69 | 0.45 | 0.30 | 0.17 | 0.15 |

Table 4 below summarizes the experimental surface tension data obtained using the compound of Formula 9 following a 150 second measurement.

TABLE 4

A summary of Formula 9 experimental surface tension data.

| Concentration | | 0.5% | 1.0% | 3.0% | 5.0% | 10.0% |
|---|---|---|---|---|---|---|
| Surface Tension (mN/m) | Mean | 37.16 | 36.19 | 35.80 | 35.84 | 30.44 |
| | Standard Deviation | 0.21 | 0.08 | 0.04 | 0.05 | 0.45 |

Each of the compounds tested demonstrated surfactant-like properties as evidenced by the surface tension values that were measured as compared to water which is about 72 mN/m.

Example 2—Coating Formulations

Each of the compounds with Formula 5-13 and Formula 18-20 were used to make a polymer coating formulation by a latex-emulsion polymerization process. All coating formulations included a mixture of n-butyl acrylate and methyl methacrylate as major constituents of the polymer backbone, with which each of the compounds of Formula 5-13 and Formula 18-20 were mixed and emulsified.

Briefly, water and a non-ionic surfactant were placed in a multi-neck glass reactor equipped with a water bath, condenser, nitrogen line, an overhead stirrer, and an anchor type agitator. The temperature was raised to about 70° C. before about 2% of a pre-emulsion of monomers was added. The pre-emulsion of monomers comprises a mixture of MMA and BA monomers, non-ionic surfactant and water. This mixture was emulsified by high speed agitation to form a stable "pre-emulsion". A cationic radical seed-2,2'-Azobis (2-methylpropionamidine)dihydrochloride added at 0.2 wt % in total was next added which immediately turned the dispersion blue, indicating the beginning of polymerization and formation of seed particles. Monomer emulsion and initiator feeding was then carried out over a period of about 3 hours, after which the temperature was raised to about 75° C. at which the latex emulsion was held for about 1 hour before cooling the latex down to about 50° C. Chasers were then added at 50° C., with tert-butyl hydrogen peroxide at 0.1 wt % added as a shot and mixed-in for 15 minutes, while BRUGGOLITE® FF6M (BRUGGOLITE is a registered trademark of L. BRUGGEMANN KG) at 0.1 wt % was fed-in gradually over 30 minutes. When the chasers were added the latex was cooled down to about 30° C. and an oil-based antifoam agent (Rhodoline 646) at 0.2 wt % was added before filtering the latex through a 150 μm filter. Final pH was recorded. Level of coagulum for all coating formulations was less than 0.1%.

Tables 5, 6, 7, 8A, 8B and 9 below summarize acrylic latex coating formulations and the components of the coating formulations made according to embodiments of the present disclosure.

TABLE 5

Summary of examples of acrylic coating formulations.

| Formulation | Surfactant Type | Compound | Compound % |
|---|---|---|---|
| F1-Control | Cationic | None | 0.0% |
| F1-M1-5% | Cationic | Formula 5 | 5.0% |
| F1-M1-10% | Cationic | Formula 5 | 10.0% |
| F2-Control | Non-Ionic | None | 0.0% |
| F2-M1-4.6% | Non-Ionic | Formula 5 | 4.6% |
| F3-Control | Non-Ionic | None | 0.0% |
| F3-M1-4.6% | Non-Ionic | Formula 5 | 4.6% |
| F3-M1-10% | Non-Ionic | Formula 5 | 10.0% |
| F3-M2-5% | Non-Ionic | Formula 9 | 5.1% |
| F3-M3-6% | Non-Ionic | Formula 6 | 5.7% |
| F3-M3-11% | Non-Ionic | Formula 6 | 11.6% |
| F3-M5-5% | Non-Ionic | Formula 8 | 4.8% |
| F3-M6-6% | Non-Ionic | Formula 7 | 6.0% |
| F3-MP-4.6% | Non-Ionic | Formula 10 | 4.6% |
| F3-MP-10% | Non-Ionic | Formula 10 | 10.1% |
| F3-PB-4.6% | Non-Ionic | Formula 11 | 4.6% |
| F3-PB-10% | Non-Ionic | Formula 11 | 10.1% |
| F3-PV-9% | Non-Ionic | Formula 12 | 8.7% |
| F3-PM-4.6% | Non-Ionic | Formula 13 | 4.6% |
| F4-Control | Non-Ionic | None | 0.0% |
| F4-M6-6% | Non-Ionic | Formula 7 | 6.0% |
| F4-CEM1-13% | Non-Ionic | Formula 18 | 12.8% |
| F4-CEM2-13% | Non-Ionic | Formula 19 | 12.5% |
| F4-CEM3-10% | Non-Ionic | Formula 20 | 9.8% |

TABLE 6

Summary of the components of variants of Formulation F1.

| Formulation Component | F1-Control | F1-M1-5% | F1-M1-10% |
|---|---|---|---|
| Water | 58.2 | 56.0 | 53.7 |
| n-butyl acrylate | 17.0 | 17.0 | 17.0 |
| Methyl methacrylate | 22.5 | 22.5 | 22.5 |
| Cationic surfactant | 1.7 | 1.7 | 1.7 |
| Non-ionic surfactant | 0 | 0 | 0 |
| Polymerizable surfactant | 0 | 2.2 | 4.5 |
| Initiator | 0.2 | 0.2 | 0.2 |
| Reducing agent | 0.1 | 0.1 | 0.1 |
| Oxidizing agent | 0.1 | 0.1 | 0.1 |
| Antifoam | 0.2 | 0.2 | 0.2 |
| Total mass (grams) | 100 | 100 | 100 |

TABLE 7

Summary of the components of variants of Formulation F2.

| Formulation Component | F2-Control | F2-M1-4.6% |
|---|---|---|
| Water | 52.48 | 50.48 |
| n-butyl acrylate | 22.6 | 22.6 |
| Methyl methacrylate | 21.0 | 21.0 |
| Cationic surfactant | 0 | 0 |
| Non-ionic surfactant | 3.7 | 3.7 |
| Polymerizable surfactant | 0 | 2.0 |
| Initiator | 0.2 | 0.2 |
| Reducing agent | 0 | 0 |
| Oxidizing agent | 0 | 0 |
| Antifoam | 0.02 | 0.02 |
| Total mass (grams) | 100 | 100 |

TABLE 8A

Summary of the components of variants of Formulation F3.

| Formulation Component | F3-Control | F3-M1-4.6% | F3-M1-10% | F3-M2-5% | F3-M3-6% | F3-M3-11% | F3-M5-5% |
|---|---|---|---|---|---|---|---|
| Water | 52.28 | 50.28 | 47.58 | 50.08 | 49.78 | 47.18 | 50.18 |
| Acetone | 0 | 0 | 0 | 0 | 0 | 0 | 0 |
| n-butyl acrylate | 22.6 | 22.6 | 22.6 | 22.6 | 22.6 | 22.6 | 22.6 |
| Methyl methacrylate | 21.0 | 21.0 | 21.0 | 21.0 | 21.0 | 21.0 | 21.0 |
| Cationic surfactant | 0 | 0 | 0 | 0 | 0 | 0 | 0 |
| Non-ionic surfactant | 3.7 | 3.7 | 3.7 | 3.7 | 3.7 | 3.7 | 3.7 |
| Polymerizable surfactant | 0 | 2.0 | 4.7 | 2.2 | 2.5 | 5.1 | 2.1 |
| Initiator | 0.2 | 0.2 | 0.2 | 0.2 | 0.2 | 0.2 | 0.2 |
| Reducing agent | 0.1 | 0.1 | 0.1 | 0.1 | 0.1 | 0.1 | 0.1 |
| Oxidizing agent | 0.1 | 0.1 | 0.1 | 0.1 | 0.1 | 0.1 | 0.1 |
| Antifoam | 0.02 | 0.02 | 0.02 | 0.02 | 0.02 | 0.02 | 0.02 |
| Total mass (grams) | 100 | 100 | 100 | 100 | 100 | 100 | 100 |

TABLE 8B

Summary of the components of variants of Formulation F3.

| Formulation Component | F3-M6-6% | F3-MP-4.6% | F3-MP-10% | F3-PB-4.6% | F3-PB-10% | F3-PV-9% | F3-PM-4.6% |
|---|---|---|---|---|---|---|---|
| Water | 49.68 | 50.28 | 47.88 | 49.58 | 47.08 | 47.78 | 49.98 |
| Acetone | 0 | 0 | 0 | 0.7 | 0.8 | 0.7 | 0.3 |
| n-butyl acrylate | 22.6 | 22.6 | 22.6 | 22.6 | 22.6 | 22.6 | 22.6 |
| Methyl methacrylate | 21.0 | 21.0 | 21.0 | 21.0 | 21.0 | 21.0 | 21.0 |
| Cationic surfactant | 0 | 0 | 0 | 0 | 0 | 0 | 0 |

TABLE 8B-continued

Summary of the components of variants of Formulation F3.

| Formulation Component | F3-M6-6% | F3-MP-4.6% | F3-MP-10% | F3-PB-4.6% | F3-PB-10% | F3-PV-9% | F3-PM-4.6% |
|---|---|---|---|---|---|---|---|
| Non-ionic surfactant | 3.7 | 3.7 | 3.7 | 3.7 | 3.7 | 3.7 | 3.7 |
| Polymerizable surfactant | 2.6 | 2.0 | 4.4 | 2.0 | 4.4 | 3.8 | 2.0 |
| Initiator | 0.2 | 0.2 | 0.2 | 0.2 | 0.2 | 0.2 | 0.2 |
| Reducing agent | 0.1 | 0.1 | 0.1 | 0.1 | 0.1 | 0.1 | 0.1 |
| Oxidizing agent | 0.1 | 0.1 | 0.1 | 0.1 | 0.1 | 0.1 | 0.1 |
| Antifoam | 0.02 | 0.02 | 0.02 | 0.02 | 0.02 | 0.02 | 0.02 |
| Total mass (grams) | 100 | 100 | 100 | 100 | 100 | 100 | 100 |

TABLE 9

Summary of the components of variants of Formulation F4.

| Formulation Component | F4-M6-6% | F4-CEM1-13% | F4-CEM2-13% | F4-CEM3-10% |
|---|---|---|---|---|
| Water | 51.18 | 47.48 | 47.58 | 48.03 |
| Acetone | 0 | 0.7 | 0.7 | 0.7 |
| n-butyl acrylate | 22.6 | 22.6 | 22.6 | 22.6 |
| Methyl methacrylate | 21.0 | 21.0 | 21.0 | 21.0 |
| Cationic surfactant | 0 | 0 | 0 | 0 |
| Non-ionic surfactant | 2.2 | 2.2 | 2.2 | 2.95 |
| Polymerizable surfactant | 2.6 | 5.6 | 5.5 | 4.3 |
| Initiator | 0.2 | 0.2 | 0.2 | 0.2 |
| Reducing agent | 0.1 | 0.1 | 0.1 | 0.1 |
| Oxidizing agent | 0.1 | 0.1 | 0.1 | 0.1 |
| Antifoam | 0.02 | 0.02 | 0.02 | 0.02 |
| Total mass (grams) | 100 | 100 | 100 | 100 |

Active Chlorine Quantification

Energy Dispersive X-ray (EDX) spectroscopy testing was performed on the following coating formulations: F3 control, unchlorinated (see FIG. 1), F3 control, chlorinated (see FIG. 2), F3-M1-4.6%, unchlorinated (see FIG. 3) and F3-M1-4.6%, chlorinated (see FIG. 4). The chlorinated samples were exposed to 200 ppm chlorine solutions for about 10 minutes.

The EDX was completed using an Octane Super Detector on a FEI Quanta 650 FEG scanning electron microscope. The software package used for analysis was TEAM™ available from EDAX.

Latex Particle Size Distribution

Analysis of the latex particle size distribution was conducted using a Malvern Nano ZS and size distribution report was provided by Intensity V2.1 software. Table 10 summarizes the latex particle size distribution.

TABLE 10

Summary of Latex Particle Size Distribution

| Formulation | Compound % | Z-Average nm (Pdi) |
|---|---|---|
| F1-M1-5% | 5.0% | 90.44 (.041) |
| F2-Control | 0.0% | 113.1 (.014) |
| F2-M1-4.6% | 4.6% | 132.0 (.127) |
| F3-Control | 0.0% | 116.4 (.026) |
| F3-M1-4.6% | 4.6% | 124.9 (.036) |
| F3-PB-10% | 10.0% | 92.30 (.026) |

Biocidal Activity Testing

Coating formulations were tested for biocidal activity in accordance with ISO 22196: Measurement of antibacterial activity on plastics and other non-porous surfaces. Briefly, the sample size was scaled down to 2.5 cm×2.5 cm and the test conditions included testing in phosphate buffered saline (PBS) or 5% fetal bovine serum (FBS). The samples were challenged with *E. coli* (ATCC 25922). An overnight culture of *E. coli* was diluted to $10^6$ colony forming units (CFU)/mL, and about 50 µL of the diluted bacterial was added onto a 2.5 cm×2.5 cm testing surface that was coated with one of the coating formulations. Per ISO 22196 protocol, a polyethylene terephthalate cover film (2 cm×2 cm) was applied overtop to ensure contact between the coating formulation and the bacteria. The test surfaces then incubated with the bacteria at room temperature for the reported contact times. At the end of each contact time 2.5 ml of neutralizer was added to allow counting of bacteria.

Table 11 summarizes the biocidal activity experimental data of F1 variants of the coating formulations with or without exposure to 200 ppm of chlorine for 10 minutes at a pH of 10.7 following exposure to *E. coli* in PBS.

TABLE 11

Summary of F1 coating formulation biocidal activity in PBS.

| Bacteria | | Sample ID | Log Reduction ($Log_{10}$) at Various Contact Times in PBS | | |
|---|---|---|---|---|---|
| | | | 30 min | 60 min | Full Log Reduction |
| Gram-negative | *E. coli* ATCC 25922 | Unchlorinated F1-Control | 4.73 | 4.73 | 4.73 |
| | | Unchlorinated F1-M1-5% | 4.73 | 4.73 | |
| | | Unchlorinated F1-M1-10% | 4.73 | 4.73 | |
| | | Chlorinated F1-Control | 4.73 | 4.73 | |
| | | Chlorinated F1-M1-5% | 4.73 | 4.73 | |
| | | Chlorinated F1-M1-10% | 4.73 | 4.73 | |

Without being bound by any particular theory, it is postulated that unchlorinated killing of microbes was due to the use of the cationic surfactant (C-TAB) in the latex synthesis steps, as shown in Table 6.

12 summarizes the biocidal activity experimental data of F2 variants of the coating formulations with or without exposure to 200 ppm of chlorine for 10 minutes at a pH of 7 following exposure to *E. coli* in PBS.

TABLE 12

Summary of F2 coating formulation biocidal activity in PBS.

| Bacteria | Sample ID | Log Reduction ($Log_{10}$) at Various Contact Times in PBS | | |
|---|---|---|---|---|
| | | 30 min | 60 min | Full Log Reduction |
| Gram-negative | *E. coli* ATCC 25922 | Unchlorinated F2-Control | / | 1.15 | 5.71 |
| | | Unchlorinated F2-M1-4.6% | / | 1.01 | |
| | | Chlorinated F2-Control | 1.03 | 2.35 | |
| | | Chlorinated F2-M1-4.6% | 5.71 | 5.71 | |

Table 13 summarizes the biocidal activity experimental data of F3 variants of the coating formulations with or without exposure to 200 ppm of chlorine for 10 minutes at a pH of 7 following exposure to *E. coli* in PBS.

TABLE 13

Summary of F3 coating formulation biocidal activity in PBS.

| Bacteria | Sample ID | Log Reduction (Log10) at Various Contact Times in PBS | | | |
|---|---|---|---|---|---|
| | | 10 min | 30 min | 60 min | Full Log Reduction |
| Gram-negative *E. coli* ATCC 25922 | Unchlorinated F3-Control | / | / | 0.15 | 4.76 |
| | Unchlorinated F3-M1-4.6% | / | / | 0.33 | |
| | Unchlorinated F3-M1-10% | / | / | 0.55 | 4.81 |
| | Unchlorinated F3-M2-5% | / | / | −0.06 | |
| | Unchlorinated F3-M3-6% | 0.47 | 0.56 | 0.61 | 4.98 |
| | Unchlorinated F3-M3-11% | 0.28 | 0.40 | 0.42 | |
| | Unchlorinated F3-M5-5% | 0.60 | 0.66 | 0.73 | |
| | Unchlorinated F3-M6-6% | 0.19 | 0.36 | 0.21 | 4.88 |
| | Unchlorinated F3-MP-4.6% | 0.00 | 0.00 | / | 5.98 |
| | Unchlorinated F3-PB-4.6% | 0.14 | .07 | / | 4.67 |
| | Unchlorinated F3-PB-10% | 0.72 | 0.96 | / | 4.93 |
| | Unchlorinated F3-PV-9% | 0.47 | 0.58 | 0.58 | 4.97 |
| | Unchlorinated F3-PM-4.6% | 0.15 | 0.15 | / | 4.67 |
| | Chlorinated F3-Control | 0.26 | 0.65 | 0.60 | 4.76 |
| | Chlorinated F3-C3-M1-4.6% | 4.76 | 4.76 | 4.76 | |
| | Chlorinated F3-C3-M1-10% | 4.81 | 4.81 | 4.81 | 4.81 |
| | Chlorinated F3-M2-5% | 4.81 | 4.81 | 4.81 | |
| | Chlorinated F3-M3-6% | 4.98 | 4.98 | 4.98 | 4.98 |
| | Chlorinated F3-M3-11% | 0.67 | 4.98 | 4.98 | |
| | Chlorinated F3-M5-5% | 4.98 | 4.98 | 4.98 | |
| | Chlorinated F3-M6-6% | 4.88 | 4.88 | 4.88 | 4.88 |
| | Chlorinated F3-MP-4.6% | 5.98 | 5.98 | / | 5.98 |
| | Chlorinated F3-PB-4.6% | 4.67 | 4.67 | / | 4.67 |
| | Chlorinated F3-PB-10% | 4.93 | 4.93 | / | 4.93 |
| | Chlorinated F3-PV-9% | 1.24 | 2.42 | 4.97 | 4.97 |
| | Chlorinated F3-PM-4.6% | 1.46 | 4.67 | / | 4.67 |

Table 14 summarizes the biocidal activity experimental data of F4 variants of the coating formulations with or without exposure to 200 ppm of chlorine for 10 minutes at a pH of 7 following exposure to *E. coli* in PBS.

TABLE 14

Summary of F4 coating formulation biocidal activity in PBS.

| Bacteria | Sample ID | Log Reduction (Log10) at Various Contact Times in PBS | | | |
|---|---|---|---|---|---|
| | | 10 min | 30 min | 60 min | Full Log Reduction |
| Gram-negative *E. coli* ATCC | Unchlorinated F4-M6-6% | / | / | 0.29 | 5.85 |
| | Unchlorinated F4-CEM1-13% | 0.55 | 1.99 | 1.04 | 4.54 |

TABLE 14-continued

Summary of F4 coating formulation biocidal activity in PBS.

| Bacteria | Sample ID | Log Reduction (Log10) at Various Contact Times in PBS | | | |
|---|---|---|---|---|---|
| | | 10 min | 30 min | 60 min | Full Log Reduction |
| 25922 | Unchlorinated F4-CEM2-13% | 4.54 | 4.54 | 4.54 | |
| | Unchlorinated F4-CEM3-10% | / | / | 4.82 | 4.82 |
| | Chlorinated F4-M6-6% | 0.53 | 1.50 | 5.85 | 5.85 |
| | Chlorinated F4-CEM1-13% | 4.54 | 4.54 | 4.54 | 4.54 |
| | Chlorinated F4-CEM2-13% | 4.54 | 4.54 | 4.54 | |
| | Chlorinated F4-CEM3-10% | 4.82 | 4.82 | 4.82 | 4.82 |

Without being bound by any particular theory, it is postulated that the unchlorinated killing of microbes shown in Table 14 is evidence of the CEM monomers leaching, or otherwise dissociating, from the polymer particles after synthesis of the latex.

Table 15 summarizes the biocidal activity experimental data of F2 and F3 variants of the coating formulations tested with or without exposure to 200 ppm of chlorine for 10 minutes at a pH of 7 following exposure to *E. coli* in 5% FBS.

TABLE 15

Summary of F2 and F3 coating formulation biocidal activity in 5% FBS.

| Bacteria | | Sample ID | Log Reduction (Log10) at Various Contact Times in 5% FBS | | | |
|---|---|---|---|---|---|---|
| | | | 10 min | 30 min | 60 min | Full Log Reduction |
| Gram-negative | *E. coli* ATCC 25922 | Unchlorinated F2-M1-4.6% | / | / | −0.17 | 4.89 |
| | | Unchlorinated F3-M1-4.6% | / | / | −0.09 | |
| | | Unchlorinated F3-M1-10% | / | / | −0.21 | |
| | | Unchlorinated F3-M2-5% | / | / | 0.01 | 4.90 |
| | | Unchlorinated F3-M3-6% | / | / | 0.42 | 4.99 |
| | | Unchlorinated F3-M5-5% | / | / | 0.32 | |
| | | Unchlorinated F3-M6-6% | / | / | 0.46 | 5.00 |
| | | Unchlorinated F3-MP-4.6% | / | / | 0.70 | 5.20 |
| | | Unchlorinated F3-PB-4.6% | 0.49 | 0.55 | 0.56 | 4.94 |
| | | Unchlorinated F3-PB-10% | 0.49 | 0.65 | 1.03 | |
| | | Unchlorinated F3-PM-4.6% | 0.54 | 0.58 | 0.45 | |
| | | Chlorinated F2-M1-4.6% | 0.64 | 1.93 | 4.89 | 4.89 |
| | | Chlorinated F3-C3-M1-4.6% | 0.82 | 4.89 | 4.89 | |
| | | Chlorinated F3-C3-M1-10% | 1.16 | 4.89 | 4.89 | |
| | | Chlorinated F3-M2-5% | 0.39 | 1.37 | 2.50 | 4.90 |
| | | Chlorinated F3-M3-6% | 0.20 | 0.67 | 1.72 | 4.99 |
| | | Chlorinated F3-M5-5% | 0.38 | 1.86 | 2.63 | |
| | | Chlorinated F3-M6-6% | 0.31 | 0.64 | 2.82 | 5.00 |
| | | Chlorinated F3-MP-4.6% | 0.63 | 0.88 | 1.84 | 5.20 |
| | | Chlorinated F3-PB-4.6% | 0.71 | 0.96 | 2.53 | 4.94 |
| | | Chlorinated F3-PB-10% | 4.94 | 4.94 | 4.94 | |
| | | Chlorinated F3-PM-4.6% | 0.47 | 0.45 | 0.54 | |

Table 16 summarizes the biocidal activity experimental data of F4 variants of the coating formulations tested with or without exposure to 200 ppm of chlorine for 10 minutes at a pH of 7 following exposure to *E. coli* in 5% FBS.

TABLE 16

Summary of F4 coating formulation biocidal activity in 5% FBS.

| Bacteria | | Sample ID | Log Reduction (Log10) at Various Contact Times in 5% FBS | | | |
|---|---|---|---|---|---|---|
| | | | 10 min | 30 min | 60 min | Full Log Reduction |
| Gram-negative | *E. coli* ATCC 25922 | Unchlorinated F4-CEM1-13% | 0.37 | 0.53 | 0.47 | 4.90 |
| | | Unchlorinated F4-CEM2-13% | 4.59 | 4.59 | 4.59 | 4.59 |
| | | Unchlorinated F4-CEM3-10% | / | 0.46 | 0.89 | 4.91 |
| | | Chlorinated F4-CEM1-13% | 0.31 | 0.57 | 0.75 | 4.90 |
| | | Chlorinated F4-CEM2-13% | 4.59 | 1.29 | 1.17 | 4.59 |
| | | Chlorinated F4-CEM3-10% | / | 0.48 | 0.65 | 4.91 |

Protein Adsorption Testing

Various of the coating formulations were tested for the relative protein adsorption into the surface of the coating formulations. These tests are based upon a Lowry/BCA assay kit to measure the concentration of eluted protein from the surface of the coating formulations. Table 17 summarizes the protein adsorption data obtained by these experiments using 5% FBS and *E. coli* exposure as described herein above.

TABLE 17

Summary of protein adsorption data.

| Sample ID | Protein per cm$^2$ µg/cm2 |
|---|---|
| F2-M1-4.6% | 2.01 ± 0.17 |
| F3-Control | 1.31 ± 0.36 |
| F3-M1-4.6% | 1.76 ± 0.57 |
| F3-M1-10% | 4.90 ± 0.20 |
| F3-M2-5% | 1.84 ± 0.16 |
| F3-PB-10% | 8.64 ± 0.10 |
| F4-M6-6% | 2.04 ± 0.04 |

Table 18 and Table 19 below summarize the formulations of polyol synthesis and the components of the polyol formulations made.

TABLE 18

Summary of polyol synthesis formulations.

| Formulation | Compound | Compound wt % | Compound mol % |
|---|---|---|---|
| C2-Control | None | 0.0% | 0.0% |
| C1-PB-7.8% | Formula 11 | 5.8% | 1.0% |
| C3-M1-4.5% | Formula 5 | 4.5% | 1.0% |
| C6- PIP-C1-Vinyl-3.75% | Formula 21 | 3.8% | 2.0% |

TABLE 19

Summary of the components of variants of 5L batch of polyol synthesis of Formulation C1, C3 and C6 (in grams).

| Formulation Component | C2-Control | C1-PB-5.8% | C3-M1-4.5% | C6-PIP-C1-Vinyl-3.8% |
|---|---|---|---|---|
| Polymerizable monomer | 0 | 206 | 138 | 154 |
| mixture of acrylate and styrenic monomers | 2000-3000 | 2000-3000 | 2000-3000 | 2000-3000 |
| Initiator | 100-200 | 100-200 | 100-200 | 100-200 |
| Solvent | 400-600 | 400-600 | 400-600 | 400-600 |
| Co-Solvent | 200-300 | 200-300 | 100-200 | 200-300 |

Table 20, Table 21 and Table 22 below summarize the polyurethane coating formulations and the components of the coating formulations made.

TABLE 20

Summary of polyurethane coating formulations.

| Formulation | Polyol | Compound | Compound wt % |
|---|---|---|---|
| C2NAP0 | C2-Control | None | 0.0% |
| C2D2P9 | C2-Control | Formula 22 | 5.4% |
| C2D3P17 | C2-Control | Formula 23 | 9.6% |
| C2D4P15 | C2-Control | Formula 24 | 8.3% |
| C2D4P22 | C2-Control | Formula 24 | 12.4% |
| C2M6P14 | C2-Control | Formula 7 | 8.6% |
| C6NAP0 | C6-PIP-C1-Vinyl-3.75% | None | 0.0% |
| C6D3P16 | C6-PIP-C1-Vinyl-3.75% | Formula 23 | 8.8% |
| C6D3P24 | C6-PIP-C1-Vinyl-3.75% | Formula 23 | 13.6% |

TABLE 21

Summary of the components of variants of polyurethane coating formulations with C2-Control polyol.

| Formulation Component | C2NAP0 | C2D2P9 | C2D3P17 | C2D4P15 | C2D4P22 | C2M6P14 |
|---|---|---|---|---|---|---|
| Polyol (C2) | 80 | 75 | 75 | 72 | 68 | 72 |
| Polymerizable monomer | 0 | 7.5 | 15 | 12.62 | 19.05 | 12.12 |
| Solvent | 4 | 10 | 20 | 20 | 20 | 10.80 |
| Co-solvent | 4 | 0 | 0 | 0 | 0 | 0 |
| Isocyanate | 45.38 | 46.56 | 46.56 | 46.56 | 46.56 | 46.56 |
| Catalyst | 0.16 | 0.16 | 0.16 | 0.16 | 0.16 | 0.16 |
| Total mass (grams) | 133.54 | 139.22 | 156.72 | 151.34 | 153.77 | 141.64 |

TABLE 22

Summary of the components of variants of polyurethane coating formulations with C6-PIP-C1-Vinyl-3.8% polyol.

| Formulation Component | C6NAP0 | C6D3P16 | C6D3P24 |
|---|---|---|---|
| Polyol (C6) | 80 | 75 | 72 |
| Polymerizable monomer | 0 | 14.29 | 22.86 |
| Solvent | 26 | 26 | 26 |
| Co-solvent | 0 | 0 | 0 |
| Isocyanate | 46.56 | 46.56 | 46.56 |
| Catalyst | 0.16 | 0.16 | 0.16 |
| Total mass (grams) | 152.72 | 162.01 | 167.58 |

Biocidal Activity Testing

Coating formulations were tested for biocidal activity in accordance with ISO 22196: Measurement of antibacterial activity on plastics and other non-porous surfaces. Briefly, the sample size was scaled down to 2.5 cm×2.5 cm and the test conditions included testing in PBS or 5% FBS. The samples were challenged with *E. coli* 0157. An overnight culture of *E. coli* was diluted to 106 colony forming units (CFU)/mL, and about 50 µL of the diluted bacterial was added onto a 2.5 cm×2.5 cm testing surface that was coated with one of the coating formulations. Per ISO 22196 protocol, a polyethylene terephthalate cover film (2 cm×2 cm) was applied overtop to ensure contact between the coating formulation and the bacteria. The test surfaces then incubated with the bacteria at room temperature for reported contact times. At the end of each contact time 2.5 ml of neutralizer was added to allow counting of bacteria.

Table 23 summarizes the biocidal activity experimental data of F1 variants of the coating formulations tested with or without exposure to 200 ppm of chlorine for 10 minutes at a pH of 7 following exposure to E. coli in 5% FBS.

TABLE 23

Summary of all the polyurethane coating formulations biocidal activity in 5% FBS.
Log Reduction (Log10) at Various Contact Times in 5% FBS

| 60 min | 120 min | 180 min | Full Log Reduction |
|---|---|---|---|
| / | / | 0.02 | 4.70 |
| / | / | 0.70 | 4.70 |
| −0.08 | 0.03 | 0.16 | 4.76 |
| 1.35 | 4.76 | 4.76 | 4.76 |

Humidity and UV Resistance Testing

Figure 25:
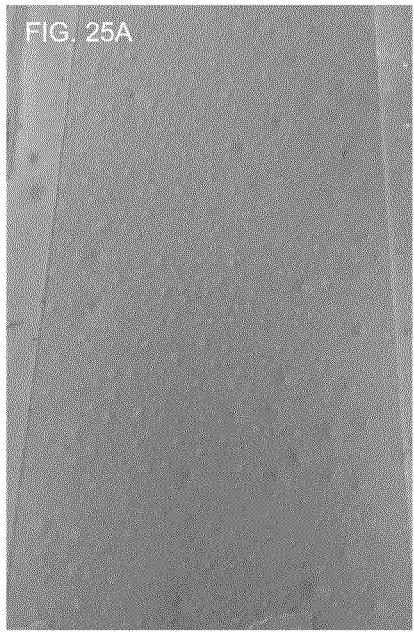
Figure 25:
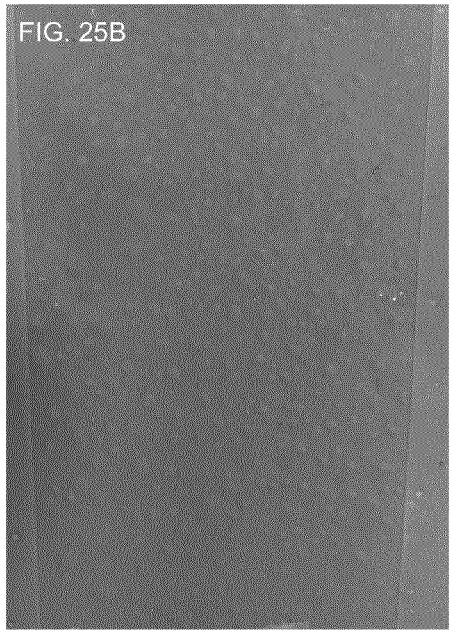
Figure 25:
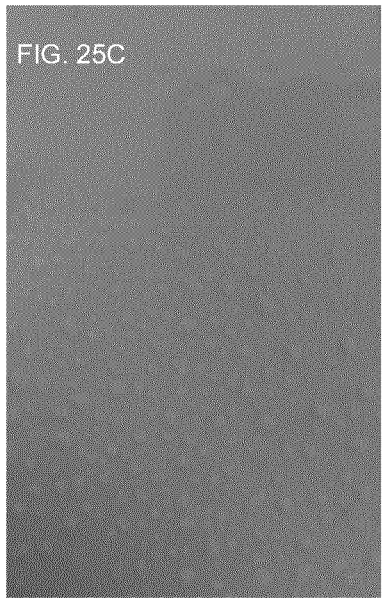
Figure 26:
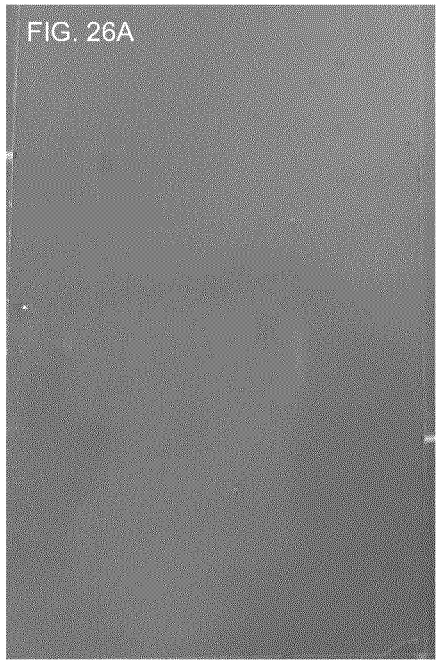
Figure 26:
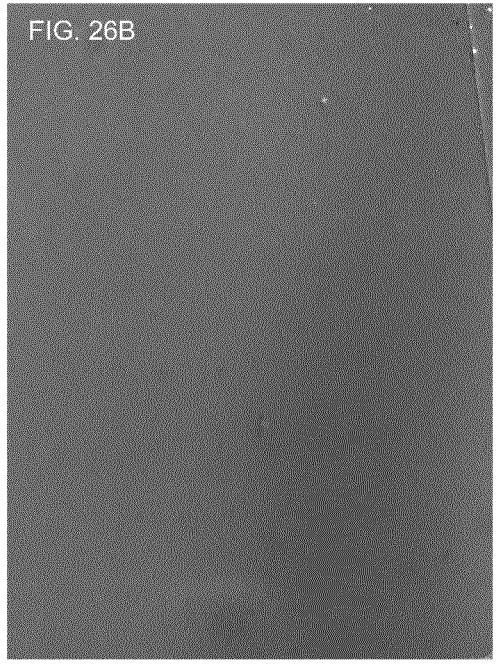
Figure 26:
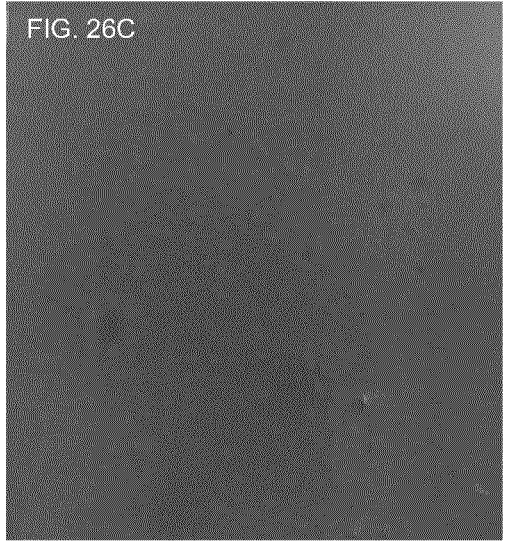
Figure 27:
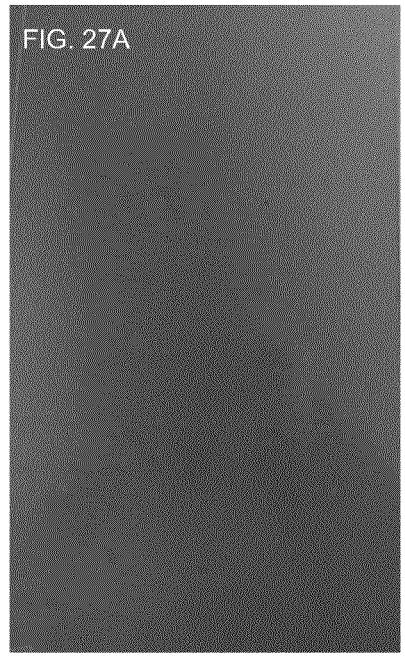
Figure 27:
Figure 27:
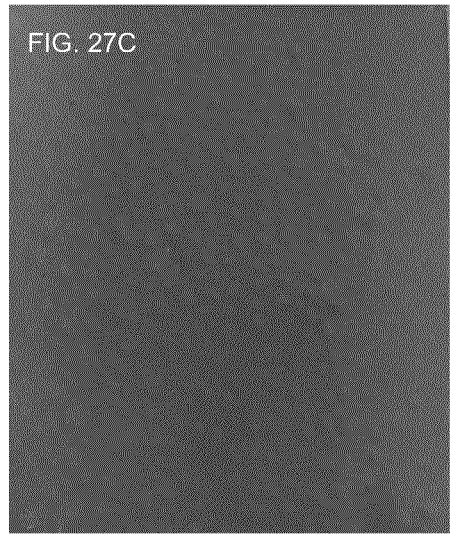
Figure 28:
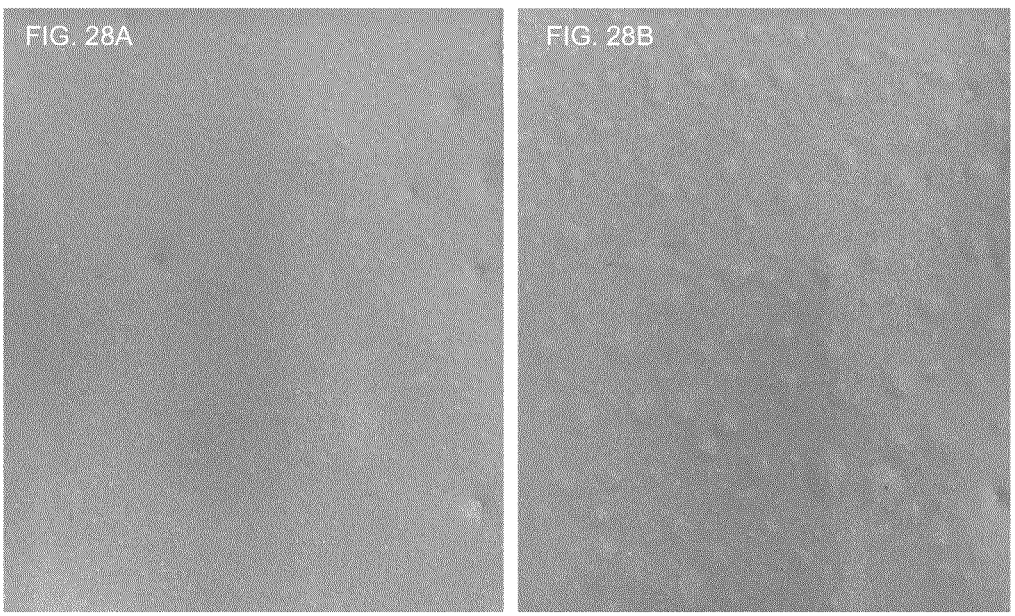
Figure 29:
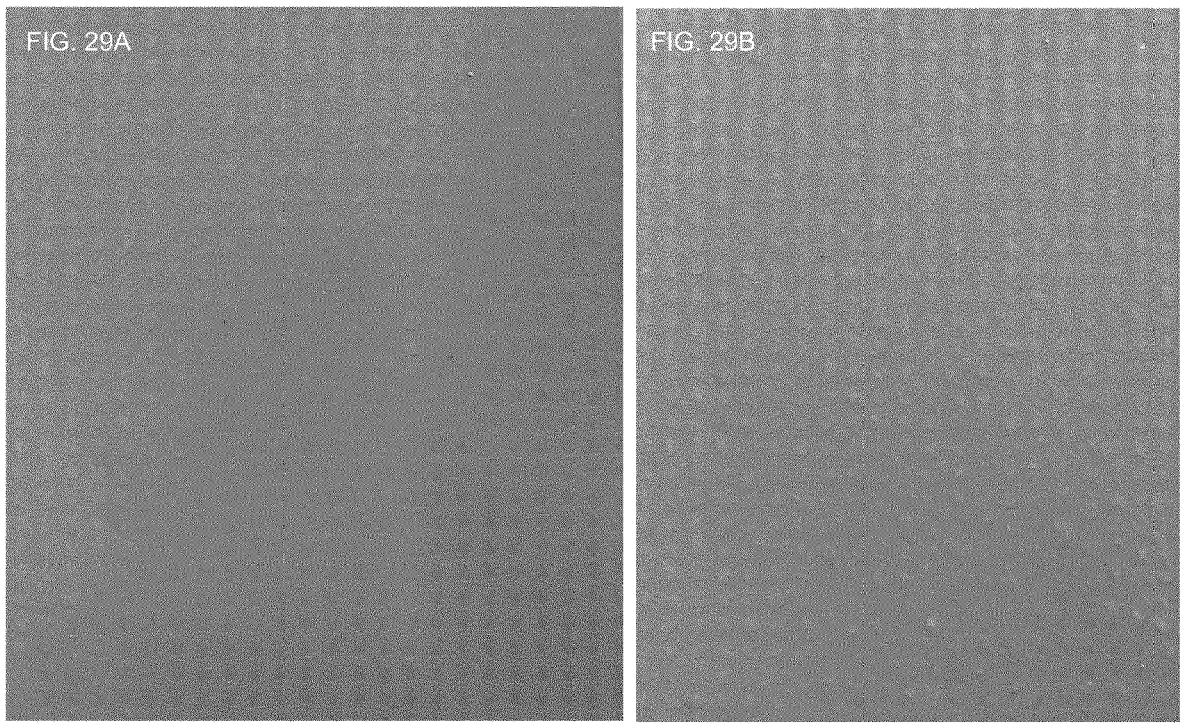
Figure 30:
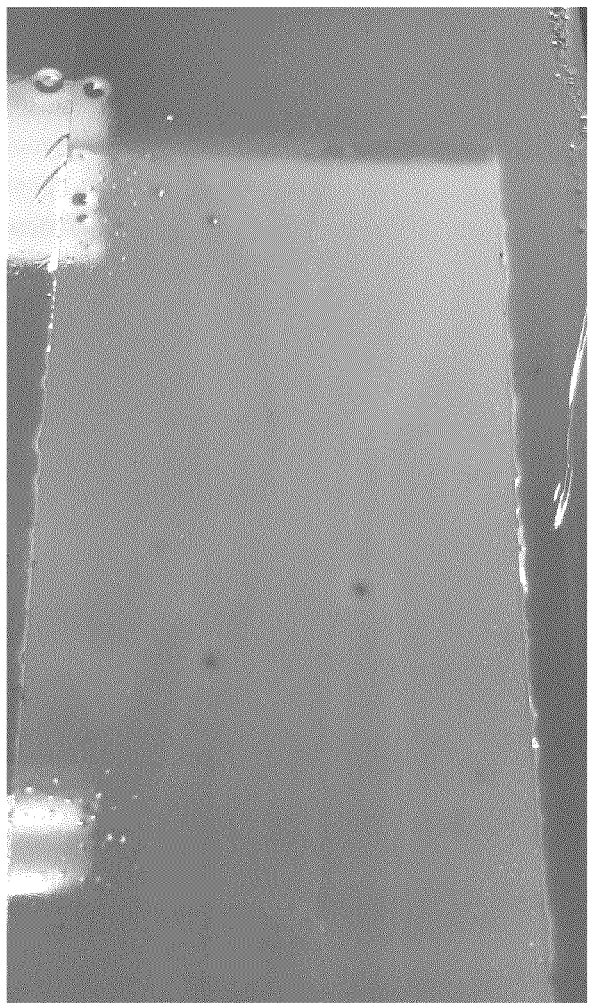
FIG. 30 shows a photograph of a polyurethane-based coating according to embodiments of the present disclosure during humidity resistance testing at day 6.
Figure 31:
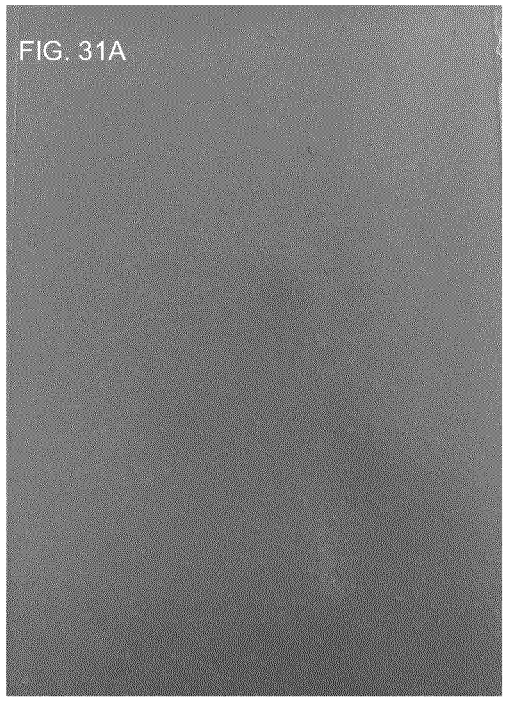
Figure 31:
Figure 32:
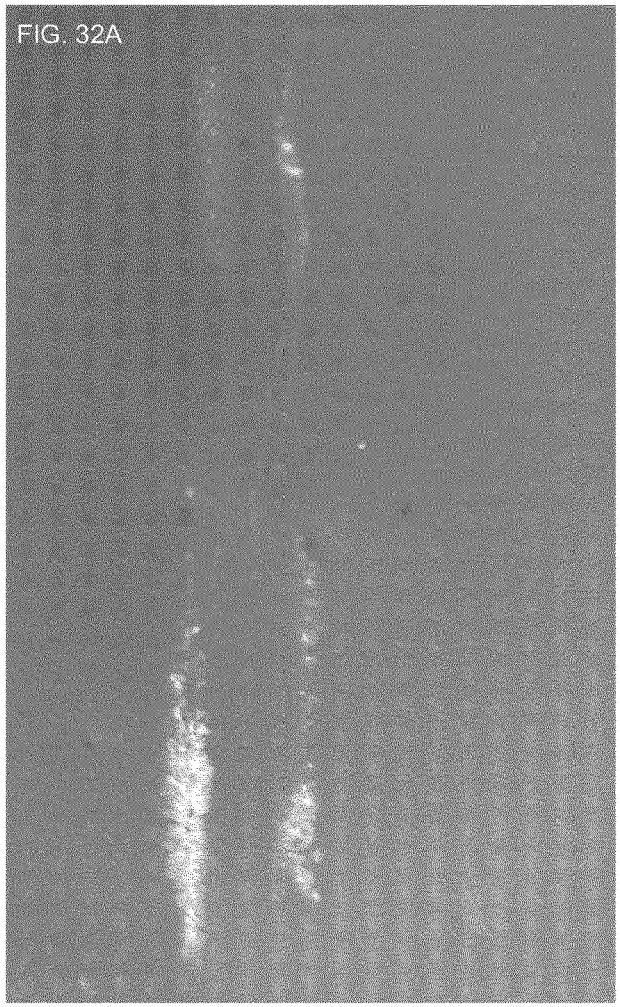
Figure 32:
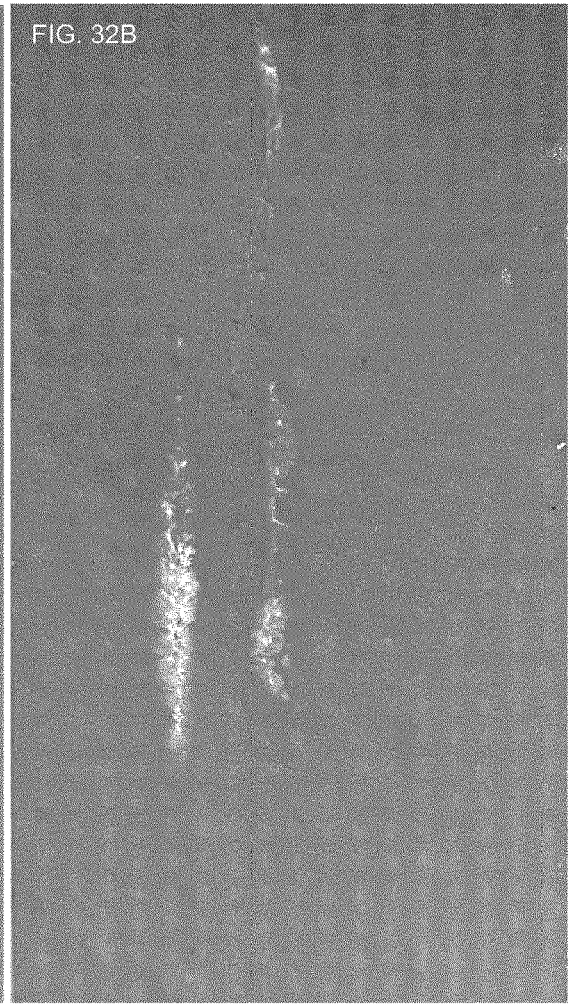
Figure 33:
Figure 33:
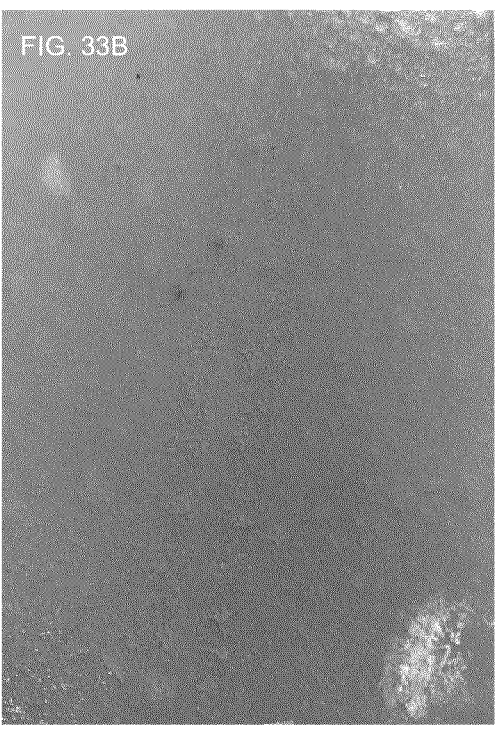

FIG. 25 through to FIG. 33 summarize the results of humidity-resistance tests of polyurethane coating formulations made according to embodiments of the present disclosure. The humidity-resistance tests were conducted in accordance with ASTM D2247 and D870: in 100% relative humidity.

Figure 34:
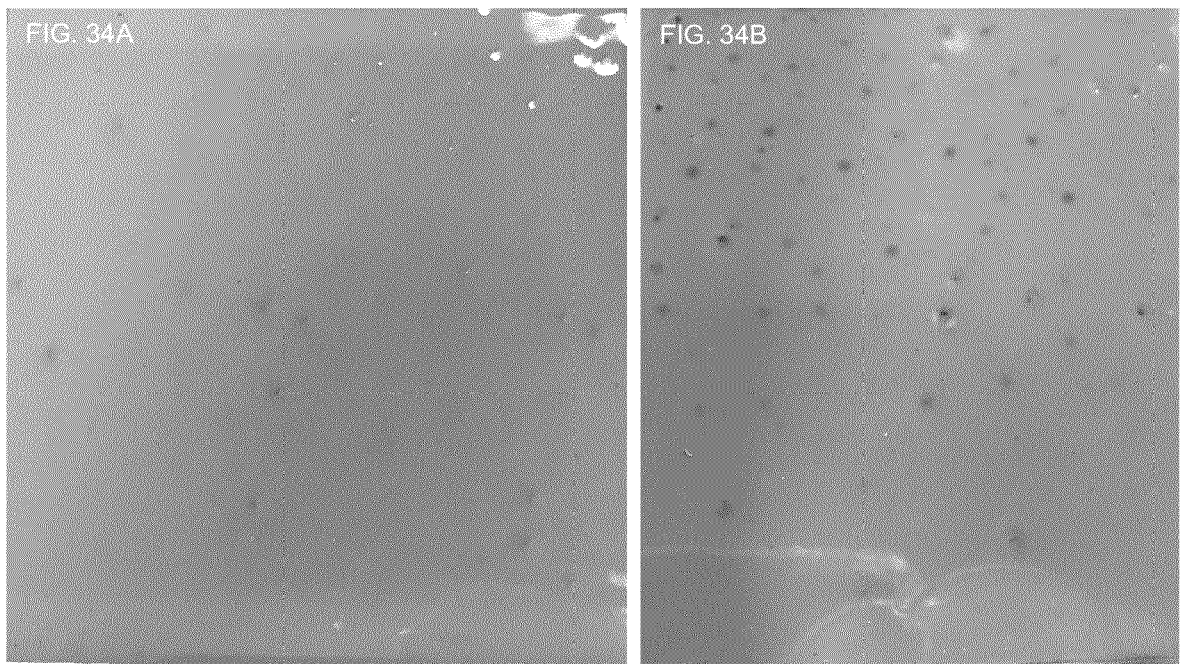
Figure 35:
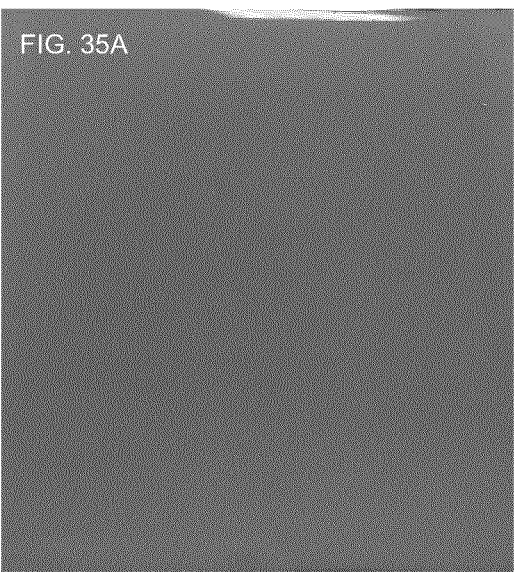
Figure 35:
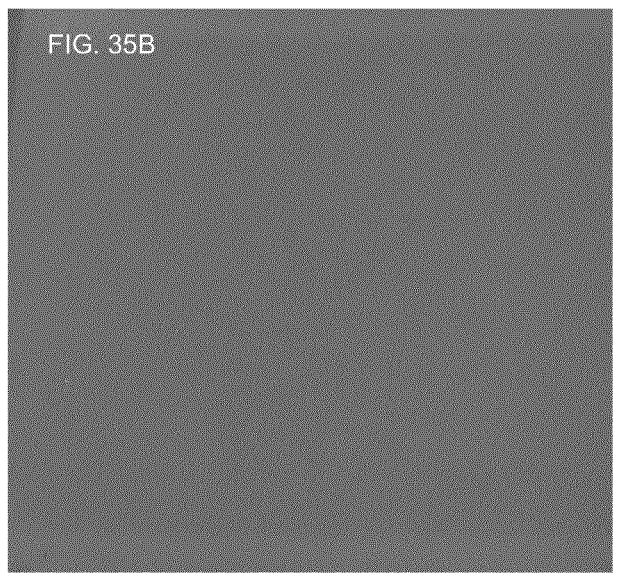
Figure 35:
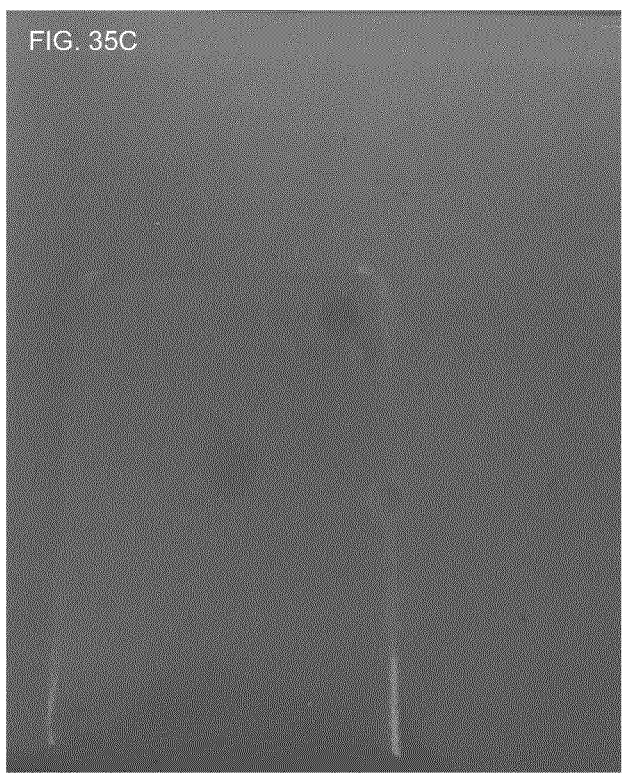
Figure 36:
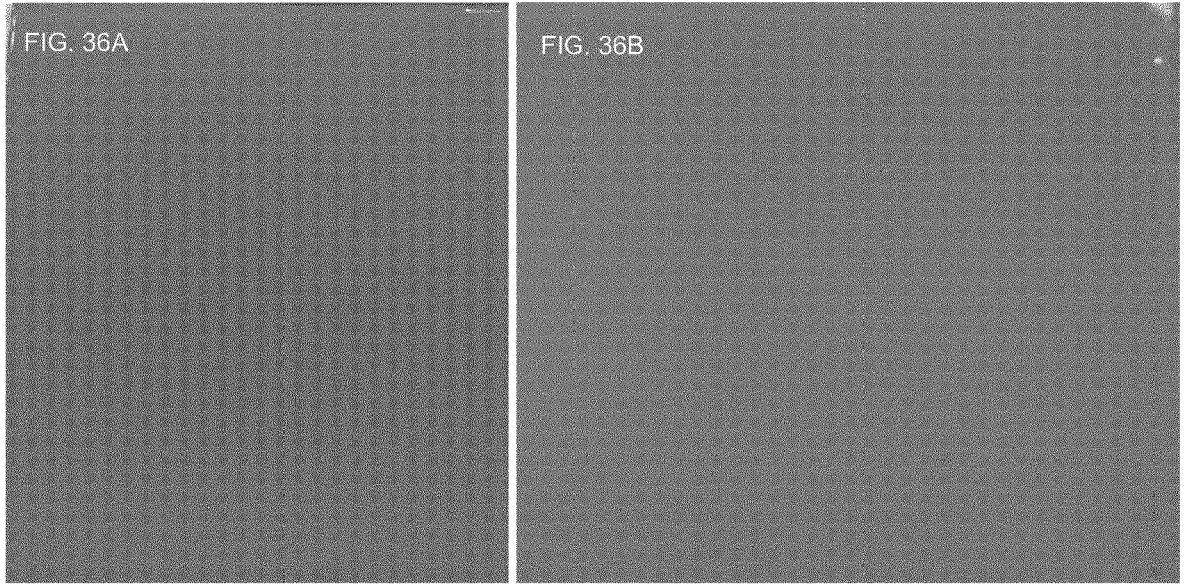
Figure 36:
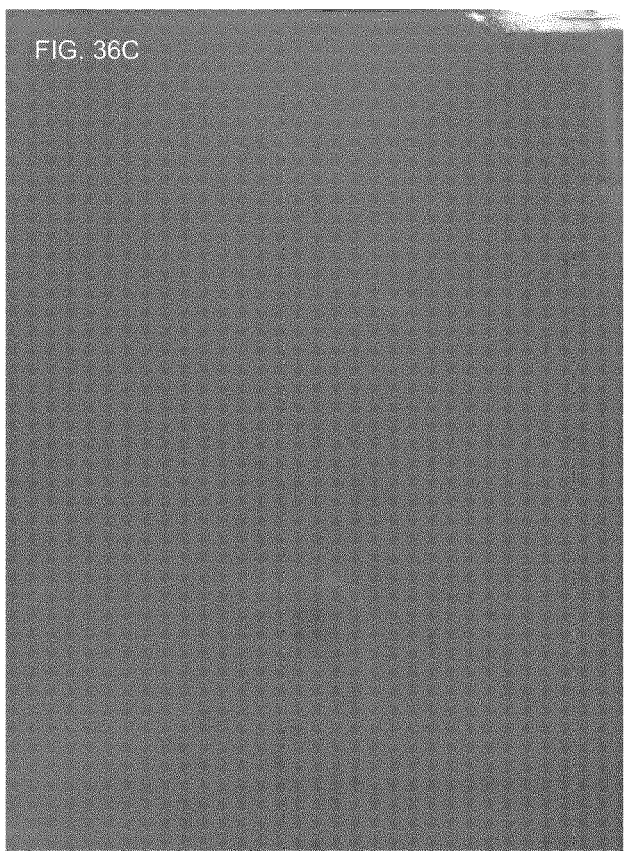
Figure 37:
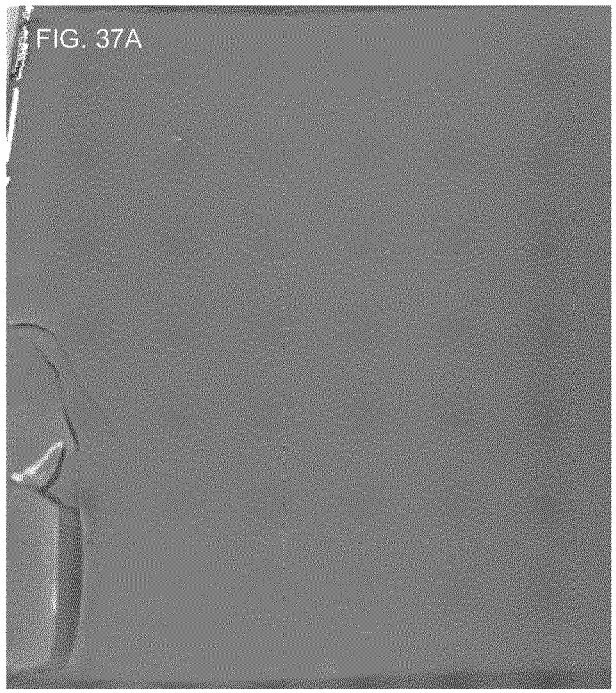
Figure 37:
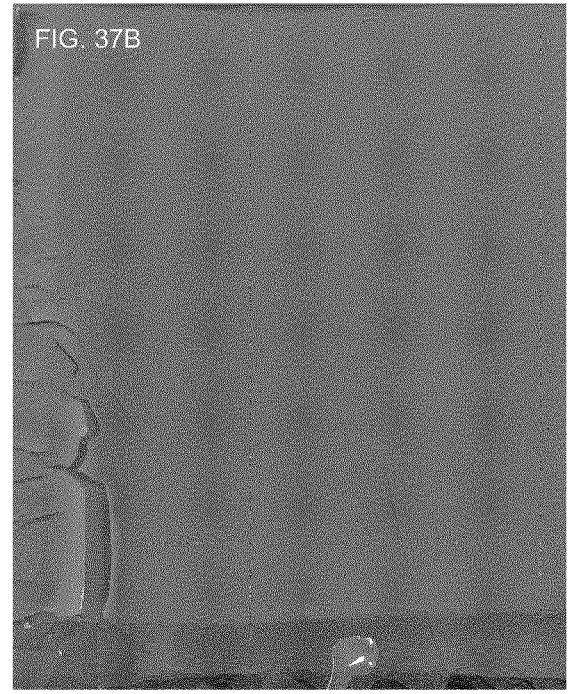
Figure 38:
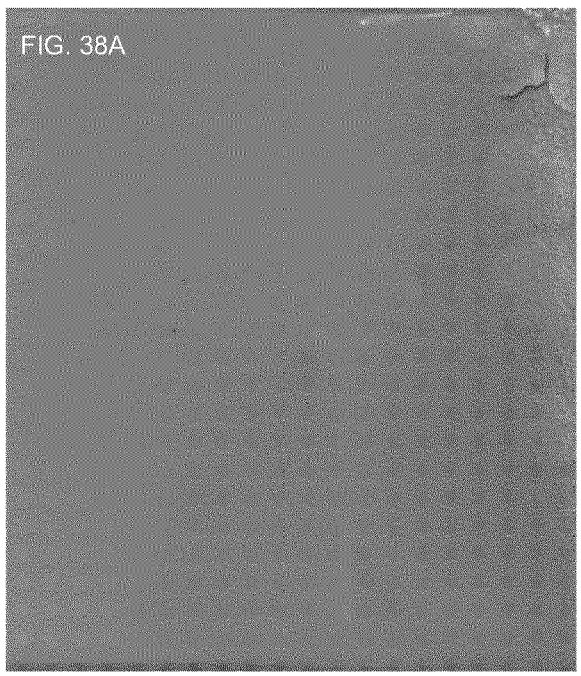
Figure 38:
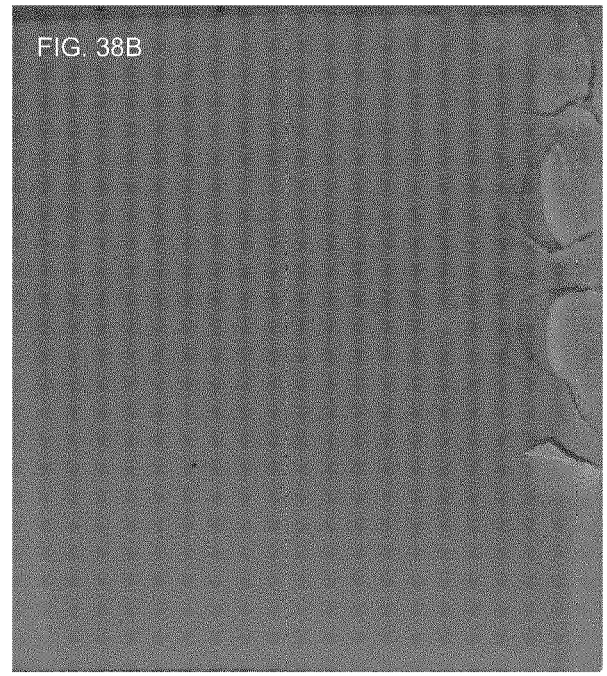
Figure 39:
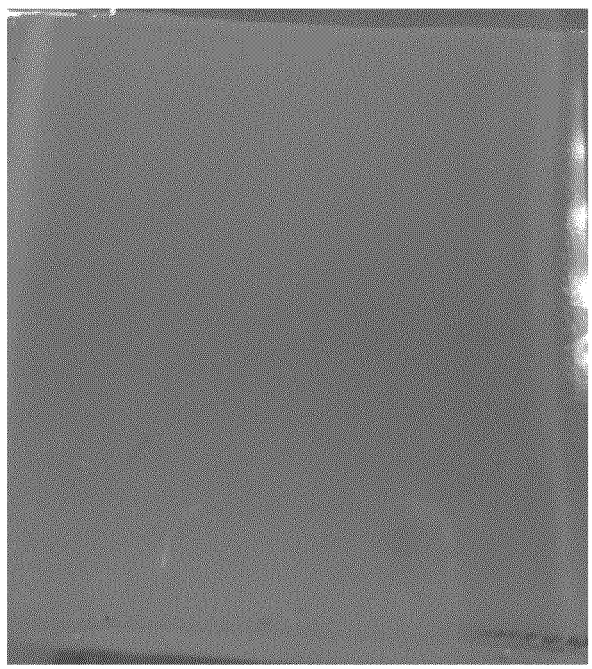
FIG. 39 shows photographs of the coating of FIG. 30 during ultraviolet resistance testing at day 6.
Figure 40:
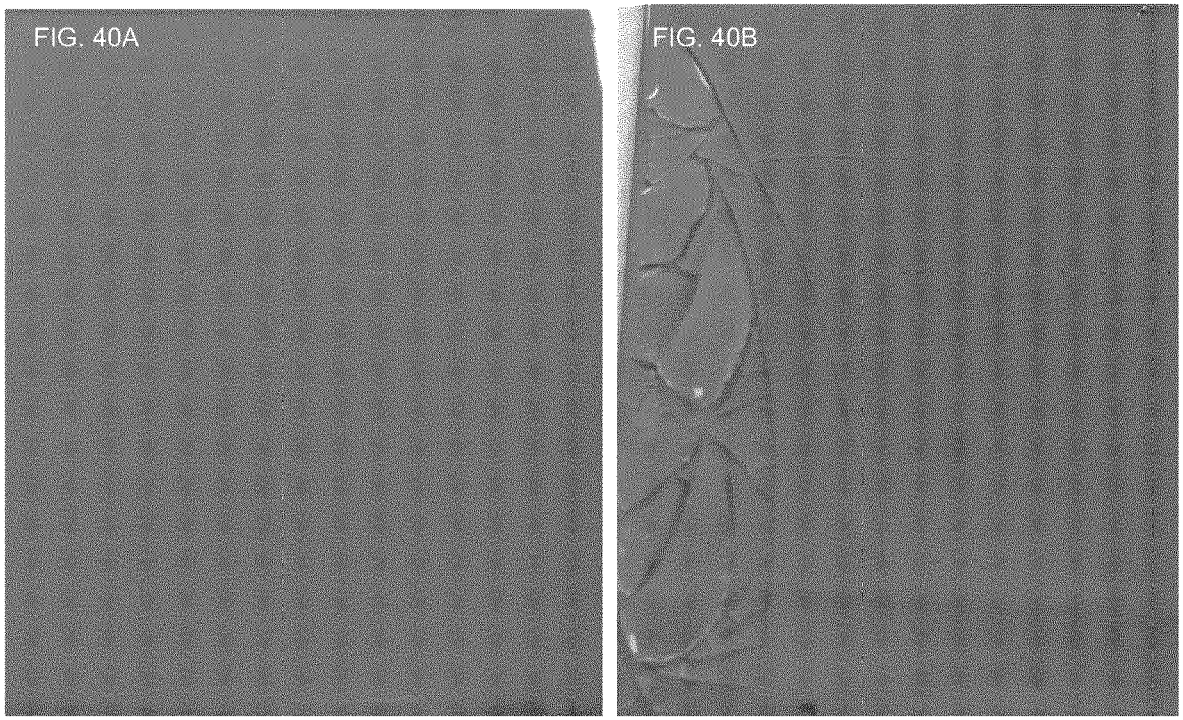
Figure 41:
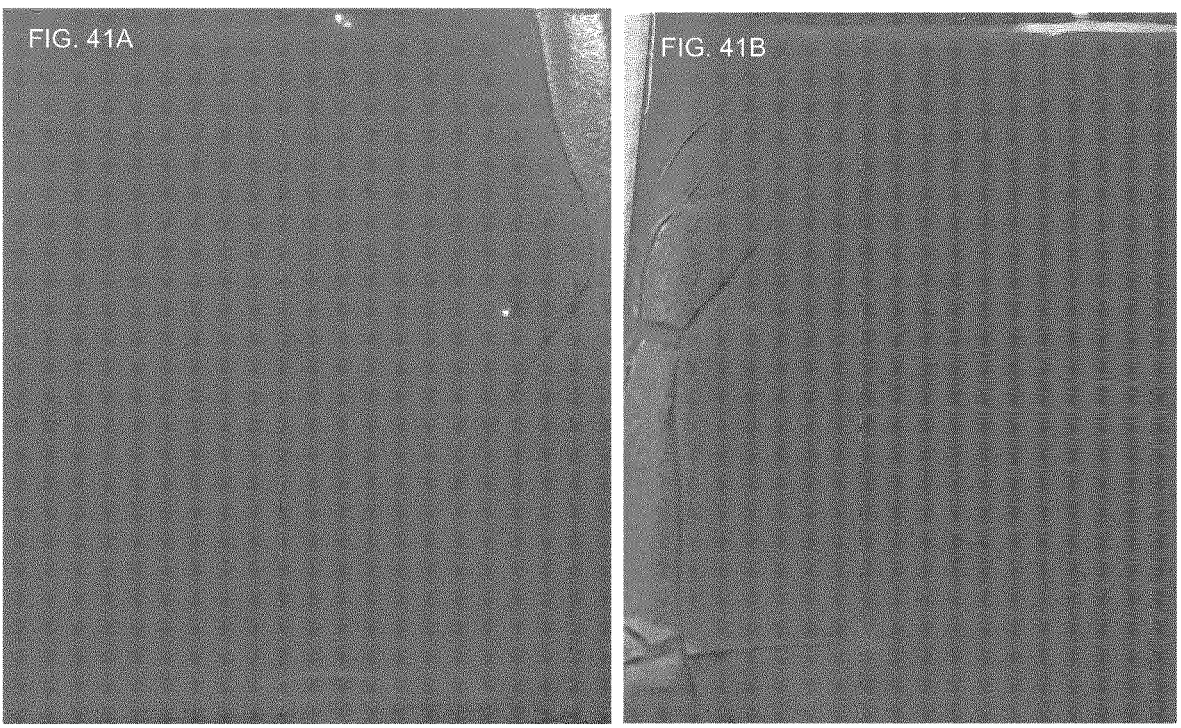
Figure 42:
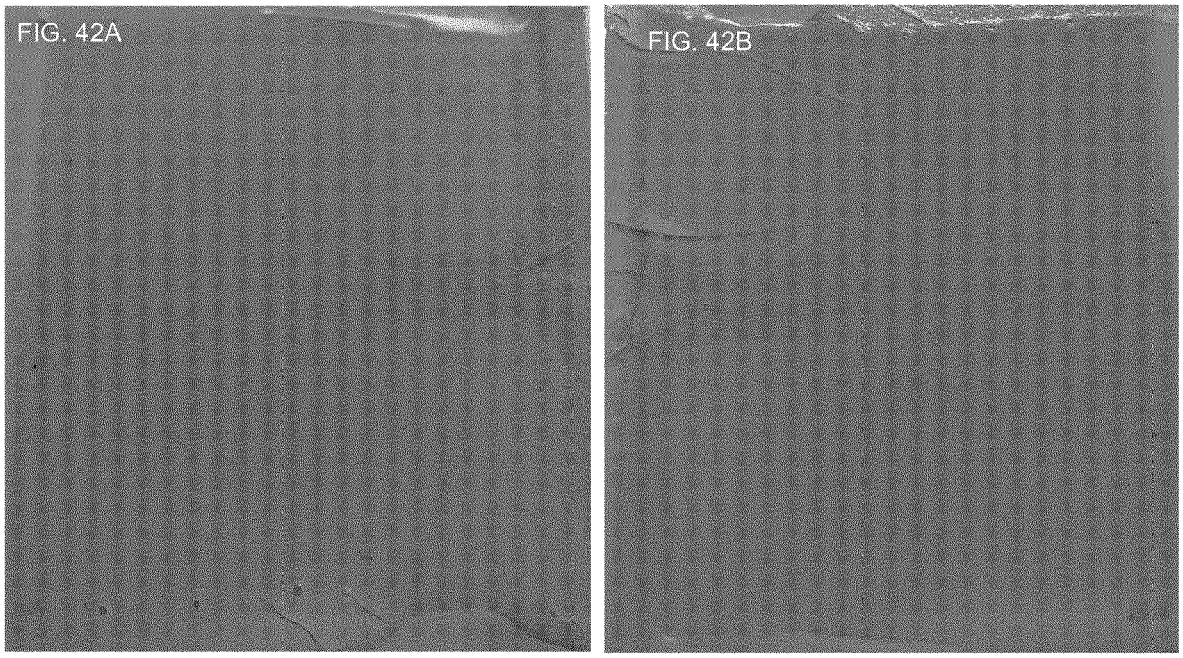

FIG. 34 through to FIG. 42 summarize the results of ultraviolet resistance tests results of polyurethane coating formulations made according to embodiments of the present disclosure. The ultraviolet resistance tests were conducted according to ASTM D4587 Standard Practice for Fluorescent UV/Condensation cycles: 4 hours of exposure to ultraviolet radiation (340 nm, 0.89 W/(m2·nm) followed by about 4 hours of condensation at about 60° C.

Figure 43:
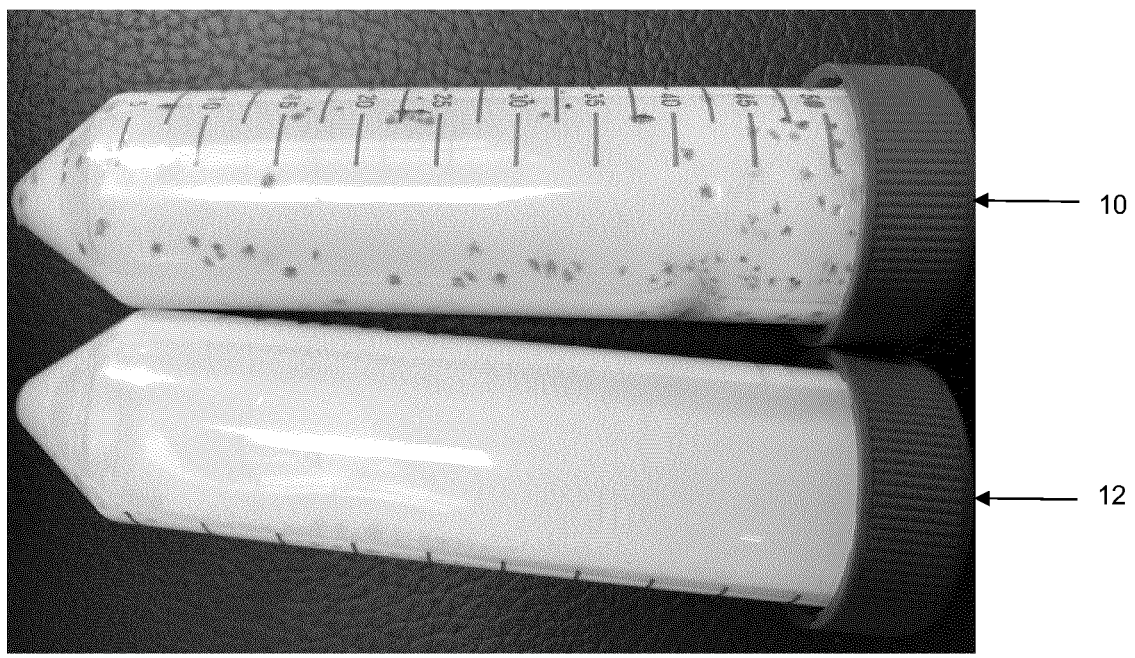
FIG. 43 shows a first vial that contains a latex emulsion (control) and a second vial that shows a latex emulsion that includes a polymerizable compound with surfactant-like properties according to an embodiment of the present disclosure.

FIG. 43 shows a first vial 10 and a second vial 12. The first vial 10 contains a volume of fluid latex emulsion that does not contain a polmerizable compound with surfactant-like properties (F3-control). The second vial 12 contains a polmerizable compound with surfactant-like properties (F4-M6-6% as shown in Table 5 and Table 9). The two vials 10, 12 were kept closed at room temperature for about ten months. the first vial 10 clearly shows the growth of microbes and the second vial 12 does not.

7. The compound according to claim 2, wherein the compound is of Formula 14:
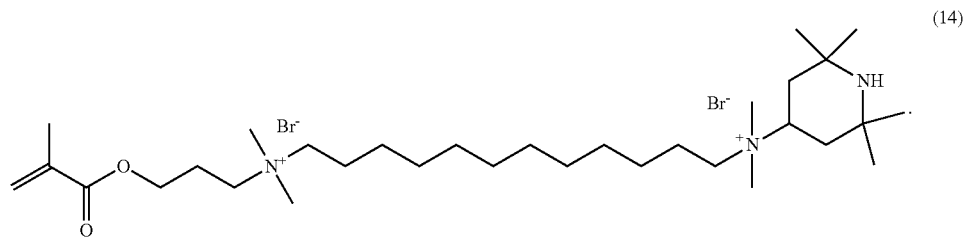

We claim:

1. A compound which is:

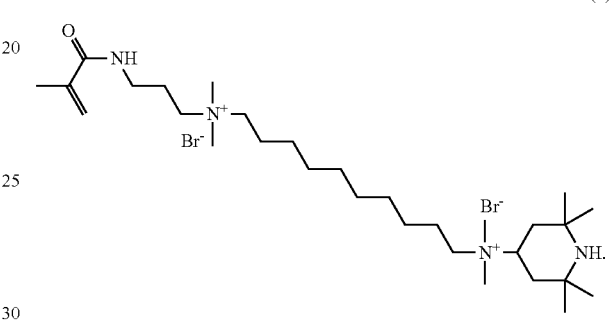

(5)

2. A compound of a formula selected from a group consisting of:

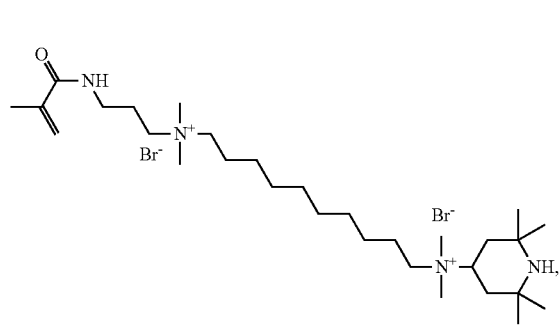

(5)

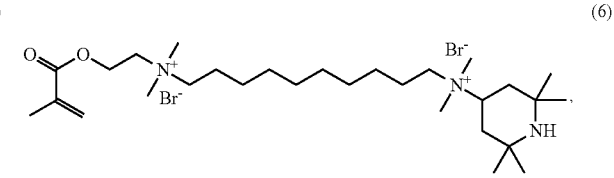

(6)

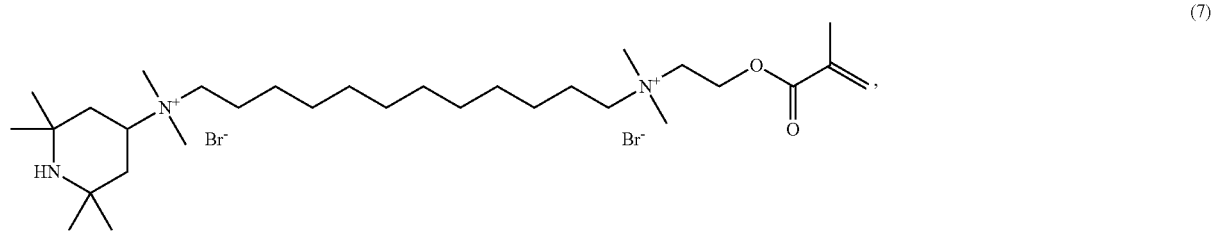

(7)

(9)
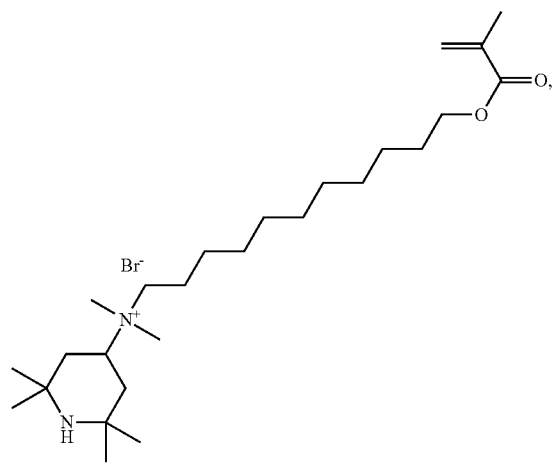
(13)
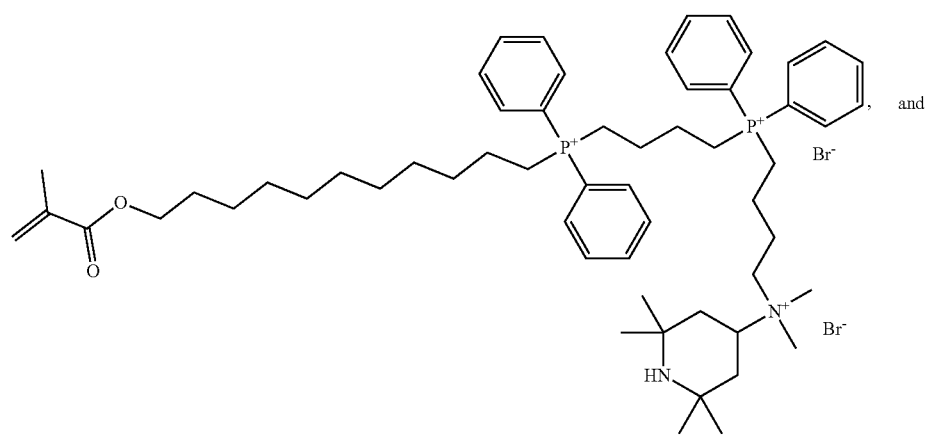
(14)
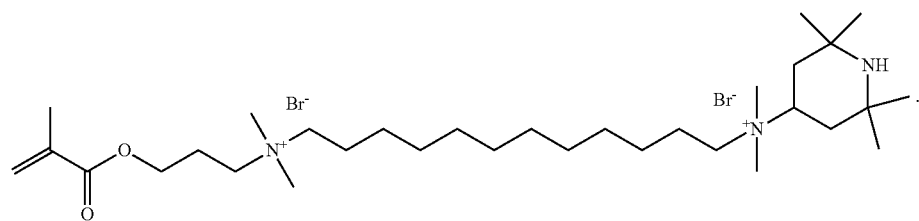
3. The compound according to claim 2, wherein the compound is of Formula 6:
(6)
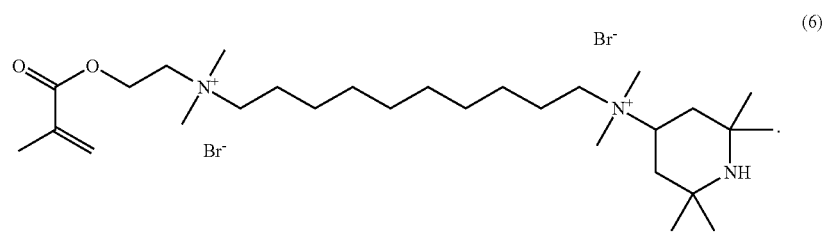 [SMILES: [Br-] ; C=C(C)C(=O)OCC[N+](C)(C)CCCCCCCCCC[N+](C)(C)C1CC(C)(C)NC(C)(C)C1 ; [Br-]]

4. The compound according to claim 2, wherein the compound is of Formula 7:
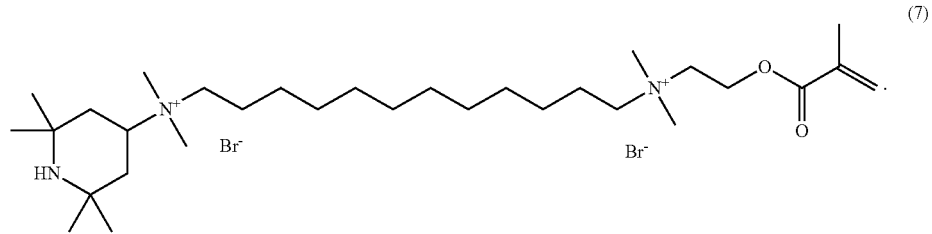 [SMILES: C=C(C)C(=O)OCC[N+](C)(C)CCCCCCCCCCCC[N+](C)(C)C1CC(C)(C)NC(C)(C)C1 ; [Br-] ; [Br-]]
(7)
5. The compound according to claim 2, wherein the compound is of Formula 9:
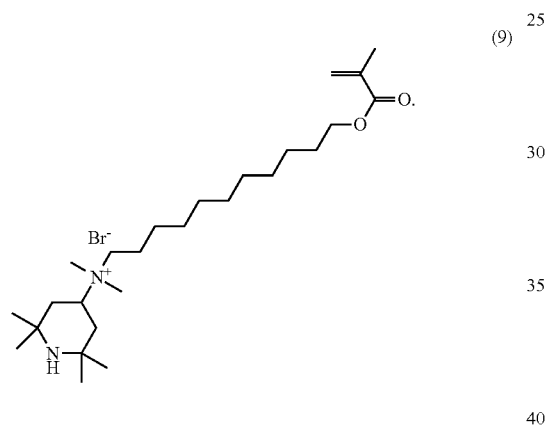
(9)
6. The compound according to claim 2, wherein the compound is of Formula 13:
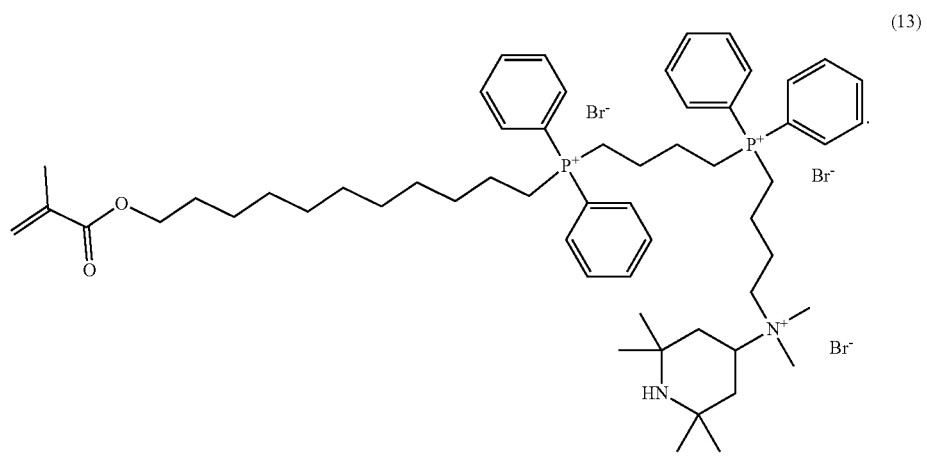 [SMILES: C=C(C)C(=O)OCCCCCCCCCCC[P+](CCCC[P+](CCCC[N+](C)(C)C1CC(C)(C)NC(C)(C)C1)(c1ccccc1)c1ccccc1)(c1ccccc1)c1ccccc1 ; [Br-] ; [Br-] ; [Br-]]
(13)